(12) United States Patent
Chan et al.

(10) Patent No.: US 11,427,561 B2
(45) Date of Patent: Aug. 30, 2022

(54) IRAK4 INHIBITING AGENTS

(71) Applicant: BIOGEN MA INC., Cambridge, MA (US)

(72) Inventors: Timothy Chan, Cambridge, MA (US); Kevin M. Guckian, Cambridge, MA (US); Tracy Jenkins, Cambridge, MA (US); Jermaine Thomas, Cambridge, MA (US); Jeffrey Vessels, Cambridge, MA (US); Gnanasambandam Kumaravel, Cambridge, MA (US); Robert Meissner, Cambridge, MA (US); Joseph P. Lyssikatos, Cambridge, MA (US); Brian Lucas, Cambridge, MA (US); Irina Leaf, Cambridge, MA (US); Jeremy Duffield, Cambridge, MA (US); Nathan Genung, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 1076 days.

(21) Appl. No.: 16/071,200

(22) PCT Filed: Jan. 18, 2017

(86) PCT No.: PCT/US2017/013946
§ 371 (c)(1),
(2) Date: Jul. 19, 2018

(87) PCT Pub. No.: WO2018/127430
PCT Pub. Date: Jul. 27, 2017

(65) Prior Publication Data
US 2021/0188809 A1      Jun. 24, 2021

Related U.S. Application Data

(63) Continuation of application No. 62/280,962, filed on Jan. 20, 2016.

(51) Int. Cl.
*C07D 401/14* (2006.01)
*A61K 45/06* (2006.01)

(52) U.S. Cl.
CPC ............ *C07D 401/14* (2013.01); *A61K 45/06* (2013.01)

(58) Field of Classification Search
None
See application file for complete search history.

(56) References Cited

FOREIGN PATENT DOCUMENTS

WO      2016/011390 A1      1/2016

OTHER PUBLICATIONS

Chaudhary et al., Recent advances in the discovery of small molecule inhibitors of interleukin-1 receptor-associated kinase 4 (IRAK4) as a therapeutic target for inflammation and oncology disorders. J Med Chem. Jan. 8, 2015;58(1):96-110.
Seganish, Inhibitors of interleukin-1 receptor-associated kinase 4 (IRAK4): a patent review (2012-2015). Expert Opin Ther Pat. Aug. 2016;26(8):917-32.
Wang et al., IRAK-4 inhibitors for inflammation. Curr Top Med Chem. 2009;9(8):724-37.
International Search Report and Written Opinion for Application No. PCT/Us2017/013946, dated Mar. 23, 2017, 10 pages.

*Primary Examiner* — Brian J Davis
(74) *Attorney, Agent, or Firm* — McCarter & English, LLP; Xin Zhang; James M. Alburger

(57) ABSTRACT

Provided are compounds of Formula I, or pharmaceutically acceptable salts thereof, and methods for their use and production. Formula (I) The compounds are IRAK-4 inhibitors useful for treating an inflammatory disease, an autoimmune disease, cancer, a cardiovascular disease, a disease of the central nervous system, a disease of the skin, an ophthalmic disease and condition, and a bone disease.

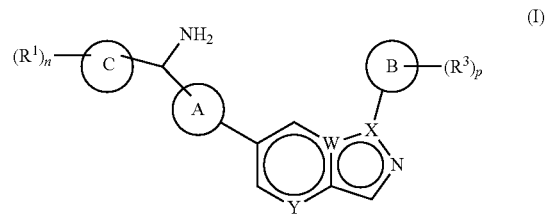

20 Claims, No Drawings

IRAK4 INHIBITING AGENTS

RELATED APPLICATIONS

This application is a 35 U.S.C. § 371 national stage filing of International Application No. PCT/US2017/013946, filed Jan. 18, 2017, which claims the benefit of U.S. Provisional Patent Application No. 62/280,962, filed Jan. 20, 2016. The entire contents of each of the foregoing applications are hereby incorporated by reference.

TECHNICAL FIELD

Provided are certain agents that inhibit IRAK4, and methods of making and using such agents.

BACKGROUND

Cellular immune responses depend on the ability of immune cells (e.g., macrophages, natural killer cells, T-cells) to detect and respond to cues in the extracellular environment by transmitting (transducing) signals across the cell membrane and into the intracellular (cytoplasmic) environment. Signals transmitted across the cell membrane may then effect a variety of "downstream" cytoplasmic and nuclear signal transduction pathways that subsequently produce a variety of immune cell responses (for example up- or down-regulation of gene transcription and translation or by releasing cytoplasmically stored components into the extracellular environment).

One cytoplasmic molecule responsible for the transmission of such downstream signals is known as "IRAK4". IRAK4 functions in cytoplasmic signal transduction pathways by interacting with components ("adaptor proteins") associated with the cytoplasmic portion of the Interleukin-1 receptor (IL-1R), Interleukin-18 receptor (IL-18R), and Toll-Like receptors (TLRs). These receptors (ILRs and the vertebrate TLRs) play important roles in innate immunity (i.e., general, non-specific immune system mechanisms of defense). In particular, TLRs play important roles in responding to microbial pathogens. TLRs are capable of eliciting a generalized immune response to pathogens via recognition of pathogen-associated molecular patterns (PAMPs). In response to such PAMPs, IL-1R/TLR signal transduction is initiated, across the cell membrane, by recruiting cytoplasmic adaptor proteins. Such adaptor proteins interact with homologous Toll/IL-1R (TIR) domains located in the cytoplasmic portion of IL-1R/TLR receptors.

The importance of adaptor proteins to immune system function is well established, as elimination of such adaptor proteins has been shown to induce significant disruptions of innate immune responses. Some examples of known IL-1R/TLR adaptor proteins are: MyD88; TIRAP/Mal; Trif/Ticam; and TRAM. MyD88, in particular, has a modular "death domain" (DD) that functions to recruit IRAK family proteins such as IRAK4. IRAK4 is thought to associate with MyD88 via IRAK4's own death domain. Moreover, loss of IRAK4/MyD88 association disrupts IL-1R/TLR signal transduction by preventing IRAK4 from phosphorylating (i.e., activating) IRAK1. Biologically, IRAK4 has been demonstrated to play a critical role in innate immunity.

SUMMARY

A first embodiment of the invention is a compound of Formula (I):

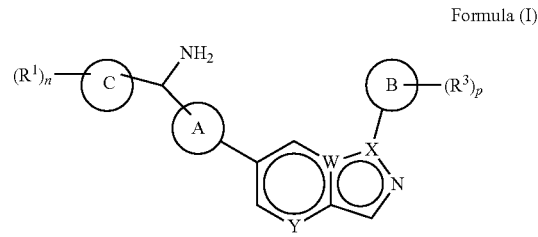

Formula (I)

or a pharmaceutically acceptable salt thereof, wherein:
Ring A is selected from phenyl and 5- or 6-membered heteroaryl;
Ring B is selected from phenyl and 5- or 6-membered heteroaryl;
Ring C is a 3- to 6-membered carbocyclyl,
n is 1, 2, or 3;
p is 0, 1, or 2;
one of W and X is N, and the other of W and X is C;
Y is N or C—$R^2$;
$R^1$ is selected from $C_{1-6}$alkyl, $C_{2-6}$alkenyl, $C_{2-6}$alkynyl, halo, —CN, —C($R^{1a}$)=NR(O$R^{1a}$), —C($R^{1a}$)=N($R^{1a}$), —C(O)$R^{1a}$, —C(O)$_2R^{1a}$, —C(O)N($R^{1a}$)$_2$, —NO$_2$, —N($R^{1a}$)$_2$, —N($R^{1a}$)C(O)$R^{1a}$, —N($R^{1a}$)C(O)$_2$ $R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N($R^{1a}$)$_2$, —S$R^{1a}$, —S(O)$R^{1a}$, —S(O)$_2R^{1a}$, —S(O)N($R^{1a}$)$_2$, and —S(O)$_2$($R^{1a}$)$_2$, wherein said $C_{1-6}$alkyl, $C_{2-6}$alkenyl, and $C_{2-6}$alkynyl are optionally substituted with one or more $R^{10}$;
$R^{1a}$ in each occurrence is independently selected from H or $C_{1-6}$alkyl wherein said $C_{1-6}$alkyl in each occurrence are optionally and independently substituted with one or more $R^{10}$;
$R^{10}$ in each occurrence is independently selected from halo, —CN, —C($R^{10a}$)=NR(O$R^{10a}$), —C($R^{10a}$)=N($R^{10a}$), —C(O)$R^{10a}$, —C(O)$_2R^{10a}$, —C(O)N($R^{10a}$)$_2$, —NO$_2$, —N($R^{10a}$)$_2$, —N($R^{10a}$)C(O)$R^{10a}$, —N($R^{10a}$)C(O)$_2R^{10a}$, —N($R^{10a}$)C(O)N($R^{10a}$)$_2$, —N($R^{10a}$)S(O)$_2$ $R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$;
$R^{10a}$ in each occurrence is independently selected from H and $C_{1-6}$alkyl, wherein said $C_{1-6}$alkyl is optionally substituted with one or more halo;
$R^2$ is selected from H, $C_{1-6}$alkyl, $C_{2-6}$alkenyl, $C_{2-6}$alkynyl, 3- to 7-membered carbocyclyl, 3- to 7-membered heterocyclyl, halo, —CN, —C($R^{2a}$)=NR(O$R^{2a}$), —C($R^{2a}$)=N($R^{2a}$), —C(O)$R^{2a}$, —C(O)$_2R^{2a}$, —C(O)N($R^{2a}$)$_2$, —NO$_2$, —N($R^{2a}$)$_2$, —N($R^{2a}$)C(O)$R^{2a}$, —N($R^{2a}$)C(O)$_2R^{2a}$, —N($R^{2a}$)C(O)N($R^{2a}$)$_2$, —N($R^{2a}$) S(O)$_2R^{2a}$, —O$R^{2a}$, —OC(O)$R^{2a}$, —OC(O)N($R^{2a}$)$_2$, —S$R^{2a}$, —S(O)$R^{2a}$, —S(O)$_2R^{2a}$, —S(O)N($R^{2a}$)$_2$, and —S(O)$_2$N($R^{2a}$)$_2$, wherein said $C_{1-6}$alkyl, $C_{2-6}$alkenyl, $C_{2-6}$alkynyl, 3- to 7-membered carbocyclyl, and 3-7 membered heterocyclyl are optionally substituted with one or more $R^{20}$;
$R^{2a}$ in each occurrence is independently selected from H and $C_{1-6}$alkyl, wherein said $C_{1-6}$alkyl in each occurrence is optionally and independently substituted with one or more $R^{20}$;

$R^{20}$ in each occurrence is independently selected from $C_{1-6}$alkyl, $C_{2-6}$alkenyl, $C_{2-6}$alkynyl, $C_{3-7}$cycloalkyl, 3- to 7-membered saturated heterocyclyl, halo, —CN, —C($R^{20a}$)=NR(O$R^{20a}$), —C($R^{20a}$)=N($R^{20a}$), —C(O)$R^{20a}$, —C(O)$_2R^{20a}$, —C(O)N($R^{20a}$)$_2$, —NO$_2$, —N($R^{20a}$)$_2$, —N($R^{20a}$)C(O)$R^{20a}$, —N($R^{20a}$)C(O)$_2R^{20a}$, —N($R^{20a}$)C(O)N($R^{20a}$)$_2$, —N($R^{20a}$)S(O)$_2R^{20a}$, —O$R^{20a}$, —OC(O)$R^{20a}$, —OC(O)N($R^{20a}$)$_2$, —S$R^{20a}$, —S(O)$R^{20a}$, —S(O)$_2R^{20a}$, —S(O)N($R^{20a}$)$_2$, and —S(O)$_2$N($R^{20a}$)$_2$, wherein said $C_{1-6}$alkyl, $C_{2-6}$alkenyl, $C_{2-6}$alkynyl, $C_{3-7}$cycloalkyl, and 3-7 membered saturated heterocyclyl in each occurrence are optionally and independently substituted with one or more $R^{25}$;

$R^{20a}$ in each occurrence is independently selected from H and $C_{1-6}$alkyl, wherein said $C_{1-6}$alkyl is optionally substituted with $R^{25}$;

$R^{25}$ is selected from halo and —O$R^{25a}$;

$R^{25a}$ is selected from H and $C_{1-6}$alkyl;

$R^3$ is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —C($R^{3a}$)=NR(O$R^{3a}$), —C($R^{3a}$)=N($R^{3a}$), —C(O)$R^{3a}$, —C(O)$_2R^{3a}$, —C(O)N($R^{3a}$)$_2$, —NO$_2$, —N($R^{3a}$)$_2$, —N($R^{3a}$)C(O)$R^{3a}$, —N($R^{3a}$)C(O)$_2$ $R^{3a}$, —N($R^{3a}$)C(O)N($R^{3a}$)$_2$, —N($R^{3a}$)S(O)$_2R^{3a}$, —O$R^{3a}$, —OC(O)$R^{3a}$, —OC(O)N($R^{3a}$)$_2$, —S$R^{3a}$, —S(O)$R^{3a}$, —S(O)$_2R^{3a}$, —S(O)N($R^{3a}$)$_2$, and —S(O)$_2$N($R^{3a}$)$_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one or more $R^{30}$;

$R^{3a}$ in each occurrence is independently selected from H, $C_{1-6}$alkyl, 3- to 6-membered carbocyclyl, and 3- to 6-membered heterocyclyl, wherein said $C_{1-6}$alkyl, 3- to 6-membered carbocyclyl, and 3- to 6-membered heterocyclyl in each occurrence are optionally and independently substituted with one or more $R^{30}$;

$R^{30}$ in each occurrence is independently selected from $C_{1-6}$alkyl, $C_{2-6}$alkenyl, $C_{2-6}$alkynyl, 3- to 6-membered carbocyclyl, 3- to 6-membered heterocyclyl, halo, —CN, —C($R^{30a}$)=NR(O$R^{30a}$), —C($R^{30a}$)=N($R^{30a}$), —C(O)$R^{30a}$, —C(O)$_2R^{30a}$, —C(O)N($R^{30a}$)$_2$, —NO$_2$, —N($R^{30a}$)$_2$, —N($R^{30a}$)C(O)$R^{30a}$, —N($R^{30a}$)C(O)$_2R^{30a}$, —N($R^{30a}$)C(O)N($R^{30a}$)$_2$, —N($R^{30a}$)S(O)$_2R^{30a}$, —O$R^{30a}$, —OC(O)$R^{30a}$, —OC(O)N($R^{30a}$)$_2$, —S$R^{30a}$, —S(O)$R^{30a}$, —S(O)$_2R^{30a}$, —S(O)N($R^{30a}$)$_2$, and —S(O)$_2$N($R^{30a}$)$_2$, wherein said $C_{1-6}$alkyl, $C_{2-6}$alkenyl, $C_{2-6}$alkynyl, 3-6 membered carbocyclyl, 3- to 6-membered heterocyclyl in each occurrence are optionally and independently substituted with one or more $R^{35}$;

$R^{30a}$ in each occurrence is independently selected from H and $C_{1-4}$alkyl, wherein $C_{1-4}$alkyl is optionally substituted with one or more $R^{35}$;

$R^{35}$ in each occurrence is independently selected from halo and —O$R^{35a}$; and $R^{35a}$ in each occurrence is independently selected from H and $C_{1-6}$alkyl.

Also provided is a pharmaceutical composition comprising at least one compound described herein, or a pharmaceutically acceptable salt thereof, and at least one pharmaceutically acceptable excipient.

Also provided is a method of decreasing the expression or activity of IRAK-4, or to otherwise affect the properties and/or behavior of IRAK-4 polypeptides or polynucleotides comprising administering to said mammal an effective amount of at least one compound described herein, or a pharmaceutically acceptable salt thereof.

Also provided is a method for treating an inflammatory disease in a subject, the method comprising administering to the patient a therapeutically effective amount of a compound described herein, or a pharmaceutically acceptable salt thereof, thereby treating the inflammatory disease in the subject.

Also provided is a method for treating an autoimmune disease, cancer, cardiovascular disease, a disease of the central nervous system, a disease of the skin, an ophthalmic disease and condition, and bone disease in a subject, the method comprising administering to the patient a therapeutically effective amount of a compound disclosed herein, or a pharmaceutically acceptable salt thereof, thereby treating the autoimmune disease, cancer, cardiovascular disease, disease of the central nervous system, disease of the skin, ophthalmic disease and condition, and bone disease in the subject.

Other features or advantages will be apparent from the following detailed description of several embodiments, and also from the appended claims.

DETAILED DESCRIPTION

The compounds or pharmaceutically acceptable salts thereof as described herein, can have activity as IRAK4 modulators. In particular, compounds or pharmaceutically acceptable salts thereof as described herein, can be IRAK4 inhibitors.

A second embodiment of the invention is a compound of Formula (II):

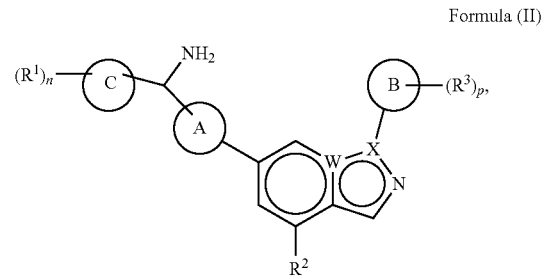

Formula (II)

pharmaceutically acceptable salt thereof, wherein the values of the variables are as defined for the first embodiment.

A third embodiment of the invention is a compound of Formula (III):

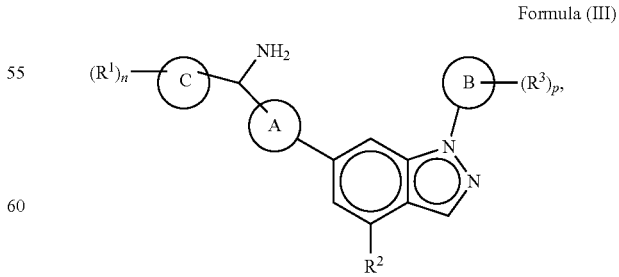

Formula (III)

or a pharmaceutically acceptable salt thereof, wherein the values of the variables are as defined for the first embodiments.

A fourth embodiment of the invention is a compound of Formula (IV):

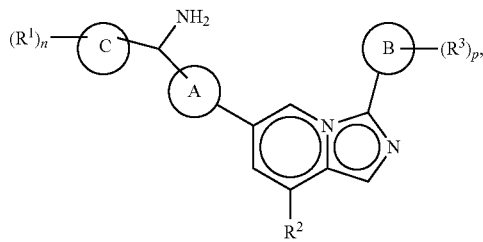

or a pharmaceutically acceptable salt thereof, wherein the values of the variables are as defined for the first embodiment.

In a fifth embodiment of the invention, the compound is represented by the formula (I), (II), (III), or (IV), wherein Ring A is 5- or 6-membered heteroaryl and Ring B is 5- or 6-membered heteroaryl, wherein the values of the other variables are as defined for the first embodiment.

In a sixth embodiment of the invention, the compound is represented by the formula (I), (II), (III), or (IV), wherein Ring A is a 5- or 6-membered heteroaryl and Ring B is phenyl, wherein the values of the other variables are as defined for the first embodiment.

In a seventh embodiment of the invention, the compound is represented by the formula (I), (II), (III), or (IV), wherein Ring A is a phenyl and Ring B is a 5- or 6-membered heteroaryl, wherein the values of the other variables are as defined for the first embodiment.

In an eighth embodiment of the invention, the compound is represented by the formula (I), (II), (III), or (IV), wherein the 5- or 6-membered heteroaryl in each occurrence is independently selected from pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, or tetrazinyl, wherein the values of the other variables are as defined for the first, fifth, sixth, and seventh embodiments.

In a ninth embodiment of the invention, the compound is represented by the formula (I), (II), (III), or (IV), wherein the 5- or 6-membered heteroaryl in each occurrence is independently selected from pyridinyl, pyrimidinyl, pyrazinyl, thiazolyl, imidazolyl, oxazolyl pyrazolyl, and thiophenyl, wherein the values of the other variables are as defined for the first, fifth, sixth, seventh and eighth embodiments.

In a tenth embodiment of the invention, the compound is represented by the formula (I), (II), (III), or (IV), wherein Ring A is a phenyl and Ring B is phenyl, wherein the values of the other variables are as defined for the first embodiment.

In an eleventh embodiment of the invention, the compound is represented by the formula (I), (II), (III), or (IV), $R^1$ is selected from $C_{1-6}$alkyl, halo, —CN, —C(O)$R^{1a}$, —C(O)$_2R^{1a}$, —C(O)N($R^{1a}$)$_2$, —NO$_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —O$R^{1a}$, —OC(O)$R^{1a}$, —OC(O)N($R^{1a}$)$_2$, and —S$R^{1a}$, wherein said $C_{1-6}$alkyl is optionally substituted with one to four $R^{10}$;

$R^{1a}$ in each occurrence is independently selected from H or $C_{1-6}$alkyl wherein said $C_{1-6}$alkyl in each occurrence are optionally and independently substituted with one or to four $R^{10}$;

$R^{10}$ in each occurrence is independently selected from halo, —CN, —C(O)$R^{10a}$, —C(O)$_2R^{10a}$, —C(O)N($R^{10a}$)$_2$, —NO$_2$, —N($R^{10a}$)$_2$, —N($R^{10a}$)C(O)$R^{10a}$, —N($R^{10a}$)C(O)$_2R^{10a}$, —O$R^{10a}$, —OC(O)$R^{10a}$, —OC(O)N($R^{10a}$)$_2$, and —S$R^{10a}$; and $R^{10a}$ in each occurrence is independently selected from H and $C_{1-6}$alkyl, wherein said $C_{1-6}$alkyl is optionally substituted with one to four halo, wherein said $C_{1-6}$alkyl is optionally substituted with one to three halo, wherein the values of the other variables are as defined for the first, fifth, sixth, seventh, eighth, ninth and tenth embodiments.

In a twelfth embodiment of the invention, the compound is represented by the formula (I), (II), (III), or (IV), wherein $R^1$ is selected from $C_{1-6}$alkyl, halo, —O$R^{1a}$, wherein said $C_{1-6}$alkyl are optionally substituted with one to three $R^{10}$;

$R^{1a}$ in each occurrence is independently selected from H or $C_{1-6}$alkyl wherein said $C_{1-6}$alkyl in each occurrence are optionally and independently substituted with one to three $R^{10}$;

$R^{10}$ in each occurrence is independently selected from halo or —O$R^{10a}$; and $R^{10a}$ in each occurrence is independently selected from H and $C_{1-6}$alkyl, wherein said $C_{1-6}$alkyl is optionally substituted with one to three halo, wherein the values of the other variables are as defined for the first, fifth, sixth, seventh, eighth, ninth, tenth and eleventh embodiments.

In a thirteenth embodiment of the invention, the compound is represented by the formula (I), (II), (III), or (IV), wherein n is 1 and $R^1$ is OH or —CH$_2$OH, wherein the values of the other variables are as defined for the first, fifth, sixth, seventh, eighth, ninth, tenth, eleventh and twelfth embodiments.

In a fourteenth embodiment of the invention, the compound is represented by the formula (I), (II), (III), or (IV), wherein n is 2 and $R^1$ is halo, wherein the values of the other variables are as defined for the first, fifth, sixth, seventh, eighth, ninth, tenth, eleventh, and twelfth embodiments.

In a fifteenth embodiment of the invention, the compound is represented by the formula (I), (II), (III), or (IV), wherein Ring C is cyclobutyl, wherein the values of the other variables are as defined for the first, fifth, sixth, seventh, eighth, ninth, tenth, eleventh, twelfth, thirteenth, and fourteenth embodiments.

In a sixteenth embodiment of the invention, the compound is represented by the formula (I), (II), (III), or (IV), wherein Ring C is cyclopentyl; wherein the values of the other variables are as defined for the first, fifth, sixth, seventh, eighth, ninth, tenth, eleventh, twelfth, thirteenth, and fourteenth embodiments.

In a seventeenth embodiment of the invention, the compound is represented by the formula (I), (II), (III), or (IV), $R^2$ is selected from H, $C_{1-6}$alkyl, $C_{2-6}$alkenyl, $C_{2-6}$alkynyl, 3- to 7-membered carbocyclyl selected from cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, cycloheptatrienyl, and phenyl; 3- to 7-membered heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, azirinyl, oxirenyl, thiirenyl, diazirinyl, azetyl, oxetyl, thietyl, pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, thiazepinyl, dihydrofuranyl, imidazolinyl, and dihydropyranyl; halo, —CN, —C(O)$R^{2a}$, —C(O)$_2R^{2a}$, —C(O)N($R^{2a}$)$_2$, —NO$_2$, —N($R^{2a}$)$_2$, —N($R^{2a}$)C(O)$R^{2a}$, —N($R^{2a}$)C(O)$_2R^{2a}$, —N($R^{2a}$)C(O)N($R^{2a}$)$_2$, —O$R^{2a}$, —OC(O)$R^{2a}$, and —OC(O)N($R^{2a}$)$_2$, wherein said $C_{1-6}$alkyl, $C_{2-6}$alkenyl, $C_{2-6}$alkynyl, 3- to 7-membered carbocyclyl, and 3-7 membered heterocyclyl are optionally substituted with one to three $R^{20}$;

$R^{2a}$ in each occurrence is independently selected from H and $C_{1-4}$alkyl, wherein said $C_{1-4}$alkyl in each occurrence is optionally and independently substituted with one to three $R^{20}$;

$R^{20}$ in each occurrence is independently selected from $C_{1-6}$alkyl, $C_{2-6}$alkenyl, $C_{2-6}$alkynyl, $C_{3-7}$cycloalkyl selected from cyclopropyl, cyclobutyl, cyclopentyl, cyclohexyl, and cycloheptyl; 3- to 7-membered saturated heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, and thiepanyl; halo, —CN, —C(O)$R^{20a}$, —C(O)$_2R^{20a}$, —C(O)N($R^{20a}$)$_2$, —N($R^{20a}$)$_2$, —N($R^{20a}$)C(O)$R^{20a}$, —N($R^{20a}$)C(O)$_2R^{20a}$, —N($R^{20a}$)C(O)N($R^{20a}$)$_2$, —O$R^{20a}$, —OC(O)$R^{20a}$, and —OC(O)N($R^{20a}$)$_2$, wherein said $C_{1-6}$alkyl, $C_{2-6}$alkenyl, $C_{2-6}$alkynyl, $C_{3-7}$cycloalkyl, and 3-7 membered saturated heterocyclyl in each occurrence are optionally and independently substituted with one to three $R^{25}$;

$R^{20a}$ in each occurrence is independently selected from H and $C_{1-4}$alkyl, wherein said $C_{1-4}$alkyl is optionally substituted with $R^{25}$;

$R^{25}$ is selected from halo and —O$R^{25a}$; and $R^{25a}$ is selected from H and $C_{1-4}$alkyl, wherein the values of the other variables are as defined for the first, fifth, sixth, seventh, eighth, ninth, tenth, eleventh, twelfth, thirteenth, fourteenth, fifteenth, and sixteenth embodiments. In an alternative aspect of this embodiment, $R^{10}$ may also include —S$R^{10a}$, $C_{2-6}$alkenyl, $C_{2-6}$alkynyl, —C(O)$R^{10a}$, —S(O)$_2R^{10a}$, and —S(O)$R^{10a}$.

In an eighteenth embodiment of the invention, the compound is represented by the formula (I), (II), (III), or (IV), $R^2$ is H, $C_{1-4}$alkyl, $C_{2-4}$alkenyl, halo, —C(O)$_2R^{2a}$, —C(O)N($R^{2a}$)$_2$, —N($R^{2a}$)$_2$, N($R^{2a}$)C(O)$R^{2a}$, —CN, —O$R^{2a}$, cyclopropyl, aziridinyl, azetidinyl, oxetanyl, pyrrolidinyl, imidazolidinyl, pyrazolidinyl, oxazolidinyl, isoxazolidinyl, piperidinyl, piperazinyl, azepanyl, oxepanyl, azirinyl, azetyl, pyrrolyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, pyrazinyl, pyrimidinyl, pyridazinyl, triazinyl, tetrazinyl, azepinyl, diazepinyl, thiazepinyl, and, imidazolinyl, wherein said $C_{1-4}$alkyl is optionally substituted with one to three groups selected from cyclopropyl, cyclobutyl, cyclopentyl, cyclohexyl, cycloheptyl, —O$R^{20a}$, —N($R^{20a}$)$_2$, N($R^{20a}$)C(O)$R^{20a}$, and halo;

$R^{2a}$ in each occurrence is independently selected from H and $C_{1-4}$alkyl, wherein said $C_{1-4}$alkyl is optionally substituted with cyclopropyl, cyclobutyl, cyclopentyl, cyclohexyl, and cycloheptyl; and $R^{20a}$ in each occurrence is independently selected from H and $C_{1-4}$alkyl, wherein the values of the other variables are as defined for the first, fifth, sixth, seventh, eighth, ninth, tenth, eleventh, twelfth, thirteenth, fourteenth, fifteenth, sixteenth, and seventeenth embodiments.

In a nineteenth embodiment of the invention, the compound is represented by the formula (I), (II), (III), or (IV), $R^2$ is H or —O$R^{2a}$; $R^{2a}$ in each occurrence is independently selected from H and $C_{1-4}$alkyl, wherein said $C_{1-4}$alkyl is optionally substituted with one to three halo, wherein the values of the other variables are as defined for the first, fifth, sixth, seventh, eighth, ninth, tenth, eleventh, twelfth, thirteenth, fourteenth, fifteenth, sixteenth, seventeenth, and eighteenth embodiments.

In a twentieth embodiment of the invention, the compound is represented by the formula (I), (II), (III), or (IV), wherein p is 1 or 2;

each $R^3$ is independently selected from $C_{1-6}$alkyl, $C_{3-6}$cycloalkyl selected from cyclopropyl, cyclobutyl, cyclopentyl, and cyclohexyl, 3- to 6-membered saturated heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, and trithianyl; halo, —CN, —C(O)$R^{3a}$, —C(O)$_2R^{3a}$, —C(O)N($R^{3a}$)$_2$, —N($R^{3a}$)$_2$, —N($R^{3a}$)C(O)$R^{3a}$, —N($R^{3a}$)C(O)$_2R^{3a}$, —N($R^{3a}$)C(O)N($R^{3a}$)$_2$, —O$R^{3a}$, —OC(O)$R^{3a}$, —OC(O)N($R^{3a}$)$_2$, —S$R^{3a}$, —S(O)$R^{3a}$, —S(O)$_2R^{3a}$, —S(O)N($R^{3a}$)$_2$, and —S(O)$_2$N($R^{3a}$)$_2$, wherein said $C_{1-6}$alkyl, $C_{3-6}$cycloalkyl, and 3- to 6-membered saturated heterocyclyl are optionally substituted with one to three $R^{30}$;

$R^{3a}$ in each occurrence is independently selected from H, $C_{1-6}$alkyl, 3- to 6-membered carbocyclyl selected from cyclopropyl, cyclobutyl, cyclopentyl, cyclo hexyl, cyclopropenyl, cyclobutenyl, cyclopenentyl, cyclohexenyl, cyclobutadienyl, cyclopentadienyl, cyclohexadienyl, and phenyl, and 3- to 6-membered heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azirinyl, oxirenyl, thiirenyl, diazirinyl, azetyl, oxetyl, thietyl, pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, dihydrofuranyl, imidazolinyl, and dihydropyranyl; wherein said $C_{1-6}$alkyl, 3- to 6-membered carbocyclyl, and 3- to 6-membered saturated heterocyclyl in each occurrence are optionally and independently substituted with one to three $R^{30}$;

$R^{30}$ in each occurrence is independently selected from $C_{1-6}$alkyl, 3- to 6-membered carbocyclyl selected from cyclopropyl, cyclobutyl, cyclopentyl, cyclohexyl, cyclopropenyl, cyclobutenyl, cyclopenentyl, cyclohexenyl, cyclobutadienyl, cyclopentadienyl, cyclohexadienyl, and phenyl; 3- to 6-membered heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azirinyl, oxirenyl, thiirenyl, diazirinyl, azetyl, oxetyl, thietyl, pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, dihydrofuranyl, imidazolinyl, and dihydropyranyl; halo, —CN, —C(O)$R^{30a}$, —C(O)$_2$$R^{30a}$, —C(O)N($R^{30a}$)$_2$, —N($R^{30a}$)$_2$, —N($R^{30a}$)C(O)$R^{30a}$, —N($R^{30a}$)C(O)$_2$$R^{30a}$, —N($R^{30a}$)C(O)N($R^{30a}$)$_2$, —O$R^{30a}$, —OC(O)$R^{30a}$, —OC(O)N($R^{30a}$)$_2$, S$R^{30a}$, —S(O)$R^{30a}$, —S(O)$_2$$R^{30a}$, —S(O)N($R^{30a}$)$_2$, and —S(O)$_2$N($R^{30a}$)$_2$, wherein said $C_{1-6}$alkyl, 3-6 membered carbocyclyl, and 3- to 6-membered heterocyclyl in each occurrence are optionally and independently substituted with one to three $R^{35}$;

$R^{30a}$ in each occurrence is independently selected from H and $C_{1-6}$alkyl, wherein $C_{1-6}$alkyl is optionally substituted with one to three $R^{35}$;

$R^{35}$ in each occurrence is independently selected from halo and —O$R^{35a}$; and $R^{35a}$ in each occurrence is independently selected from H and $C_{1-6}$alkyl, wherein the values of the other variables are as defined for the first, fifth, sixth, seventh, eighth, ninth, tenth, eleventh, twelfth, thirteenth, fourteenth, fifteenth, sixteenth, seventeenth, eighteenth, and nineteenth embodiments.

In a twenty-first embodiment of the invention, the compound is represented by the formula (I), (II), (III), or (IV), wherein $R^3$ in each occurrence is independently selected from $C_{1-4}$alkyl, —CN, halo, C(O)$_2$$R^{3a}$, C(O)N($R^{3a}$)$_2$, —N($R^{3a}$)$_2$, cyclopropyl, cyclobutyl, and —C(O)$R^{3a}$, wherein said $C_{1-4}$alkyl, cyclopropyl and cyclobutyl are optionally substituted with one to three groups selected from halo, N($R^{30a}$)$_2$, —CN, —S(O)$_2$$R^{30a}$, —C(O)N($R^{3a}$)$_2$, and —O$R^{3a}$;

$R^{3a}$ in each occurrence is independently selected from H, $C_{1-4}$alkyl, and azetidinyl, wherein said $C_{1-4}$alkyl and azetidinyl are optionally substituted with —O$R^{30a}$, N($R^{30a}$)$_2$, —CN, —S(O)$_2$$R^{30a}$, —C(O)$_2$$R^{30a}$, and —C(O)N($R^{30a}$)$_2$; and $R^{30a}$ in each occurrence is independently selected from H and $C_{1-4}$alkyl, wherein the values of the other variables are as defined for the first, fifth, sixth, seventh, eighth, ninth, tenth, eleventh, twelfth, thirteenth, fourteenth, fifteenth, sixteenth, seventeenth, eighteenth, nineteenth and twentieth embodiments.

In a twenty-second embodiment of the invention, the compound is represented by the formula (I), (II), (III), or (IV), $R^3$ is selected from $C_{1-4}$alkyl and cyclopropyl, each of which is optionally substituted with one to three groups selected from halo, —O$R^{3a}$, and —CN; and $R^{3a}$ in each occurrence is independently selected from H and $C_{1-4}$alkyl wherein the values of the other variables are as defined for the first, fifth, sixth, seventh, eighth, ninth, tenth, eleventh, twelfth, thirteenth, fourteenth, fifteenth, sixteenth, seventeenth, eighteenth, nineteenth, twentieth and twenty-first embodiments.

In a twenty-third embodiment of the invention, the compound is represented by the formula (I), (II), (III), or (IV), wherein the compound is represented by the formula structural formula

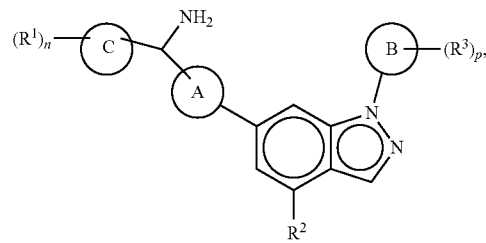

or a pharmaceutically acceptable salt thereof, wherein $R^1$ is F, OH or —$CH_2OH$;

Ring C is cyclobutyl or cyclopentyl;
Ring A is pyridinyl or pyrazinyl;
Ring B is pyridinyl, pyrazinyl, or pyrimidinyl;
$R^2$ is H or —O$R^{2a}$;
$R^{2a}$ is H or $C_{1-4}$alkyl, wherein the $C_{1-4}$alkyl is optionally substituted with one to three halo;
$R^3$ is $C_{1-4}$alkyl or ($C_3$-$C_6$)cycloalkyl, wherein said $C_{1-4}$alkyl or ($C_3$-$C_6$)cycloalkyl is optionally substituted with one to three groups independently selected from halo, —O$R^{3a}$ or —CN and
$R^{3a}$ in each occurrence is independently selected form H and $C_{1-4}$alkyl.

In a twenty-fourth embodiment of the invention, the invention is any one the compounds disclosed in the Exemplification section as a neutral compound or a pharmaceutically acceptable salt thereof.

In a twenty-fifth embodiment of the invention, there is provided a compound selected from:

cis-(S)-(6-(6-(6-(amino(3-(hydroxymethyl)cyclobutyl) methyl)pyridin-2-yl)-1H-indazol-1-yl)pyridin-2-yl) methanol;
(R)-(6-(6-(6-(amino(3-(hydroxymethyl)cyclobutyl)methyl) pyridin-2-yl)-1H-indazol-1-yl)pyridin-2-yl)methanol;
trans-(S)-(6-(6-(6-(amino(3-(hydroxymethyl)cyclobutyl) methyl)pyridin-2-yl)-1H-indazol-1-yl)pyridin-2-yl) methanol;
cis-3-((S)-amino(6-(1-(6-(hydroxymethyl)pyridin-2-yl)-1H-indazol-6-yl)pyridin-2-yl)methyl)cyclobutanol;
(6-(6-(6-((R)-amino((cis-3-(tert-butyldimethylsilyloxy)cyclobutyl)methyl)pyridin-2-yl)-1H-indazol-1-yl)pyridin-2-yl)methanol;
trans-3-((S)-amino(6-(1-(6-(hydroxymethyl)pyridin-2-yl)-1H-indazol-6-yl)pyridin-2-yl)methyl)cyclobutanol;
trans-3-((R)-amino(6-(1-(6-(hydroxymethyl)pyridin-2-yl)-1H-indazol-6-yl)pyridin-2-yl)methyl)cyclobutanol;
(1R,3S)-3-((S)-amino(6-(1-(4-(hydroxymethyl)pyrimidin-2-yl)-1H-indazol-6-yl)pyridin-2-yl)methyl)cyclobutanol;
cis 3-((S)-amino(6-(1-(6-(hydroxymethyl)pyrazin-2-yl)-1H-indazol-6-yl)pyridin-2-yl)methyl)cyclobutanol;
(1R,3S)-3-((S)-amino(6-(1-(6-(trifluoromethyl)pyridin-2-yl)-1H-indazol-6-yl)pyridin-2-yl)methyl)cyclobutanol;
(1R,3S)-3-((S)-amino(6-(1-(4-ethylpyrimidin-2-yl)-1H-indazol-6-yl)pyridin-2-yl)methyl)cyclobutanol;
(1R,3S)-3-((S)-amino(6-(1-(6-ethylpyridin-2-yl)-1H-indazol-6-yl)pyridin-2-yl)methyl)cyclobutanol;
(1R,3s)-3-((S)-amino(6-(1-(4-(trifluoromethyl)pyrimidin-2-yl)-1H-indazol-6-yl)pyridin-2-yl)methyl)cyclobutanol;
cis-3-((S)-amino(6-(1-(6-(difluoromethyl)pyridin-2-yl)-1H-indazol-6-yl)pyridin-2-yl)methyl)cyclobutanol;
(1R,3s)-3-((S)-amino(6-(1-(6-ethylpyrazin-2-yl)-1H-indazol-6-yl)pyridin-2-yl)methyl)cyclobutanol;
(1R,3s)-3-((S)-amino(6-(1-(6-(fluoromethyl)pyridin-2-yl)-1H-indazol-6-yl)pyridin-2-yl)methyl)cyclobutanol;

cis-3-((S)-amino(6-(1-(6-(hydroxymethyl)pyridin-2-yl)-1H-indazol-6-yl)pyrazin-2-yl)methyl)cyclobutanol;
cis-3-((S)-amino(6-(1-(6-(fluoromethyl)pyridin-2-yl)-1H-indazol-6-yl)pyrazin-2-yl)methyl)cyclobutanol;
cis-3-((S)-amino(6-(1-(6-(trifluoromethyl)pyridin-2-yl)-1H-indazol-6-yl)pyrazin-2-yl)methyl)cyclobutanol;
1-(6-(6-(6-((S)-amino(cis-3-hydroxycyclobutyl)methyl)pyridin-2-yl)-1H-indazol-1-yl)pyridin-2-yl)cyclopropanecarbonitrile;
3-(amino(6-(1-(6-(hydroxymethyl)pyridin-2-yl)-1H-indazol-6-yl)pyridin-2-yl)methyl)cyclopentanol;
(1R,3s)-3-((S)-amino(6-(4-(2,2-difluoroethoxy)-1-(6-(hydroxymethyl)pyridin-2-yl)-1H-indazol-6-yl)pyridin-2-yl)methyl)cyclobutanol;
(1R,3s)-3-((1S)-amino(6-(1-(4-(1-hydroxyethyl)pyrimidin-2-yl)-1H-indazol-6-yl)pyridin-2-yl)methyl)cyclobutanol;
(S)-(6-(6-(6-(amino(3,3-difluorocyclobutyl)methyl)pyridin-2-yl)-1H-indazol-1-yl)pyridin-2-yl) methanol;
(R)-(6-(6-(6-(amino(3,3-difluorocyclobutyl)methyl)pyridin-2-yl)-1H-indazol-1-yl)pyridin-2-yl) methanol;
(S)-(2-(6-(6-(amino(3,3-difluorocyclobutyl)methyl)pyridin-2-yl)-1H-indazol-1-yl)pyrimidin-4-yl) methanol;
(S)-(3,3-difluorocyclobutyl)(6-(1-(6-(fluoromethyl)pyridin-2-yl)-1H-indazol-6-yl)pyridin-2-yl)methanamine;
(S)-(3,3-difluorocyclobutyl)(6-(1-(6-(difluoromethyl)pyridin-2-yl)-1H-indazol-6-yl)pyridin-2-yl) methanamine;
(S)-(6-(6-(6-(amino(1-fluorocyclobutyl)methyl)pyridin-2-yl)-1H-indazol-1-yl)pyridin-2-yl) methanol;
(R)-(6-(6-(6-(amino(1-fluorocyclobutyl)methyl)pyridin-2-yl)-1H-indazol-1-yl)pyridin-2-yl) methanol;
(R)-(6-(6-(6-(amino(3,3-difluorocyclobutyl)methyl)pyridin-2-yl)-4-ethoxy-1H-indazol-1-yl)pyridin-2-yl)methanol;
(S)-(6-(6-(6-(amino(3,3-difluorocyclobutyl)methyl)pyridin-2-yl)-4-ethoxy-1H-indazol-1-yl)pyridin-2-yl)methanol;
3-((S)-amino(6-(1-(6-(difluoromethyl)pyridin-2-yl)-1H-indazol-6-yl)pyridin-2-yl)methyl)cyclobutan-1-ol;
3-((S)-amino(6-(1-(6-ethylpyridin-2-yl)-1H-indazol-6-yl)pyridin-2-yl)methyl)cyclobutan-1-ol;
(R)-(6-(6-(6-(amino(1-fluorocyclobutyl)methyl)pyridin-2-yl)-1H-indazol-1-yl)pyridin-2-yl) methanol;
(S)-(6-(6-(6-(amino(1-fluorocyclobutyl)methyl)pyridin-2-yl)-1H-indazol-1-yl)pyridin-2-yl) methanol;
(S)-3-(amino(6-(1-(6-methoxypyridin-2-yl)-1H-indazol-6-yl)pyridin-2-yl)methyl)cyclobutan-1-ol;
3-((S)-amino(6-(1-(6-(fluoromethyl)pyridin-2-yl)-1H-indazol-6-yl)pyridin-2-yl)methyl)-1-methylcyclobutan-1-ol;
3-((S)-amino(6-(1-(6-(difluoromethyl)pyridin-2-yl)-1H-indazol-6-yl)pyridin-2-yl)methyl)-1-methylcyclobutan-1-ol;
(S)-(6-(1-(6-(difluoromethyl)pyridin-2-yl)-1H-indazol-6-yl)pyridin-2-yl)(3-methoxycyclobutyl)methanamine;
3-((S)-amino(6-(1-(6-(fluoromethyl)pyridin-2-yl)-1H-indazol-6-yl)pyridin-2-yl)methyl)-1-methylcyclobutan-1-ol;
(S)-(6-(1-(6-(difluoromethyl)pyridin-2-yl)-1H-indazol-6-yl)pyridin-2-yl)((1R,3S)-3-methoxycyclobutyl)methanamine;
(S)-(6-(1-(6-(fluoromethyl)pyridin-2-yl)-1H-indazol-6-yl)pyridin-2-yl)(1-methylcyclobutyl)methanamine; and
(S)-3-(amino(6-(1-(6-(fluoromethyl)pyridin-2-yl)-1H-indazol-6-yl)pyridin-2-yl)methyl)cyclobutane-1-carbonitrile;
or a pharmaceutically acceptable salt thereof.

As used herein, the term "alkyl" refers to a fully saturated branched or unbranched hydrocarbon moiety. Preferably the alkyl comprises 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, or n-hexyl.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, isopropenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

The number of carbon atoms in a group is specified herein by the prefix "$C_{x-xx}$", wherein x and xx are integers. For example, "$C_{1-4}$alkyl" is an alkyl group which has from 1 to 4 carbon atoms.

"Halogen" or "halo" may be fluoro, chloro, bromo or iodo.

As used herein, the term "heterocyclyl" refers to a saturated or unsaturated, monocyclic or bicyclic (e.g., bridged or spiro ring systems) ring system which has from 3- to 7-ring members, or in particular 3- to 6-ring members or 5- to 7-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings. As used herein, the term "heteroaryl" refers to an aromatic 5- or 6-membered monocyclic ring system, having 1 to 4 heteroatoms independently selected from O, S and N, and wherein N can be oxidized (e.g., N(O)) or quaternized, and S can be optionally oxidized to sulfoxide and sulfone. In one embodiment, a heterocyclyl is a 3- to 7-membered saturated monocyclic or a 3- to 6-membered saturated monocyclic or a 5- to 7-membered saturated monocyclic ring. In one embodiment, a heterocyclyl is a 3- to 7-membered monocyclic or a 3- to 6-membered monocyclic or a 5- to 7-membered monocyclic ring. In another embodiment, a heterocyclyl is a 6 or 7-membered bicyclic ring. The heterocyclyl group can be attached at a heteroatom or a carbon atom. Examples of heterocyclyls include aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, and heteroaryl rings including azirinyl, oxirenyl, thiirenyl, diazirinyl, azetyl, oxetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl and the like. Examples of bicyclic heterocyclic ring systems include 3-azabicyclo[3.1.0]hexanyl, 3-azabicyclo[3.1.1]heptanyl, 2-azaspiro[3.3]heptanyl, 2-oxa-6-azaspiro[3.3]heptanyl, and 5-azaspiro[2.3]hexanyl.

As used herein, the term "carbocyclyl" refers to saturated or unsaturated monocyclic or bicyclic hydrocarbon groups of 3-7 carbon atoms, 3-6, or 5-7 carbon atoms. The term "carbocyclyl" encompasses cycloalkyl groups and aromatic groups. The term "cycloalkyl" refers to completely saturated monocyclic or bicyclic or spiro hydrocarbon groups of 3-7 carbon atoms, 3-6 carbon atoms, or 5-7 carbon atoms. Exemplary monocyclic carbocyclyl groups include, but are not limited to, cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, phenyl and cycloheptatrienyl. Exemplary bicyclic carbocyclyl groups include bicyclo[2.1.1]hexyl, bicyclo[2.2.1]heptyl, bicyclo[2.2.1]heptenyl, tricyclo[2.2.1.0$^{2,6}$]heptanyl, 6,6-dimethylbicyclo[3.1.1]heptyl, or 2,6,6-trimethylbicyclo[3.1.1]heptyl, spiro[2.2]pentanyl, and spiro[3.3]heptanyl.

The term "bridged ring system," as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system may have from 6-7 ring members.

The term "spiro ring system," as used herein, is a ring system that has two rings each of which are independently selected from a carbocyclyl or a heterocyclyl, wherein the two ring structures having one ring atom in common. Spiro ring systems have from 5 to 7 ring members.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, trimethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

The disclosed compounds, or pharmaceutically acceptable salts thereof, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). The disclosed compounds may exist in tautomeric forms and mixtures and separate individual tautomers are contemplated. In addition, some compounds may exhibit polymorphism.

The compounds or pharmaceutically acceptable salts thereof as described herein, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optic ally-active starting materials, by chiral synthesis, or chromatographic separation using a chiral stationary phase). When a particular enantiomer of a compound used in the disclosed methods is depicted by name or structure, the stereochemical purity of the compounds is at least 20%, 30%, 40%, 50%, 60%, 70%, 80%, 90%, 95%, 97%, 99%, 99.5% or 99.9%. "Stererochemical purity" means the weight percent of the desired stereoisomer relative to the combined weight of all stereoisomers.

Unless otherwise indicated, any position occupied by hydrogen is meant to include enrichment by deuterium or tritium above the natural abundance of deuterium or tritium as well. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance. The compounds or pharmaceutically acceptable salts thereof as described herein, may exist in tautomeric forms and mixtures and separate individual tautomers are contemplated.

Another embodiment is a pharmaceutical composition comprising at least one compound described herein, or a pharmaceutically acceptable salt thereof, and at least one pharmaceutically acceptable carrier.

The compounds, or pharmaceutically acceptable salts thereof described herein may be used to decrease the expression or activity of IRAK-4, or to otherwise affect the properties and/or behavior of IRAK-4 polypeptides or polynucleotides, e.g., stability, phosphorylation, kinase activity, interactions with other proteins, etc.

One embodiment of the invention includes a method of decreasing the expression or activity of IRAK-4, or to otherwise affect the properties and/or behavior of IRAK-4 polypeptides or polynucleotides comprising administering to said mammal an effective amount of at least one compound described herein, or a pharmaceutically acceptable salt thereof.

One embodiment of the invention includes a method for treating an inflammatory disease in a subject, the method comprising administering to the patient a therapeutically effective amount of a compound described herein, or a pharmaceutically acceptable salt thereof, thereby treating the inflammatory disease in the subject.

In one embodiment, the inflammatory disease is a pulmonary disease or a disease of the airway.

In one embodiment, the pulmonary disease and disease of the airway is selected from Adult Respiratory Disease Syndrome (ARDS), Chronic Obstructive Pulmonary Disease (OPD), pulmonary fibrosis, interstitial lung disease, asthma, chronic cough, and allergic rhinitis.

In one embodiment, the inflammatory disease is selected from transplant rejection, CD 14 mediated sepsis, non-CD 14 mediated sepsis, inflammatory bowel disease, Behcet's syndrome, ankylosing spondylitis, sarcoidosis, and gout. In particular, the inflammatory bowel disease is selected from Crohn's disease and ulcerative colitis.

One embodiment of the invention includes a method for treating an autoimmune disease, cancer, cardiovascular disease, a disease of the central nervous system, a disease of the skin, an ophthalmic disease and condition, and bone disease in a subject, the method comprising administering to the patient a therapeutically effective amount of a compound disclosed herein, or a pharmaceutically acceptable salt thereof, thereby treating the autoimmune disease, cancer, cardiovascular disease, disease of the central nervous system, disease of the skin, ophthalmic disease and condition, and bone disease in the subject.

In one embodiment, the autoimmune disease is selected from rheumatoid arthritis, systemic lupus erythematosus, multiple sclerosis, diabetes, systemic sclerosis, and Sjogren's syndrome.

In one embodiment, the autoimmune disease is type 1 diabetes.

In one embodiment, the cancer is selected from Waldenström's macroglobulinemia, solid tumors, skin cancer, and lymphoma.

In one embodiment, the cardiovascular disease is selected from stroke and atherosclerosis.

In one embodiment, the disease of the central nervous system is a neurodegenerative disease. In particular, the neurodegenerative disease is selected from Alzheimer's disease (AD), Parkinson's disease, Huntington's disease, and Amyotrophic lateral sclerosis (ALS).

Dementia is characterized by memory loss and other intellectual abilities of the patient serious enough to interfere with daily life. AD accounts for 60 to 80 percent of dementia cases. AD is a progressive disease and the dementia symptoms gradually worsen over a number of years. Survival rates for AD patients can range from four to 20 years, depending on age and other health conditions. AD has no current cure.

Increased IRAK-4 expression and activity has been found to be associated with AD. In particular, an immunohistochemical analysis revealed an increased presence of IRAK-4 in the astrocytes and microglia of post-mortem AD brain tissue as compared to post-mortem non-AD brain tissue indicating that IRAK-4 protein kinase activity is increased in AD patients. (See Hoozemans, J. J. M. el al, "Increased IRAK-4 Kinase Activity in Alzheimer's Disease; IRAK-1/4 Inhibitor I Prevents Pro-inflammatory Cytokine Secretion but not the Uptake of Amyloid Beta by Primary Human Glia", Clin Cell Immunol 2014, 5:4, the teachings of which are incorporated herein by reference.)

In vitro functional assays showed that an IRAK-1/4 inhibitor I reduced the lipopolysaccharide-induced secretion of monocyte chemotactic protein-1 (MCP-1) by primary human microglia and the interleukin-1β-induced secretion of MCP-1 and interleukin 6 by primary human astrocytes. In contrast, the in vitro uptake of amyloid β (Aβ) by astrocytes and microglia is not affected by IRAK-1/4 inhibition. Thus, selective inhibition of IRAK-1/4 inhibits a pro-inflammatory response without affecting the uptake of Aβ by glial cells, indicating that the IRAK signaling pathway is a potential target for modulating neuroinflammation in AD. (See Hoozemans, J. J. M. et al., "Increased IRAK-4 Kinase Activity in Alzheimer's Disease; IRAK-1/4 Inhibitor I Prevents Pro-inflammatory Cytokine Secretion but not the Uptake of Amyloid Beta by Primary Human Glia", Clin Cell Immunol 2014, 5:4, the teachings of which are incorporated herein by reference.)

The loss of microglial IRAK4 function blocks microglial inflammatory responses and the generation of reactive oxygen species in vitro. In an AD murine model that lacks any endogenous IRAK4 kinase activity, loss of IRAK4 function in vivo reduced amyloid burden at later ages, reduced gliosis, altered microglial phenotype including altered expression of interferon regulator factor (IRF) transcription factors, and restored normal behavior. Further, loss of IRAK4 function in vivo also promoted amyloid clearance mechanisms, including elevated expression of insulin-degrading enzyme, (see Cameron, B. et al., "Loss of Interleukin Receptor-Associated Kinase 4 Signaling Suppresses Amyloid Pathology and Alters Microglial Phenotype in a Mouse Model of Alzheimer's Disease," The Journal of Neuroscience, Oct. 24, 2012•32(43): 15112-15123, the teachings of which are incorporated herein by reference).

In one embodiment, the disease of the skin is selected from rash, contact dermatitis, psoriasis, and atopic dermatitis.

In one embodiment, the bone disease is selected from osteoporosis and osteoarthritis.

In one embodiment, the inflammatory bowel disease is selected from Crohn's disease and ulcerative colitis.

One embodiment of the invention includes a method for treating an ischemic fibrotic disease, the method comprising administering to the patient a therapeutically effective amount of a compound described herein, or a pharmaceutically acceptable salt thereof, thereby treating the ischemic fibrotic disease in the subject. In one embodiment, the ischemic fibrotic disease is selected from stroke, acute lung injury, acute kidney injury, ischemic cardiac injury, acute liver injury, and ischemic skeletal muscle injury.

One embodiment of the invention includes a method for treating post-organ transplantation fibrosis, the method comprising administering to the patient a therapeutically effective amount of a compound described herein, or a pharmaceutically acceptable salt thereof, thereby treating post-organ transplantation fibrosis in the subject.

One embodiment of the invention includes a method for treating hypertensive or diabetic end organ disease, the method comprising administering to the patient a therapeutically effective amount of a compound described herein, or a pharmaceutically acceptable salt thereof, thereby treating hypertensive or diabetic end organ disease in the subject.

One embodiment of the invention includes a method for treating hypertensive kidney disease, the method comprising administering to the patient a therapeutically effective amount of a compound described herein, or a pharmaceutically acceptable salt thereof, thereby treating hypertensive kidney disease in the subject.

One embodiment of the invention includes a method for treating idiopathic pulmonary fibrosis (IPF), the method comprising administering to the patient a therapeutically effective amount of a compound described herein, or a pharmaceutically acceptable salt thereof, thereby treating IPF in the subject.

One embodiment of the invention includes a method for treating scleroderma or systemic sclerosis, the method comprising administering to the patient a therapeutically effective amount of a compound described herein, or a pharmaceutically acceptable salt thereof, thereby treating scleroderma or systemic sclerosis in the subject.

One embodiment of the invention includes a method for treating liver cirrhosis, the method comprising administering to the patient a therapeutically effective amount of a compound described herein, or a pharmaceutically acceptable salt thereof, thereby treating liver cirrhosis in the subject.

One embodiment of the invention includes a method for treating fibrotic diseases wherein tissue injury and/or inflammation are present, the method comprising administering to the patient a therapeutically effective amount of a compound described herein, or a pharmaceutically acceptable salt thereof, thereby treating fibrotic diseases where tissue injury and/or inflammation are present in the subject. The fibrotic diseases include, for example, pancreatitis, peritonitis, burns, glomerulonephritis, complications of drug toxicity, and scarring following infections.

Scarring of the internal organs is a major global health problem, which is the consequence of subclinical injury to the organ over a period of time or as the sequela of acute severe injury or inflammation. All organs may be affected by scarring and currently there are few therapies the specifically target the evolution of scarring. Increasing evidence indicates that scarring per se provokes further decline in organ function, inflammation and tissue ischemia. This may be directly due the deposition of the fibrotic matrix which impairs function such as in contractility and relaxation of the heart and vasculature or impaired inflation and deflation of lungs, or by increasing the space between microvasculature and vital cells of the organ that are deprived of nutrients and distorting normal tissue architecture. However recent studies have shown that myofibroblasts themselves are inflammatory cells, generating cytokines, chemokines and radicals that promote injury; and myofibroblasts appear as a result of a transition from cells that normally nurse and maintain the microvasculature, known as pericytes. The consequence of this transition of phenotype is an unstable microvasculature that leads to aberrant angiogenesis, or rarefaction.

The present disclosure relates to methods and compositions for treating, preventing, and/or reducing scarring in organs. More particularly, the present disclosure relates to methods and composition for treating, preventing, and/or reducing scarring in kidneys.

It is contemplated that the present disclosure, methods and compositions described herein can be used as an antifibrotic, or used to treat, prevent, and/or reduce the severity and damage from fibrosis.

It is additionally contemplated that the present disclosure, methods and compositions described herein can be used to treat, prevent, and/or reduce the severity and damage from fibrosis.

It is further contemplated that the present disclosure, methods and compositions described herein can used as an anti-inflammatory, used to treat inflammation.

Some non-limiting examples of organs include: kidney, hearts, lungs, stomach, liver, pancreas, hypothalamus, stomach, uterus, bladder, diaphragm, pancreas, intestines, colon, and so forth.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or "treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The dose of a compound provided herein, or a pharmaceutically acceptable salt thereof, administered to a subject can be 10 µg-500 mg; 10 µg to 1 mg; or 1 to 500 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmuco sally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmuco sally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The a compound or pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

Example 1. (S)-(6-(6-(6-(amino(3-(hydroxymethyl)cyclobutyl)methyl)pyridin-2-yl)-1H-indazol-1-yl)pyridin-2-yl)methanol Step 1. Synthesis of methyl 3-methylenecyclobutanecarboxylate

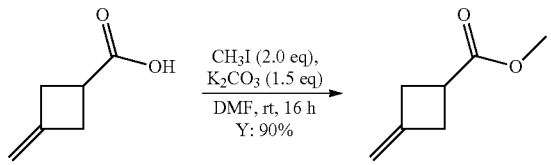

To a mixture of 3-methylenecyclobutanecarboxylic acid (4 g, 35.7 mmol, 1.0 eq) and $K_2CO_3$ (7.4 g, 53.5 mmol, 1.5 eq) in DMF (50 mL) was added $CH_3I$ (10.1 g, 71.4 mmol, 2.0 eq). The reaction mixture was stirred at rt for 16 h. The mixture was diluted with $Et_2O$ (100 mL) and washed with water (50 mL×3). The organic phase was dried over $Na_2SO_4$. After filtration and concentration, 4.04 g of methyl 3-methylenecyclobutanecarboxylate as yellow oil was obtained. Y: 90%. ESI-MS $(M+H)^+$: 127.0. $^1H$ NMR (400 MHz, $CDCl_3$) δ: 4.82-4.79 (m, 2H), 3.70 (s, 3H), 3.13-3.11 (m, 1H), 3.09-2.97 (m, 2H), 2.94-2.89 (m, 2H).

Step 2. Synthesis of methyl 3-(hydroxymethyl)cyclobutanecarboxylate

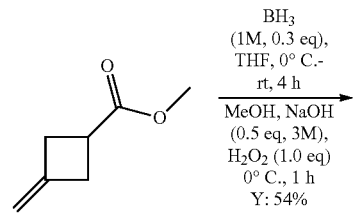

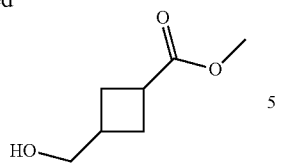

To a solution of methyl 3-methylenecyclobutanecarboxylate (5.3 g, 42.4 mmol, 1.0 eq) in THF (30 mL) was added $BH_3$ (12.6 mL, 12.6 mmol, 0.3 eq, 1 M) dropwise at 0° C. Then the reaction mixture was warmed to rt and stirred for 4 h. MeOH (15 mL) was added and the mixture was stirred for 30 min at 0° C. NaOH (4.2 mL, 3M) and $H_2O_2$ (1.4 g, 42.4 mmol, 1.0 eq) were added and stirred at 0° C. for 1 h. The mixture was quenched with water (30 mL) and extracted with $Et_2O$ (60 mL×2). The combined organic phases were dried over $Na_2SO_4$. After filtration and concentration, 3.3 g of methyl 3-(hydroxymethyl)cyclobutanecarboxylate as yellow oil was obtained. Y: 54%. ESI-MS (M+H)$^+$: 145.0. $^1$H NMR (400 MHz, $CD_3OD$) δ: 3.69 (s, 1.3H), 3.67 (s, 1.7H), 3.59 (s, 0.4H), 3.58 (s, 0.5H), 3.50 (s, 0.4H), 3.48 (s, 0.5H), 3.12-3.03 (m, 1H), 2.48-2.38 (m, 1H), 2.35-2.22 (m, 2H), 2.08-1.94 (m, 2H).

Step 3. Synthesis of methyl 3-((tert-butyldimethylsilyloxy)methyl)cyclobutanecarboxylate

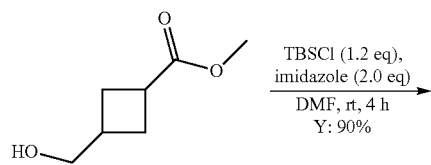

To a mixture of methyl 3-(hydroxymethyl)cyclobutanecarboxylate (3.3 g, 22.9 mmol, 1.0 eq) and imidazole (3.1 g, 45.8 mmol, 2.0 eq) in DMF (50 mL) was added TBSCl (4.1 g, 27.5 mmol, 1.2 eq). The mixture was stirred at rt for 4 h. Then the mixture was diluted with EA (100 mL) and washed with water (100 mL×3). The combined organic phases were dried over $Na_2SO_4$. After filtration and concentration, the residue was purified by silica gel chromatography with PE/EA (10/1) as eluent to give methyl 3-((tert-butyldimethylsilyloxy)methyl)cyclobutanecarboxylate as yellow oil (5.3 g, Y: 90%). ESI-MS (M+H)$^+$: 259.1. $^1$H NMR (400 MHz, $CDCl_3$) δ: 3.68 (s, 1.3H), 3.66 (s, 1.7H), 3.60 (s, 0.4H), 3.59 (s, 0.4H), 3.53 (s, 0.5H), 3.51 (s, 0.5H), 3.10-3.06 (m, 0.4H), 3.03-2.94 (m, 0.6H), 2.51-2.28 (m, 1H), 2.34-2.24 (m, 1H), 2.20-2.17 (m, 1H), 2.08-2.00 (m, 2H), 0.87 (s, 4H), 0.85 (s, 5H), 0.04 (s, 2.5H), 0.03 (s, 3.5H).

Step 4. Synthesis of (6-bromopyridin-2-yl)(3-((tert-butyldimethylsilyloxy)methyl)cyclobutyl)methanone

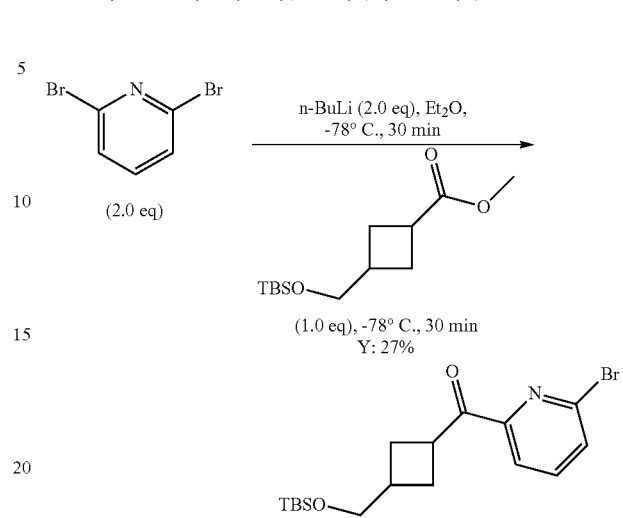

To a solution of 2,6-dibromopyridine (9.8 g, 42 mmol, 2.0 eq) in $Et_2O$ (200 mL) was added n-BuLi (16.8 mL, 42 mmol, 2.0 eq, 2.5 M) dropwise at −78° C. The mixture was stirred at −78° C. for 30 min. Then methyl 3-((tert-butyldimethylsilyloxy)methyl)cyclobutanecarboxylate (5.3 g, 10.5 mmol, 1.0 eq) was added at −78° C. and the mixture was stirred for 30 min. Then the mixture was quenched with $NH_4Cl$ (sat.). The mixture was extracted with EA (200 mL×2). The combined organic phases were dried over $Na_2SO_4$. After filtration and concentration, the residue was purified by silica gel chromatography with PE/EA (20/1) as eluent to give (6-bromopyridin-2-yl)(3-((tert-butyldimethylsilyloxy)methyl)cyclobutyl)methanone as yellow oil (2.1 g, Y: 27%). ESI-MS (M+H)$^+$: 384.1.

Step 5. Synthesis of (R,E)-N-((6-bromopyridin-2-yl)(3-((tert-butyldimethylsilyloxy)methyl)cyclobutyl)methylene)-2-methylpropane-2-sulfinamide (P1 and P2)

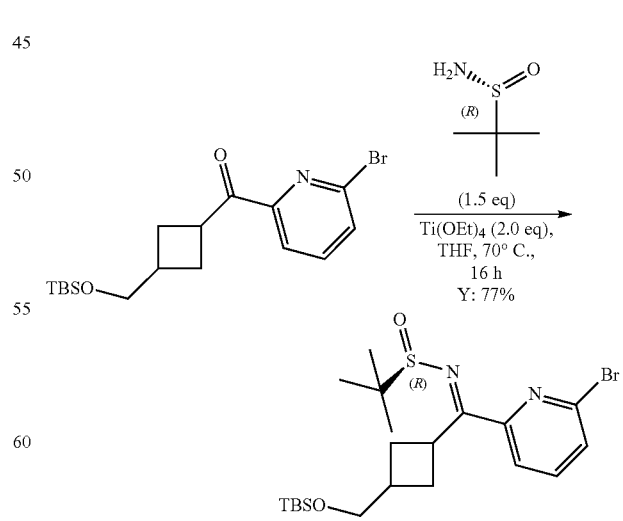

To a mixture of (6-bromopyridin-2-yl)(3-((tert-butyldimethylsilyloxy)methyl)cyclobutyl)methanone (2.1 g, 5.48 mmol, 1.0 eq) and (R)-2-methylpropane-2-sulfinamide (995 mg, 8.22 mmol, 1.5 eq) in THF (50 mL) was added Ti(OEt)₄ (3.10 g, 10.96 mmol, 2.0 eq). The reaction mixture was stirred at 70° C. for 16 h. After concentration, the residue was purified by silica gel chromatography with PE/EA (20/1) as eluent to give (R,E)-N-((6-bromopyridin-2-yl)(3-((tert-butyldimethylsilyloxy)methyl)cyclobutyl)methylene)-2-methylpropane-2-sulfinamide (P1) (400 mg, Y: 31%) as yellow oil and (R,E)-N-((6-bromopyridin-2-yl)(3-((tert-butyldimethylsilyloxy)methyl)cyclobutyl)methylene)-2-methylpropane-2-sulfinamide (P2) (600 mg, Y: 46%) as yellow oil. ESI-MS (M+H)⁺: 487.2.

Step 6. Synthesis of (R)—N—((S)-(6-bromopyridin-2-yl)(3-((tert-butyldimethylsilyloxy)methyl)cyclobutyl)methyl)-2-methylpropane-2-sulfinamide (P2) and (R)—N—((R)-(6-bromopyridin-2-yl)(3-((tert-butyldimethylsilyloxy)methyl)cyclobutyl)methyl)-2-methylpropane-2-sulfinamide (P2)

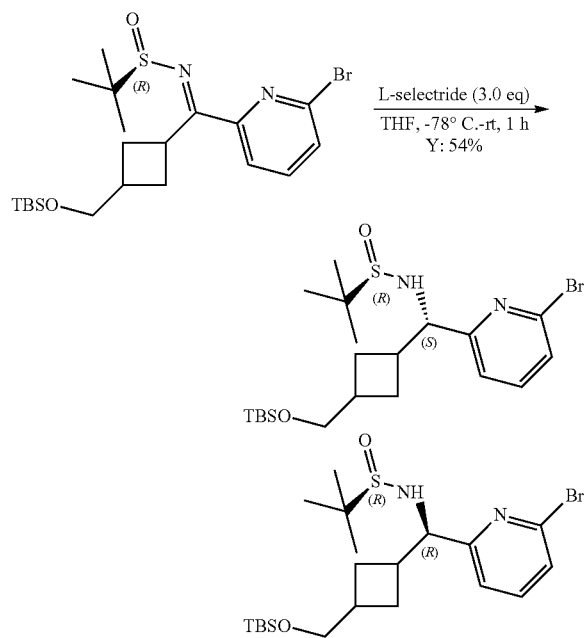

To a solution of (R,E)-N-((6-bromopyridin-2-yl)(3-((tert-butyldimethylsilyloxy)methyl)cyclobutyl)methylene)-2-methylpropane-2-sulfinamide (P2) (600 mg, 1.23 mmol, 1.0 eq) in THF (15 mL) was added L-selectride (3.69 mL, 3.0 eq, 1M) dropwise at −78° C. Then the mixture was warmed to rt and stirred for 1 h. Then the mixture was quenched with NH₄Cl (sat.). The mixture was extracted with EA (20 mL×2). The combined organic phases were dried over Na₂SO₄. After filtration and concentration, the residue was purified by silica gel chromatography with PE/EA (8/1) as eluent to give (R)—N—((S)-(6-bromopyridin-2-yl)(3-((tert-butyldimethylsilyloxy)methyl)cyclobutyl)methyl)-2-methylpropane-2-sulfinamide (P2) as a white solid (235 mg, Y: 36%) and (R)—N—((R)-(6-bromopyridin-2-yl)(3-((tert-butyldimethylsilyloxy)methyl)cyclobutyl)methyl)-2-methylpropane-2-sulfinamide (P2) (120 mg, Y: 18%) as a yellow solid. ESI-MS (M+H)⁺: 489.2.

Step 7. Synthesis of (6-(6-bromo-1H-indazol-1-yl)pyridin-2-yl)methanol

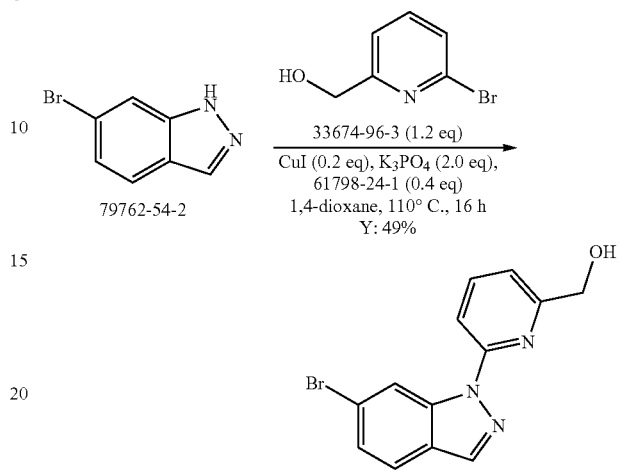

A mixture of 6-bromo-1H-indazole (79762-54-2) (3.2 g, 16.3 mmol, 1.0 eq), (6-bromopyridin-2-yl)methanol (33674-96-3) (3.66 g, 19.6 mmol, 1.2 eq), CuI (620 mg, 3.26 mmol, 0.2 eq), K₃PO₄ (6.9 g, 32.6 mmol, 2.0 eq) and N,N'-Dimethyl-cyclohexane-1,2-diamine (61798-24-1) (930 mg, 6.52 mmol, 0.4 eq) in 1,4-dioxane (50 mL) was stirred at 110° C. for 16 h. After concentration, the residue was purified by silica gel chromatography using PE/EA (3/1) as eluent to give (6-(6-bromo-1H-indazol-1-yl)pyridin-2-yl)methanol as a yellow solid. 2.42 g, Y: 49%. ESI-MS (M+H)⁺: 304.1.

Step 8. Synthesis of 6-bromo-1-(6-(((tert-butyldimethylsilyl)oxy)methyl)pyridin-2-yl)-1H-indazole

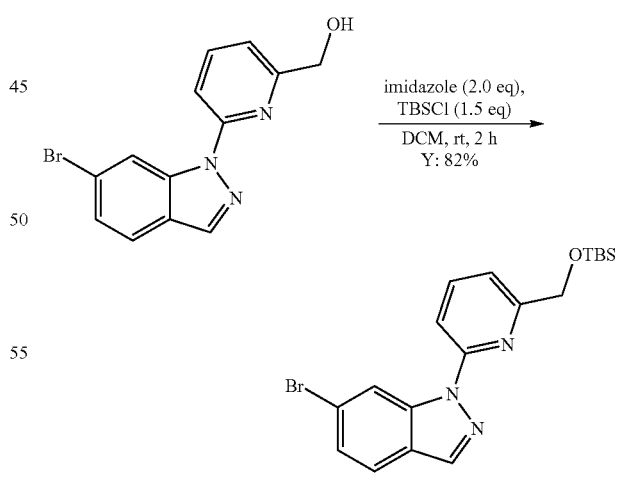

To a solution of (6-(6-bromo-1H-indazol-1-yl)pyridin-2-yl)methanol (2.42 g, 8.0 mmol, 1.0 eq) in DCM (50 mL) was added TBSCl (1.8 g, 12.0 mmol, 1.5 eq), imidazole (1.09 g, 16.0 mmol, 2.0 eq). The mixture was stirred at rt for 2 h. After filtration, the filtrate was concentrated and purified by silica gel chromatography using PE/EA (5/1) as eluent to give 6-bromo-1-(6-(((tert-butyldimethylsilyl)oxy)methyl)pyridin-2-yl)-1H-indazole. 2.73 g, as a white solid, Y: 82%. ESI-MS (M+H)⁺: 418.1.

Step 9. Synthesis of 1-(6-(((tert-butyldimethylsilyl)oxy)methyl)pyridin-2-yl)-6-(4,4,5,5-tetramethyl-1,3,2-dioxaborolan-2-yl)-1H-indazole

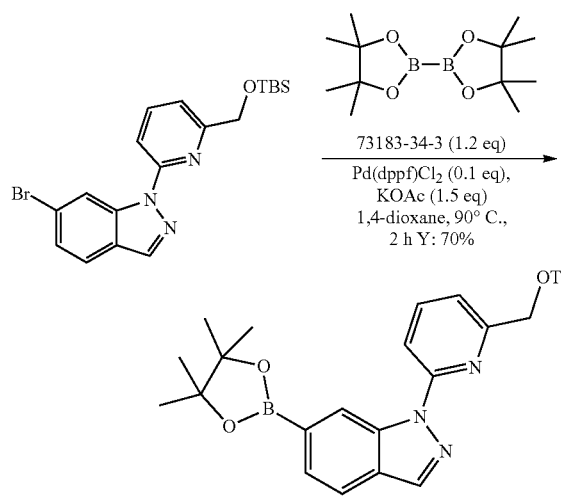

A mixture of 6-bromo-1-(6-(((tert-butyldimethylsilyl)oxy)methyl)pyridin-2-yl)-1H-indazole (834 mg, 2.0 mmol, 1.0 eq), 4,4,4',4',5,5,5',5'-octamethyl-2,2'-bi(1,3,2-dioxaborolane) (73183-34-3) (610 mg, 2.4 mmol, 1.2 eq) and CH₃COOK (294 mg, 3.0 mmol, 1.5 eq) in 1,4-dioxane (20 mL) was stirred while purging N₂ at rt for 10 min. To this system was added Pd(dppf)Cl₂ (180 mg, 0.2 mmol, 0.1 eq) and heated to 90° C. for 2 h. The mixture was diluted with EA (50 mL), washed with and brine (50 mL) and was dried over Na₂SO₄. After filtration and concentration, the residue was purified by silica gel chromatography using PE/EA (5/1) as eluent to give 1-(6-(((tert-butyldimethylsilyl)oxy)methyl)pyridin-2-yl)-6-(4,4,5,5-tetramethyl-1,3,2-dioxaborolan-2-yl)-1H-indazole. 651 mg, as a white solid, Y: 70%. ESI-MS (M+H)⁺: 466.2.

Step 10. Synthesis of (R)—N—((S)-(3-((tert-butyldimethylsilyloxy)methyl)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide (P2)

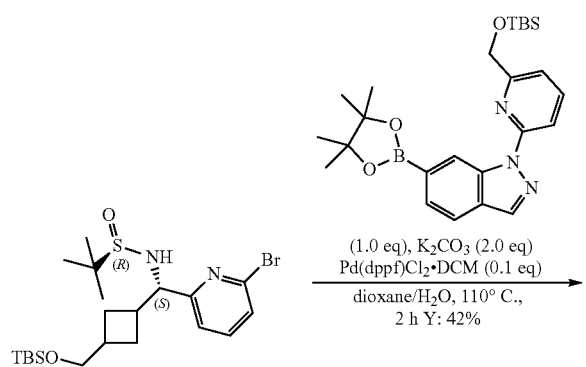

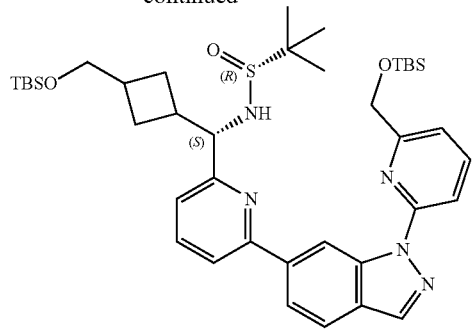

To a reaction mixture of (R)—N—((S)-(6-bromopyridin-2-yl)(3-((tert-butyldimethylsilyloxy)methyl)cyclobutyl)methyl)-2-methylpropane-2-sulfinamide (P2) (Step 6) (235 mg, 0.48 mmol, 1.0 eq), 1-(6-(((tert-butyldimethylsilyl)oxy)methyl)pyridin-2-yl)-6-(4,4,5,5-tetramethyl-1,3,2-dioxaborolan-2-yl)-1H-indazole (246 mg, 0.48 mmol, 1.0 eq) and K₂CO₃ (133 mg, 0.96 mmol, 2.0 eq) in dioxane (4 mL) and H₂O (0.3 mL) was added Pd(dppf)Cl₂ (40 mg, 0.04 mmol, 0.1 eq). The reaction mixture was stirred at 110° C. for 2 h under N₂. After concentration, the residue was purified by silica gel chromatography with PE/EA (2/1) as eluent to give (R)—N—((S)-(3-((tert-butyldimethylsilyloxy)methyl)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide (P2) as yellow oil (163 mg, Y: 42%). ESI-MS (M+H)⁺: 748.4

Step 11. Synthesis of (S)-(6-(6-(6-(amino(3-(hydroxymethyl)cyclobutyl)methyl)pyridin-2-yl)-1H-indazol-1-yl)pyridin-2-yl)methanol (P2, HCl)

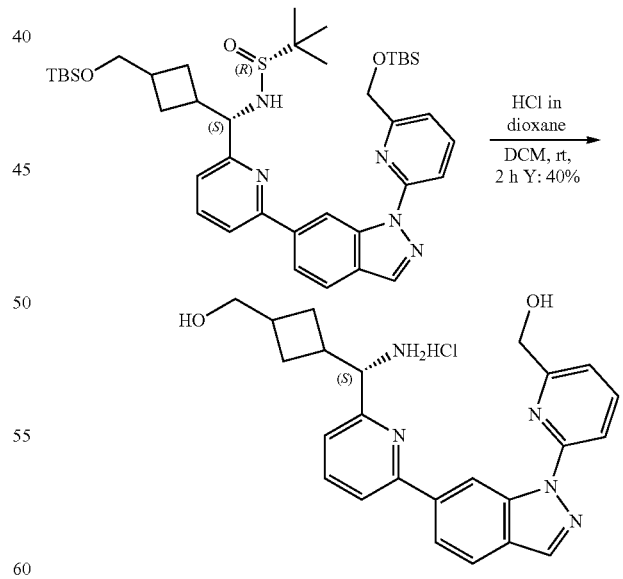

To a solution of (R)—N—((S)-(3-((tert-butyldimethylsilyloxy)methyl)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide (P2) (165 mg, 0.22 mmol, 1.0 eq) in DCM (5 mL) was added HCl in dioxane (1 mL, 4M). The mixture was stirred at rt for 2 h. After filtration, 70 mg of (S)-(6-(6-(6-(amino(3-(hydroxymethyl)cyclobutyl)methyl)pyridin-2-yl)-1H-indazol-1-yl)pyridin-2-yl)methanol (P2, HCl) as a white solid was obtained. Y: 70%. ESI-MS (M+H)+: 416.2. HPLC: 100% ¹H NMR (400 MHz, CD₃OD) δ: 9.60 (s, 1H), 8.35 (s, 1H), 8.13-7.94 (m, 6H), 7.47 (d, J=7.6 Hz, 1H), 7.40 (d, J=6.8 Hz, 1H), 4.93 (s, 2H), 4.50-4.47 (m, 1H), 3.50 (d, J=5.6 Hz, 2H), 2.83-2.77 (m, 1H), 2.44-2.31 (m, 2H), 1.96-1.78 (m, 3H).

Example 2 (R)-(6-(6-(6-(amino(3-(hydroxymethyl)cyclobutyl)methyl)pyridin-2-yl)-1H-indazol-1-yl)pyridin-2-yl)methanol Step 1. Synthesis of (R)—N—((R)-(3-((tert-butyldimethylsilyloxy)methyl)cyclobutyl)(6-(1-(6-(((tert-butyldimethylsilyloxy)methyl)pyridin-2-yl)-1H-indazol-6-yl)pyridin-2-yl)methyl)-2-methylpropane-2-sulfinamide (P2)

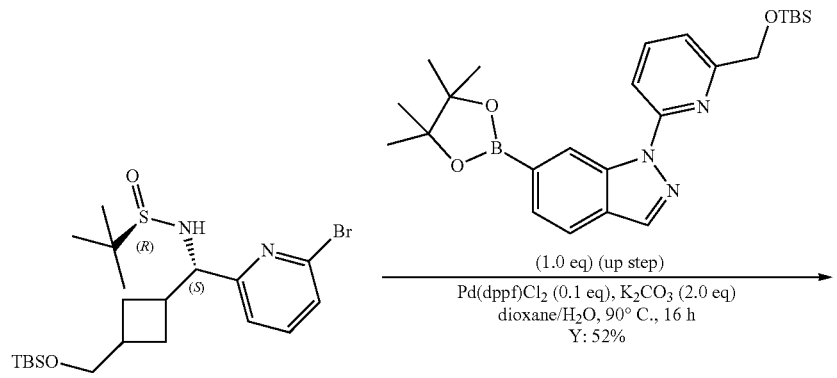

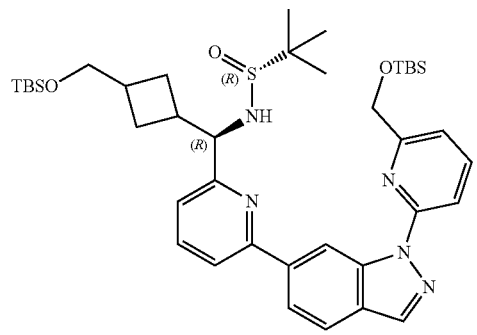

The preparation of (R)—N—((R)-(3-((tert-butyldimethylsilyloxy)methyl)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide (P2) was similar to that of (R)—N—((S)-(3-((tert-butyldimethylsilyloxy)methyl)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide (P2) (Example 1, Step 10) to give 95 mg as yellow oil, Y: 52%. ESI-MS (M+H)+: 748.4.

Step 2. Synthesis of (R)-(6-(6-(6-(amino(3-(hydroxymethyl)cyclobutyl)methyl)pyridin-2-yl)-1H-indazol-1-yl)pyridin-2-yl)methanol (P2, HCl)

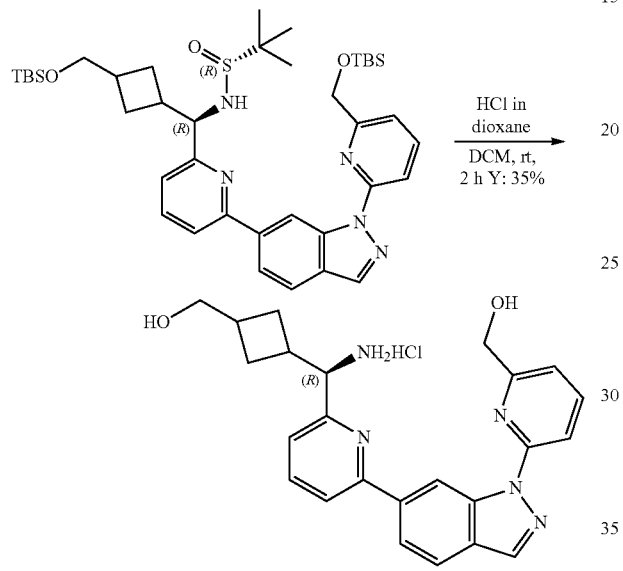

The preparation of (R)-(6-(6-(6-(amino(3-(hydroxymethyl)cyclobutyl)methyl)pyridin-2-yl)-1H-indazol-1-yl)pyridin-2-yl)methanol (P2, HCl) was similar to that of (S)-(6-(6-(6-(amino(3-(hydroxymethyl)cyclobutyl)methyl)pyridin-2-yl)-1H-indazol-1-yl)pyridin-2-yl)methanol (P2, HCl) (Example 1, Step 11) to give 20 mg as a yellow solid, Y: 35%. ESI-MS (M+H)+: 416.2. HPLC: 80% $^1$H NMR (400 MHz, CD$_3$OD) δ: 9.60 (s, 1H), 8.39 (s, 1H), 8.15-8.00 (m, 6H), 7.49 (d, J=7.6 Hz, 1H), 7.44 (d, J=6.8 Hz, 1H), 4.92 (s, 2H), 4.50-4.48 (m, 1H), 3.51 (d, J=5.6 Hz, 2H), 2.84-2.78 (m, 1H), 2.46-2.30 (m, 2H), 1.98-1.79 (m, 3H).

Example 3 (S)-(6-(6-(6-(amino(3-(hydroxymethyl)cyclobutyl)methyl)pyridin-2-yl)-1H-indazol-1-yl)pyridin-2-yl)methanol Step 1. Synthesis of (R)—N—((S)-(6-bromopyridin-2-yl)(3-((tert-butyldimethylsilyloxy)methyl)cyclobutyl)methyl)-2-methylpropane-2-sulfinamide (P1)

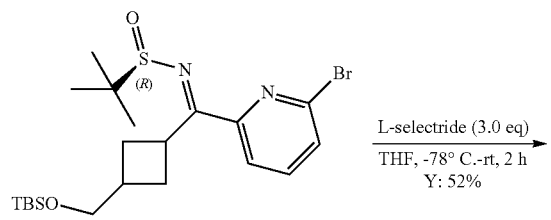

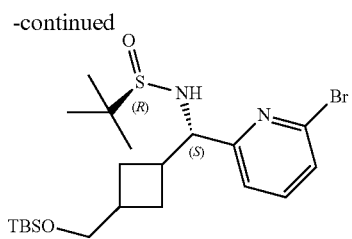

The preparation of (R)—N—((S)-(6-bromopyridin-2-yl)(3-((tert-butyldimethylsilyloxy)methyl)cyclobutyl)methyl)-2-methylpropane-2-sulfinamide (P1) was similar to that of (R)—N—((S)-(6-bromopyridin-2-yl)(3-((tert-butyldimethylsilyloxy)methyl)cyclobutyl)methyl)-2-methylpropane-2-sulfinamide (P2) and (R)—N—((R)-(6-bromopyridin-2-yl)(3-((tert-butyldimethylsilyloxy)methyl)cyclobutyl)methyl)-2-methylpropane-2-sulfinamide (P2) (Example 1, Step 6) to give 250 mg of the title compound as yellow oil, Y: 52%, and a smaller amount of (R)—N—((R)-(6-bromopyridin-2-yl)(3-((tert-butyldimethylsilyloxy)methyl)cyclobutyl)methyl)-2-methylpropane-2-sulfinamide (P1). ESI-MS (M+H)+: 489.2.

Step 2. Synthesis of (R)—N—((S)-(3-((tert-butyldimethylsilyloxy)methyl)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide (P1)

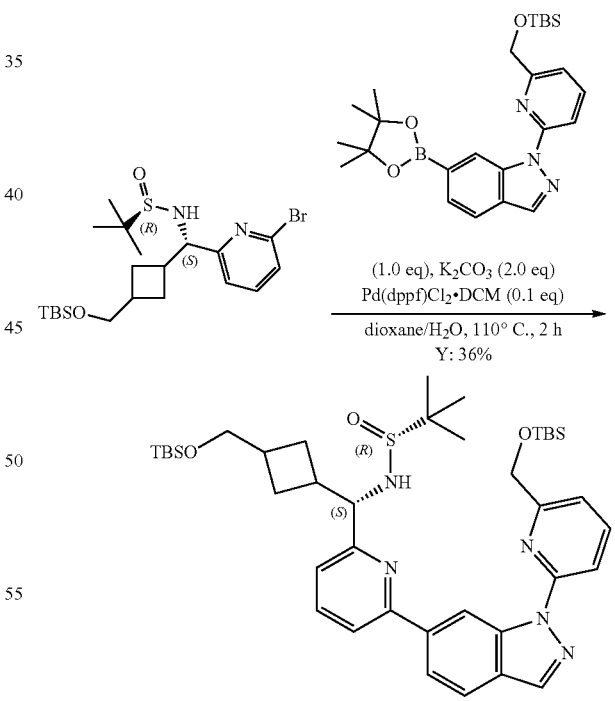

The preparation of (R)—N—((S)-(3-((tert-butyldimethylsilyloxy)methyl)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide (P1) was similar to that of (R)—N—((S)-(3-((tert-butyldimethylsilyloxy)methyl)cyclobutyl)(6-(1-(6-((tert-butyldimethylsilyloxy)methyl)pyridin-2-yl)-1H-indazol-6-yl)pyridin-2-yl)methyl)-

2-methylpropane-2-sulfinamide (P2) (Example 1, Step 10) to give 200 mg as yellow oil. Y: 36%. ESI-MS (M+H)+: 748.4

Step 3. Synthesis of (S)-(6-(6-(6-(amino(3-(hydroxymethyl)cyclobutyl)methyl)pyridin-2-yl)-1H-indazol-1-yl)pyridin-2-yl)methanol (P1, HCl)

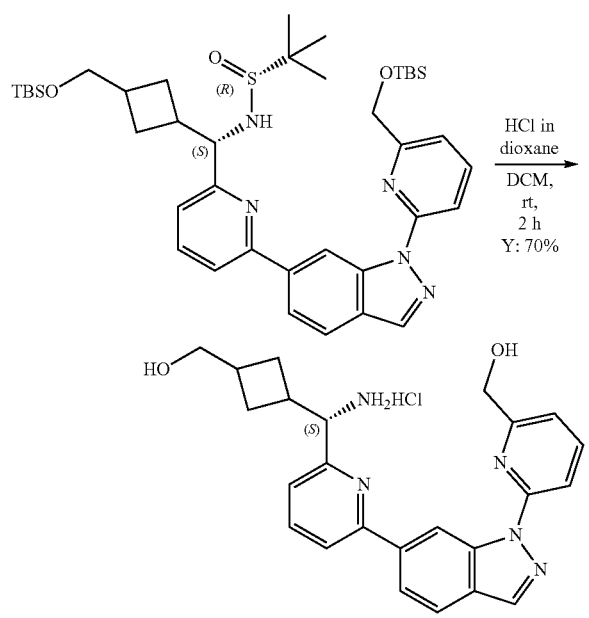

The preparation of (S)-(6-(6-(6-(amino(3-(hydroxymethyl)cyclobutyl)methyl)pyridin-2-yl)-1H-indazol-1-yl) pyridin-2-yl)methanol (P1, HCl) was similar to that of (S)-(6-(6-(6-(amino(3-(hydroxymethyl)cyclobutyl)methyl) pyridin-2-yl)-1H-indazol-1-yl)pyridin-2-yl)methanol (P2, HCl) (Example 1, Step 11) to give 19 mg as a yellow solid. Y: 70%. ESI-MS (M+H)+: 416.2. HPLC: 100% $^1$H NMR (400 MHz, CD$_3$OD) δ: 9.56 (s, 1H), 8.38 (s, 1H), 8.14-8.04 (m, 5H), 7.98 (d, J=8.4 Hz, 1H), 7.53 (d, J=7.6 Hz, 1H), 7.43 (d, J=6.8 Hz, 1H), 4.91 (s, 2H), 4.63-4.60 (m, 1H), 3.60 (d, J=6.8 Hz, 2H), 3.00-2.93 (m, 1H), 2.46-2.42 (m, 1H), 2.31-2.26 (m, 1H), 2.19-2.10 (m, 2H), 1.82-1.76 (m, 1H).

Example 4 cis-3-((S)-amino(6-(1-(6-(hydroxymethyl)pyridin-2-yl)-1H-indazol-6-yl)pyridin-2-yl)methyl)cyclobutanol Step 1. Synthesis of cis-methyl 3-hydroxycyclobutanecarboxylate

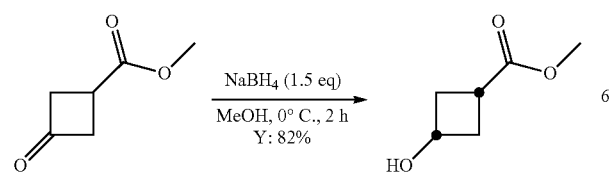

To a solution of methyl 3-oxocyclobutanecarboxylate (15 g, 117.2 mmol) in MeOH was added NaBH$_4$ (6.7 g, 175.8 mmol) at 0° C. The mixture was stirred at 0° C. for 2 h. The solvent was removed and the residue was diluted with water (100 mL), extracted with EA (100 mL×3). The combined organic layers were washed with brine (100 mL) and dried over Na$_2$SO$_4$. After filtration and concentration, 12.5 g of cis-methyl 3-hydroxycyclobutanecarboxylate was obtained as colorless oil, which was used in the next step without further purification. Y: 82%. ESI-MS (M+H)+: 131.1. $^1$H NMR (400 MHz, CDCl$_3$) δ: 4.20-4.19 (m, 1H), 3.69 (s, 3H), 2.64-2.56 (m, 3H), 2.24-2.14 (m, 3H).

Step 2. Synthesis of (cis-methyl 3-(tert-butyldimethylsilyloxy)cyclobutanecarboxylate

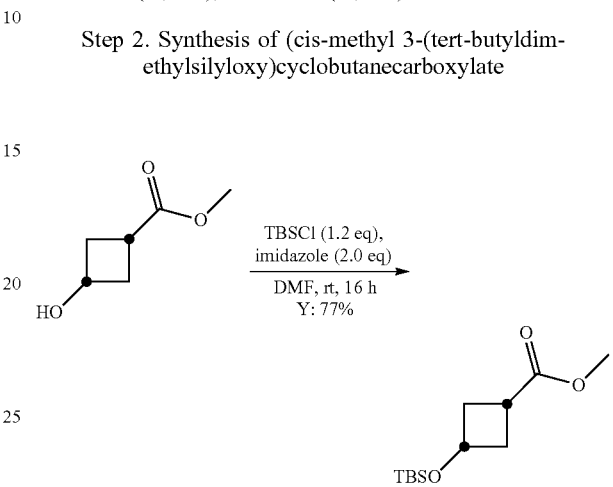

To a solution of cis-methyl 3-hydroxycyclobutanecarboxylate (12 g, 92.3 mmol) in DMF (150 mL) were added imidazole (12.6 g, 184.6 mmol) and TBSCl (16.6 g, 110.8 mmol). The mixture was stirred at rt for 16 h. The mixture was diluted with water (300 mL) and extracted with ethyl acetate (100 mL×3). The combined organic layers were washed with brine, dried, evaporated and purified by silica gel chromatography with PE/EA (50/1) as eluent to give cis-methyl 3-(tert-butyldimethylsilyloxy)cyclobutanecarboxylate (17 g, Y: 77%) as colorless oil. ESI-MS (M+H)+: 245.1. $^1$H NMR (400 MHz, CDCl$_3$) δ: 4.11-4.09 (m, 1H), 3.64 (s, 3H), 2.50-2.42 (m, 3H), 2.18-2.14 (m, 2H), 0.84 (s, 9H), 0.05 (s, 6H).

Step 3. Synthesis of (6-bromopyridin-2-yl)(cis-3-(tert-butyldimethylsilyloxy)cyclobutyl)methanone

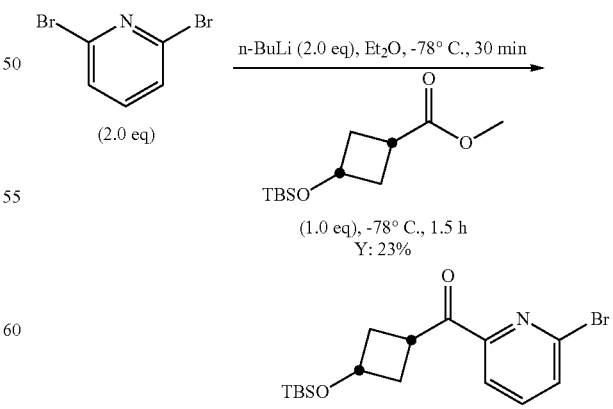

To a solution of 2,6-dibromopyridine (8.3 g, 35 mmol, 1.0 eq) in dry ether (150 mL) at −78° C. was added n-BuLi (2.5 M, 14 mL, 35 mmol, 1.0 eq) dropwise. The mixture was stirred at −78° C. for 30 min and then cis-methyl 3-(tert-butyldimethylsilyloxy)cyclobutanecarboxylate (8.5 g, 35 mmol, 1.0 eq) was added. The mixture was stirred at this temperature for further 1.5 h, quenched with sat. NH$_4$Cl, extracted with EA (50 mL×3). The combined organic fractions were washed with brine, dried, evaporated and purified by silica gel chromatography with PE/EA (20/1) as eluent to give (6-bromopyridin-2-yl)(cis-3-(tert-butyldimethylsilyloxy)cyclobutyl)methanone as colorless oil. 3.0 g, Y: 23%, ESI-MS (M+H)$^+$: 370.1, 372.1. $^1$H NMR (400 MHz, CDCl$_3$) δ: 8.01-7.99 (m, 1H), 7.70-7.62 (m, 2H), 4.39-4.31 (m, 1H), 3.90-3.81 (m, 1H), 2.62-2.54 (m, 2H), 2.26-2.16 (m, 2H), 0.89 (s, 9H), 0.06 (s, 6H).

Step 4. Synthesis of (R)—N-((6-bromopyridin-2-yl)((cis-3-(tert-butyldimethylsilyloxy)cyclobutyl)methylene)-2-methylpropane-2-sulfinamide To a solution of (R)-(+)-2-methyl-2-propanesulfinamide (1.18 g, 9.76 mmol, 1.2 eq) and (6-bromopyridin-2-yl)(cis-3-(tert-butyldimethylsilyloxy)cyclobutyl)methanone (3.0 g, 8.13 mmol, 1.0 eq) in THF (100 mL) was added Ti(OEt)$_4$ (5.3 g, 16.26 mmol, 2.0 eq). The mixture was stirred at 60° C. for 16 h. After concentration, the residue was purified by silica gel chromatography with PE/EA (3/1) as eluent to afforded (R)—N-((6-bromopyridin-2-yl)(cis-3-(tert-butyldimethylsilyloxy)cyclobutyl)methylene)-2-methylpropane-2-sulfinamide (1.2 g, Y: 31%) as yellow oil and (R)—N-((6-bromopyridin-2-yl)(3-(tert-butyldimethylsilyloxy)cyclobutylidene)methyl)-2-methylpropane-2-sulfinamide (900 mg, Y: 23%) as yellow oil. ESI-MS (M+H)$^+$: 473.1, 475.1. $^1$H NMR (400 MHz, CDCl$_3$) δ: 7.60-7.48 (m, 3H), 4.18-4.13 (m, 1H), 3.61-3.16 (m, 1H), 2.59-2.56 (m, 2H), 2.21-2.14 (m, 2H), 1.27 (s, 9H), 0.88 (s, 9H), 0.04 (s, 6H).

Step 5. Synthesis of (R)—N—((S)-(6-bromopyridin-2-yl)(cis-3-(tert-butyldimethylsilyloxy)cyclobutyl)methyl)-2-methylpropane-2-sulfinamide and (R)—N—((R)-(6-bromopyridin-2-yl)(cis-3-(tert-butyldimethylsilyloxy)cyclobutyl)methyl)-2-methylpropane-2-sulfinamide

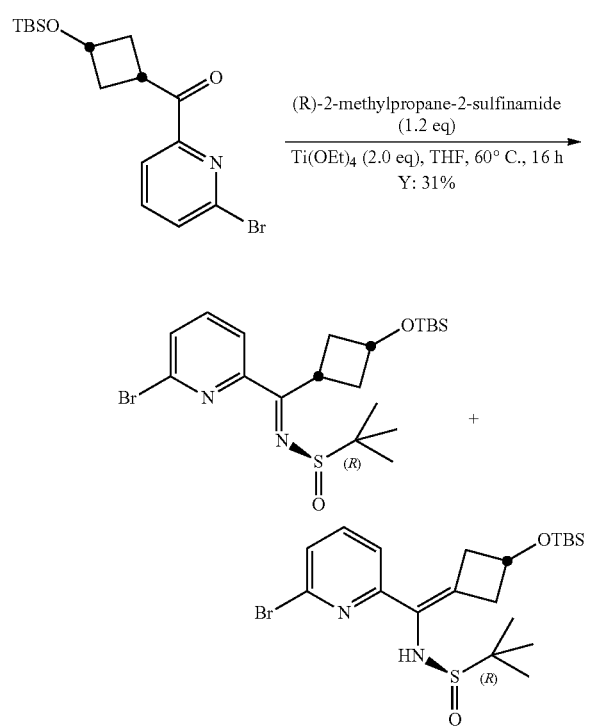

To a solution of (R)—N-((6-bromopyridin-2-yl)(cis-3-(tert-butyldimethylsilyloxy)cyclobutyl)methylene)-2-methylpropane-2-sulfinamide (1.2 g, 2.54 mmol, 1.0 eq) in dry THF (50 mL) was added L-Selectride (1.0 M in THF, 7.6 mL, 7.63 mmol, 3.0 eq) at −78° C. Then the mixture was stirred at −78° C. for 2 h. The reaction was quenched with saturated NH$_4$Cl solution and dried over Na$_2$SO$_4$. After filtration and concentration, the residue was purified by silica gel chromatography with PE/EA (5/1) as eluent to give (R)—N—((S)-(6-bromopyridin-2-yl)(cis-3-(tert-butyldimethylsilyloxy)cyclobutyl)methyl)-2-methylpropane-2-sulfinamide (550 mg, Y: 46%) as a white solid and (R)—N—((R)-(6-bromopyridin-2-yl)(cis-3-(tert-butyldimethylsilyloxy)cyclobutyl)methyl)-2-methylpropane-2-sulfinamide (380 mg, Y: 32%) as a white solid. ESI-MS (M+H)$^+$: 475.1, 477.1.

(R)—N—((S)-(6-bromopyridin-2-yl)(cis-3-(tert-butyldimethylsilyloxy)cyclobutyl)methyl)-2-methylpropane-2-sulfinamide: $^1$H NMR (400 MHz, CDCl$_3$) δ: 7.49 (t, J=7.6 Hz, 1H), 7.36 (dd, J=8.0 Hz, 0.8 Hz, 1H), 7.17 (dd, J=8.0 Hz, 0.8 Hz, 1H), 4.31-4.27 (m, 1H), 4.10-4.03 (m, 1H), 3.89-3.88 (m, 1H), 2.59-2.50 (m, 1H), 2.23-2.16 (m, 1H), 2.09-2.04 (m, 1H), 1.90-1.83 (m, 1H), 1.73-1.62 (m, 1H), 1.17 (s, 9H), 0.86 (s, 9H), 0.02 (s, 6H).

(R)—N—((R)-(6-bromopyridin-2-yl)(cis-3-(tert-butyldimethylsilyloxy)cyclobutyl)methyl)-2-methylpropane-2-sulfinamide: $^1$H NMR (400 MHz, CDCl$_3$) δ: 7.50-7.46 (m, 1H), 7.36-7.34 (m, 1H), 7.19-7.17 (m, 1H), 4.61-4.59 (m, 1H), 4.31-4.17 (m, 1H), 4.08-4.05 (m, 1H), 2.39-2.31 (m, 1H), 2.15-2.05 (m, 2H), 1.83-1.76 (m, 2H), 1.26 (s, 9H), 0.87 (s, 9H), 0.02 (s, 6H).

Step 6. Synthesis of (R)—N—((S)-(cis-3-(tert-butyldimethylsilyloxy)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide

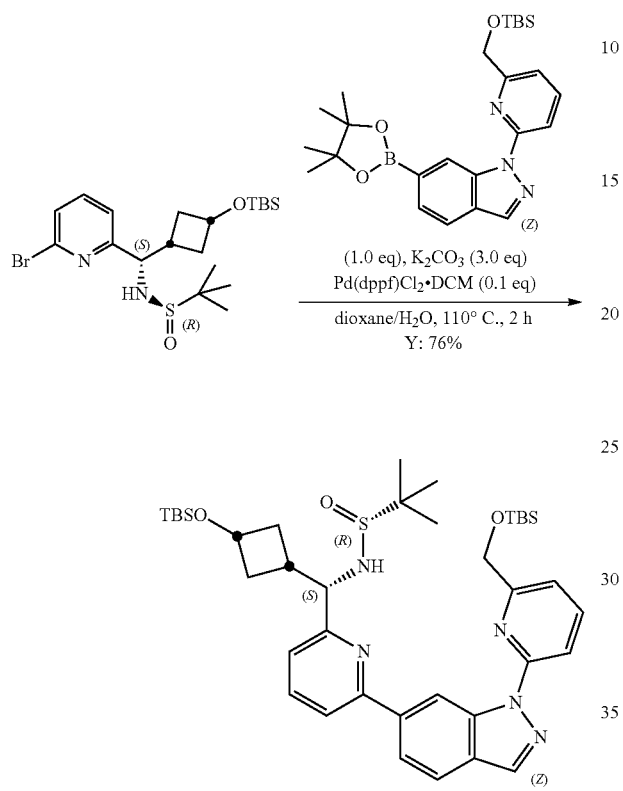

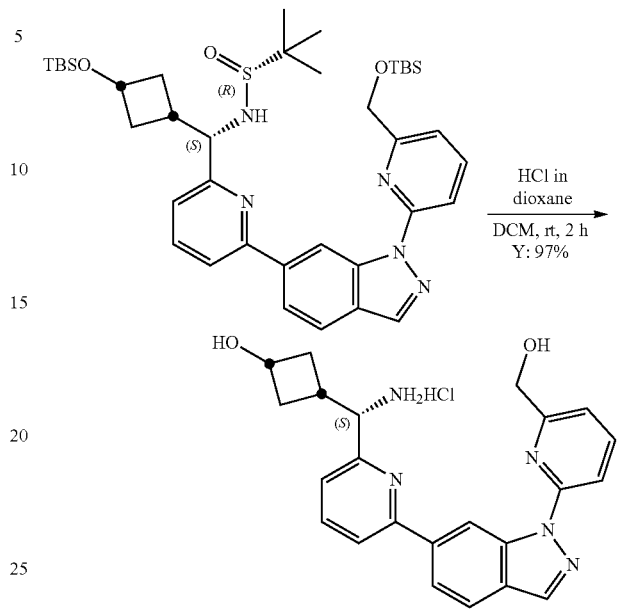

To a solution of (R)—N—((S)-(6-bromopyridin-2-yl)((cis-3-(tert-butyldimethylsilyloxy)cyclobutyl)methyl)-2-methylpropane-2-sulfinamide (220 mg, 0.46 mmol, 1.0 eq) and 1-(6-(((tert-butyldimethylsilyl)oxy)methyl)pyridin-2-yl)-6-(4,4,5,5-tetramethyl-1,3,2-dioxaborolan-2-yl)-1H-indazole (Example 1, Step 9, 216 mg, 0.46 mmol, 1.0 eq) in 1,4-dioxane/H$_2$O (20/1, 21 mL) were added Pd(dppf)Cl$_2$·DCM (38 mg, 0.046 mmol, 0.1 eq) and K$_2$CO$_3$ (192 mg, 1.39 mmol, 3.0 eq). The mixture was stirred at 110° C. under N$_2$ for 2 h. After cooling to rt, the mixture was diluted with water (100 mL) and extracted with EA (30 mL×3). The combined organic fractions were washed with brine, dried and evaporated. The residue was purified by pre-TLC (PE/EA=1/1) to give (R)—N—((S)-(cis-3-(tert-butyldimethylsilyloxy)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide (260 mg, Y: 76%) as a white solid. ESI-MS (M+H)$^+$: 734.4. $^1$H NMR (400 MHz, CDCl$_3$) δ: 9.33 (s, 1H), 8.22 (s, 1H), 8.08-8.06 (m, 1H), 7.93-7.84 (m, 3H), 7.79-7.74 (m, 2H), 7.41-7.39 (m, 1H), 7.20-7.17 (m, 1H), 4.97 (s, 2H), 4.44-4.40 (m, 1H), 4.29-4.27 (m, 1H), 4.12-4.05 (m, 1H), 2.65-2.59 (m, 1H), 2.32-2.26 (m, 1H), 2.14-2.05 (m, 1H), 1.98-1.92 (m, 1H), 1.84-1.77 (m, 1H), 1.17 (s, 9H), 0.99 (s, 9H), 0.86 (s, 9H), 0.17 (s, 6H), 0.02 (s, 6H).

Step 7. Synthesis of cis-3-((S)-amino(6-(1-(6-(hydroxymethyl)pyridin-2-yl)-1H-indazol-6-yl)pyridin-2-yl)methyl)cyclobutanol (HCl)

To a solution of (R)—N—((S)-(cis-3-(tert-butyldimethylsilyloxy)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide (260 mg, 0.355 mmol) in DCM (10 mL) was added HCl/dioxane (4 M, 1 mL) at rt. The mixture was stirred at rt for 1 h. The precipitate was filtered and washed with DCM, dried in vacuo to give cis-3-((S)-amino(6-(1-(6-(hydroxymethyl)pyridin-2-yl)-1H-indazol-6-yl)pyridin-2-yl)methyl)cyclobutanol (HCl) (150 mg, Y: 97%) as a yellow solid. ESI-MS (M+H)$^+$: 402.2, HPLC: 100%. $^1$H NMR (400 MHz, CD$_3$OD) δ: 9.75 (s, 1H), 8.35 (s, 1H), 8.15-8.09 (m, 2H), 8.03-7.96 (m, 4H), 7.45-7.38 (m, 2H), 4.94 (s, 2H), 4.49-4.47 (m, 1H), 4.16-4.13 (m, 1H), 2.65-2.59 (m, 1H), 2.42-2.28 (m, 1H), 2.27-2.22 (m, 1H), 1.97-1.86 (m, 2H).

Example 5. (6-(6-(6-((R)-amino((cis-3-(tert-butyldimethylsilyloxy)cyclobutyl)methyl)pyridin-2-yl)-1H-indazol-1-yl)pyridin-2-yl)methanol Step 1. Synthesis of (R)—N—((R)-(cis-3-(tert-butyldimethylsilyloxy)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide

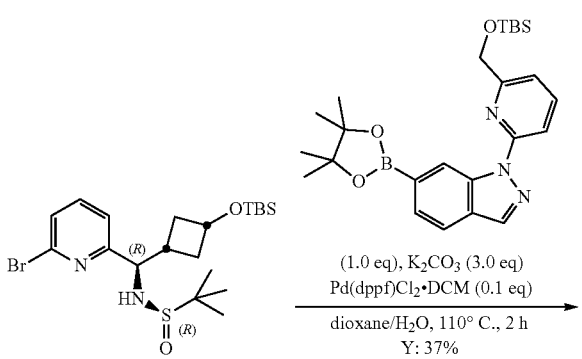

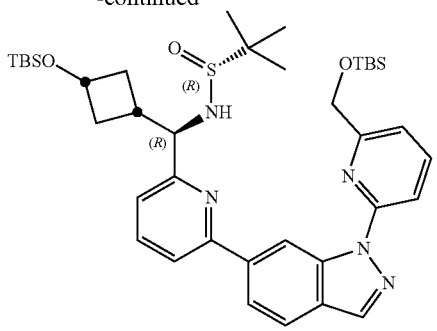

The preparation of (R)—N—((R)-(cis-3-(tert-butyldimethylsilyloxy)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide was similar to that of (R)—N—((S)-(3-((tert-butyldimethylsilyloxy)methyl)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide (P2) (Example 1, Step 10) to give 110 mg as a white solid. Y: 37%. ESI-MS (M+H)+: 734.4. $^1$H NMR (400 MHz, CDCl$_3$) δ: 9.29 (s, 1H), 8.22 (s, 1H), 8.02-8.00 (m, 1H), 7.93-7.83 (m, 3H), 7.79-7.74 (m, 2H), 7.41-7.39 (m, 1H), 7.22-7.20 (m, 1H), 5.26-5.25 (m, 1H), 4.96 (s, 2H), 4.41-4.37 (m, 1H), 4.13-4.08 (m, 1H), 2.38-2.33 (m, 1H), 2.21-2.14 (m, 2H), 1.95-1.85 (m, 2H), 1.29 (s, 9H), 0.99 (s, 9H), 0.88 (s, 9H), 0.17 (s, 6H), 0.02 (s, 6H).

Step 2. Synthesis of (cis)-3-((R)-amino(6-(1-(6-(hydroxymethyl)pyridin-2-yl)-1H-indazol-6-yl)pyridin-2-yl)methyl)cyclobutan-1-ol hydrochloride

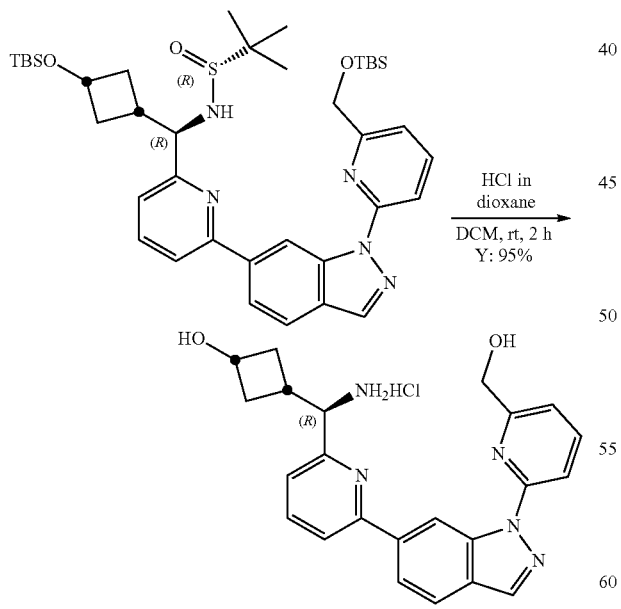

The preparation of (6-(6-(6-((R)-amino(cis-3-(tert-butyldimethylsilyloxy)cyclobutyl)methyl)pyridin-2-yl)-1H-indazol-1-yl)pyridin-2-yl)methanol (HCl) was similar to that of (S)-(6-(6-(6-(amino(3-(hydroxymethyl)cyclobutyl)methyl)pyridin-2-yl)-1H-indazol-1-yl)pyridin-2-yl)methanol (P2, HCl) (Example 1, Step 11) to give 65 mg as a yellow solid. Y: 95%. ESI-MS (M+H)+: 402.2. $^1$H NMR (400 MHz, CD$_3$OD) δ: 9.75 (s, 1H), 8.37-8.36 (m, 1H), 8.16-8.10 (m, 2H), 8.04-7.97 (m, 4H), 7.45-7.38 (m, 2H), 4.94 (s, 2H), 4.49-4.47 (m, 1H), 4.18-4.11 (m, 1H), 2.65-2.59 (m, 1H), 2.42-2.28 (m, 1H), 2.27-2.22 (m, 1H), 1.97-1.86 (m, 2H).

Example 6. trans-3-((S)-amino(6-(1-(6-(hydroxymethyl)pyridin-2-yl)-1H-indazol-6-yl)pyridin-2-yl)methyl)cyclobutanol Step 1. Synthesis of trans-methyl 3-(tert-butyldimethylsilyloxy)cyclobutanecarboxylate

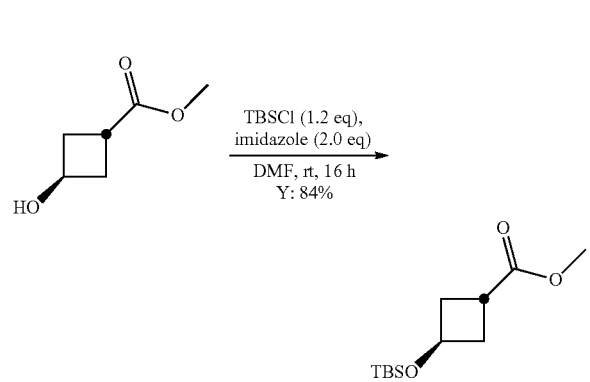

The preparation of tram-methyl 3-(tert-butyldimethylsilyloxy)cyclobutanecarboxylate was similar to that of methyl 3-((tert-butyldimethylsilyloxy)methyl)cyclobutanecarboxylate (Example 1, Step 3) to give 9.5 g as colorless oil, Y: 84%. ESI-MS (M+H)+: 245.1. $^1$H NMR (400 MHz, CDCl$_3$) δ: 4.53-4.50 (m, 1H), 3.69 (s, 3H), 2.98-2.93 (m, 1H), 2.53-2.48 (m, 2H), 2.56-2.18 (m, 3H), 0.88 (s, 9H), 0.05 (s, 6H).

Step 2. Synthesis of (6-bromopyridin-2-yl)(trans-3-(tert-butyldimethylsilyloxy)cyclobutyl)methanone

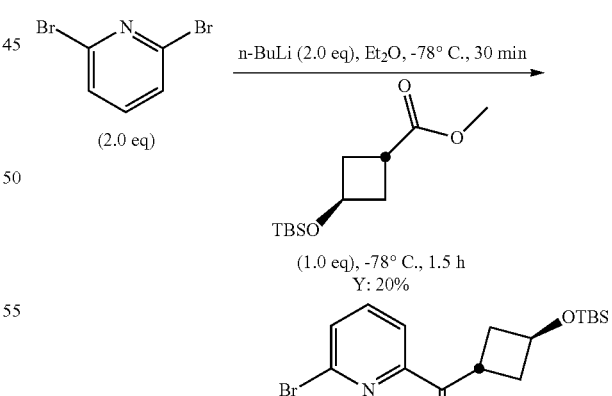

The preparation of (6-bromopyridin-2-yl)(trans-3-(tert-butyldimethylsilyloxy)cyclobutyl)methanone was similar to that of (6-bromopyridin-2-yl)(3-((tert-butyldimethylsilyloxy)methyl)cyclobutyl)methanone (Example 1, Step 4) to give 6.0 g as colorless oil, purity: 50%, Y: 20%. ESI-MS (M+H)+: 370.1.

Step 3. Synthesis of (R)—N-((6-bromopyridin-2-yl)(3-(tert-butyldimethylsilyloxy)cyclobutylidene)methyl)-2-methylpropane-2-sulfinamide

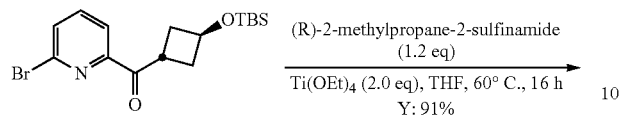

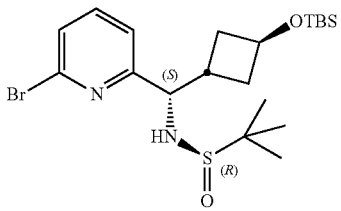

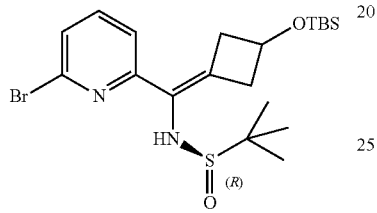

The preparation of (R)—N-((6-bromopyridin-2-yl)(3-(tert-butyldimethylsilyloxy)cyclobutylidene)methyl)-2-methylpropane-2-sulfinamide was similar to that of (R,E)-N-((6-bromopyridin-2-yl)(3-((tert-butyldimethylsilyloxy)methyl)cyclobutyl)methylene)-2-methylpropane-2-sulfinamide (Example 1, Step 5) (P1 and P2) to give 3.5 g as colorless oil, which was used in the Step 4 without further purification. Y: 91%. ESI-MS (M+H)+: 472.1, 474.1.

Step 4. Synthesis of (R)—N—((S)-(6-bromopyridin-2-yl)(trans-3-(tert-butyldimethylsilyloxy)cyclobutyl)methyl)-2-methylpropane-2-sulfinamide and (R)—N—((R)-(6-bromopyridin-2-yl)(trans-3-(tert-butyldimethylsilyloxy)cyclobutyl)methyl)-2-methylpropane-2-sulfinamide

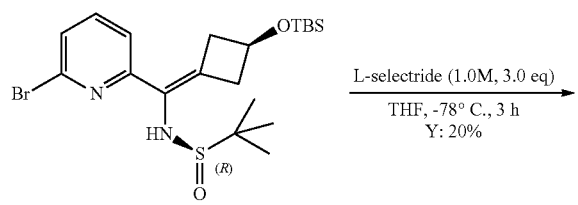

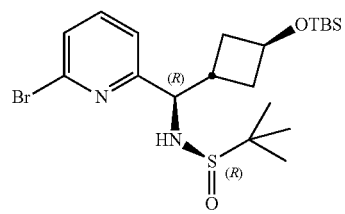

The preparation of (R)—N—((S)-(6-bromopyridin-2-yl)(trans-3-(tert-butyldimethylsilyloxy)cyclobutyl)methyl)-2-methylpropane-2-sulfinamide and (R)—N—((R)-(6-bromopyridin-2-yl)(trans-3-(tert-butyldimethylsilyloxy)cyclobutyl)methyl)-2-methylpropane-2-sulfinamide was similar to that of (R)—N-((6-bromopyridin-2-yl)(3-((tert-butyldimethylsilyloxy)methyl)cyclobutyl)methylene)-2-methylpropane-2-sulfinamide (P1 and P2, Example 1, Step 6) The residue was purified by chiral-HPLC (column: AS-H; Co-Solvent: IPA; Rt: (R)—N—((S)-(6-bromopyridin-2-yl)(trans-3-(tert-butyldimethylsilyloxy)cyclobutyl)methyl)-2-methylpropane-2-sulfinamide, 5.55 min, ((R)—N—((S)-(6-bromopyridin-2-yl)(trans-3-(tert-butyldimethylsilyloxy)cyclobutyl)methyl)-2-methylpropane-2-sulfinamide, 3.13 min) to give (R)—N—((S)-(6-bromopyridin-2-yl)(trans-3-(tert-butyldimethylsilyloxy)cyclobutyl)methyl)-2-methylpropane-2-sulfinamide (560 mg, Y: 16%) and ((R)—N—((R)-(6-bromopyridin-2-yl)(trans-3-(tert-butyldimethylsilyloxy)cyclobutyl)methyl)-2-methylpropane-2-sulfinamide (150 mg, Y: 4%) as white solid. ESI-MS (M+H)+: 475.1, 477.1.

(R)—N—((S)-(6-bromopyridin-2-yl)(trans-3-(tert-butyldimethylsilyloxy)cyclobutyl)methyl)-2-methylpropane-2-sulfinamide: $^1$H NMR (400 MHz, CDCl$_3$) δ: 7.51 (t, J=7.6 Hz, 1H), 7.37 (dd, J=7.6 Hz, 0.8 Hz, 1H), 7.20 (d, J=7.6 Hz, 1H), 4.38-4.31 (m, 2H), 3.75-3.73 (m, 1H), 2.68-2.64 (m, 1H), 2.40-2.35 (m, 1H), 2.19-2.06 (m, 2H), 1.99-1.95 (m, 1H), 1.16 (s, 9H), 0.86 (s, 9H), 0.02 (s, 6H).

(R)—N—((R)-(6-bromopyridin-2-yl)(trans-3-(tert-butyldimethylsilyloxy)cyclobutyl)methyl)-2-methylpropane-2-sulfinamide: $^1$H NMR (400 MHz, CDCl$_3$) δ: 7.49 (t, J=7.6 Hz, 1H), 7.35 (d, J=7.6 Hz, 1H), 7.19 (d, J=7.6 Hz, 1H), 4.34-4.31 (m, 1H), 4.23-4.20 (m, 1H), 2.64-2.59 (m, 1H), 2.31-2.26 (m, 1H), 2.08-1.97 (m, 3H), 1.26 (s, 9H), 0.85 (s, 9H), 0.01 (s, 6H).

Step 5. Synthesis of (R)—N—((S)-(trans-3-(tert-butyldimethylsilyloxy)cyclobutyl)(6-(1-(6-(((tert-butyldimethylsilyloxy)methyl)pyridin-2-yl)-1H-indazol-6-yl)pyridin-2-yl)methyl)-2-methylpropane-2-sulfinamide

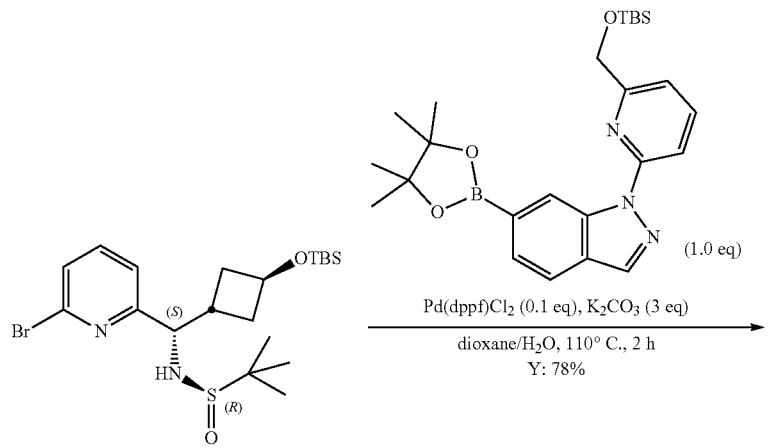

The preparation of (R)—N—((S)-(trans-3-(tert-butyldimethylsilyloxy)cyclobutyl)(6-(1-(6-(((tert-butyldimethylsilyloxy)methyl)pyridin-2-yl)-1H-indazol-6-yl)pyridin-2-yl)methyl)-2-methylpropane-2-sulfinamide was similar to that of (R)—N—((S)-(3-((tert-butyldimethylsilyloxy)methyl)cyclobutyl)(6-(1-(6-(((tert-butyldimethylsilyloxy)methyl)pyridin-2-yl)-1H-indazol-6-yl)pyridin-2-yl)methyl)-2-methylpropane-2-sulfinamide (P2) (Example 1, Step 10) to give 180 mg as a white solid. Y: 78%. ESI-MS (M+H)$^+$: 734.4. $^1$H NMR (400 MHz, CDCl$_3$) δ: 9.33 (s, 1H), 8.22 (s, 1H), 8.08-8.06 (m, 1H), 7.93-7.84 (m, 3H), 7.78-7.77 (m, 2H), 7.40 (d, J=7.6 Hz, 1H), 7.24-7.22 (m, 1H), 4.96 (s, 2H), 4.53-4.49 (m, 1H), 4.30-4.26 (m, 1H), 4.14-4.07 (m, 1H), 2.81-2.77 (m, 1H), 2.49-2.44 (m, 1H), 2.26-2.17 (m, 2H), 2.04-1.98 (m, 1H), 1.16 (s, 9H), 0.99 (s, 9H), 0.84 (s, 9H), 0.17 (s, 6H), 0.02 (s, 6H).

Step 6. Synthesis of trans-3-((S)-amino(6-(1-(6-(hydroxymethyl)pyridin-2-yl)-1H-indazol-6-yl)pyridin-2-yl)methyl)cyclobutanol (HCl)

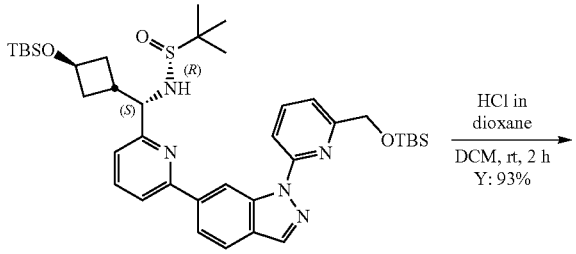

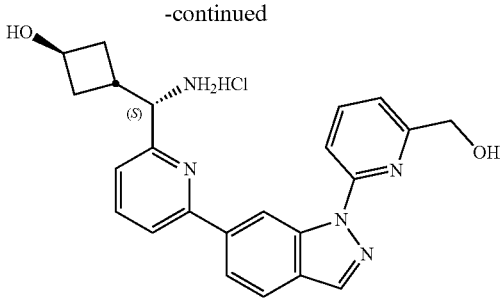

The preparation of trans-3-((S)-amino(6-(1-(6-(hydroxymethyl)pyridin-2-yl)-1H-indazol-6-yl)pyridin-2-yl)methyl)cyclobutanol (HCl) was similar to that of (S)-(6-(6-(6-(amino(3-(hydroxymethyl)cyclobutyl)methyl)pyridin-2-yl)-1H-indazol-1-yl)pyridin-2-yl)methanol (P2, HCl) (Example 1, Step 11) to give 100 mg as a white solid. Y: 93%. ESI-MS (M+H)+: 402.2. $^1$H NMR (400 MHz, CD$_3$OD)(S: 9.72 (s, 1H), 8.35 (s, 1H), 8.16-8.11 (m, 2H), 8.05-7.97 (m, 4H), 7.51-7.49 (m, 1H), 7.42-7.409 (m, 1H), 4.94 (s, 2H), 4.59-4.56 (m, 1H), 4.33-4.27 (m, 1H), 3.03-2.96 (m, 1H), 2.54-2.47 (m, 1H), 2.39-2.24 (m, 2H), 2.04-1.97 (m, 1H).

Example 7. trans-3-((R)-amino(6-(1-(6-(hydroxymethyl)pyridin-2-yl)-1H-indazol-6-yl)pyridin-2-yl)methyl)cyclobutanol Step 1. Synthesis of (R)—N—((R)-(trans-3-(tert-butyldimethylsilyloxy)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide

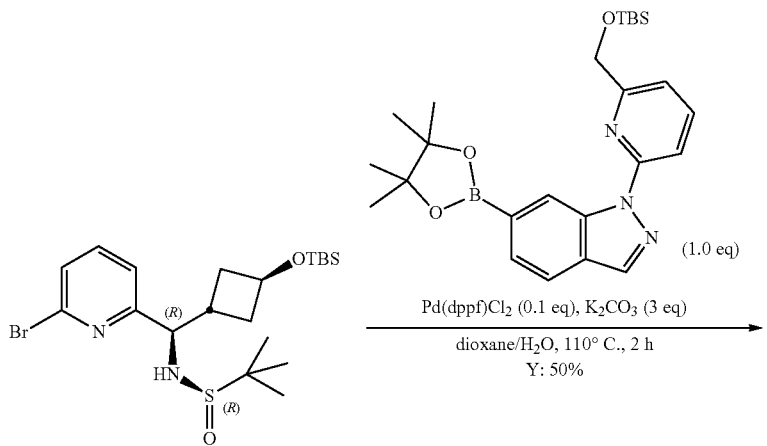

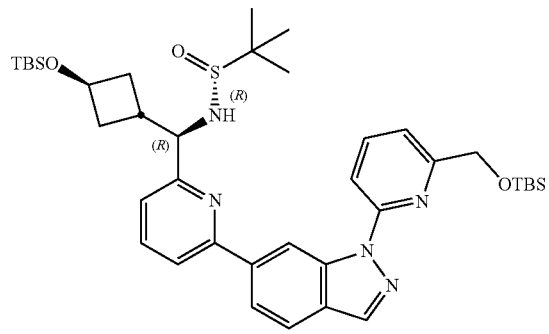

The preparation of (R)—N—((R)-((trans-3-(tert-butyldimethylsilyloxy)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide was similar to that of (R)—N—((S)-(3-((tert-butyldimethylsilyloxy)methyl)cyclobutyl)(6-(1-(6-((tert-butyldimethylsilyloxy)methyl)pyridin-2-yl)-1H-indazol-6-yl)pyridin-2-yl)methyl)-2-methylpropane-2-sulfinamide (P2) (Example 1, Step 10) to give 115 mg as a white solid. Y: 50%. ESI-MS (M+H)+: 734.4. ¹H NMR (400 MHz, CDCl₃) δ: 9.29 (s, 1H), 8.21 (s, 1H), 8.02-8.00 (m, 1H), 7.93-7.83 (m, 3H), 7.79-7.73 (m, 2H), 7.41-7.39 (m, 1H), 7.24-7.22 (m, 1H), 5.24-5.22 (m, 1H), 4.96 (s, 2H), 4.42-4.31 (m, 2H), 2.77-2.70 (m, 1H), 2.37-2.31 (m, 1H), 2.24-2.19 (m, 1H), 2.12-2.01 (m, 2H), 1.28 (s, 9H), 0.99 (s, 9H), 0.85 (s, 9H), 0.17 (s, 6H), 0.02 (s, 6H).

Step 2. Synthesis of trans-3-((R)-amino(6-(1-(6-(hydroxymethyl)pyridin-2-yl)-1H-indazol-6-yl)pyridin-2-yl)methyl)cyclobutanol (HCl)

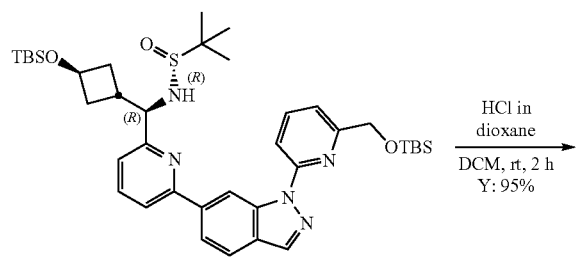

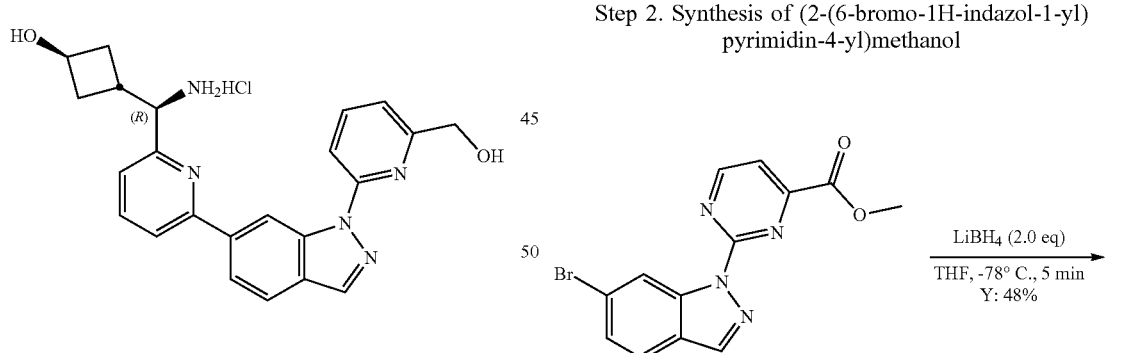

The preparation of trans-3-((R)-amino(6-(1-(6-(hydroxymethyl)pyridin-2-yl)-1H-indazol-6-yl)pyridin-2-yl)methyl)cyclobutanol (HCl) was similar to that of (S)-(6-(6-(6-(amino(3-(hydroxymethyl)cyclobutyl)methyl)pyridin-2-yl)-1H-indazol-1-yl)pyridin-2-yl)methanol (P2, HCl) (Example 1, Step 11) to give 65 mg as a yellow solid. Y: 95%. ESI-MS (M+H)+: 402.2. ¹H NMR (400 MHz, CD₃OD)(S: 9.75 (s, 1H), 8.35 (s, 1H), 8.15-8.10 (m, 2H), 8.04-7.96 (m, 4H), 7.50-7.48 (m, 1H), 7.40-7.38 (m, 1H), 4.92 (s, 2H), 4.57-4.55 (m, 1H), 4.29-4.27 (m, 1H), 3.01-2.97 (m, 1H), 2.51-2.48 (m, 2H), 2.37-2.26 (m, 2H), 2.04-2.00 (m, 1H).

Example 8 (1R,3S)-3-((S)-amino(6-(1-(4-(hydroxymethyl)pyrimidin-2-yl)-1H-indazol-6-yl)pyridin-2-yl)methyl)cyclobutanol Step 1. methyl 2-(6-bromo-1H-indazol-1-yl)pyrimidine-4-carboxylate

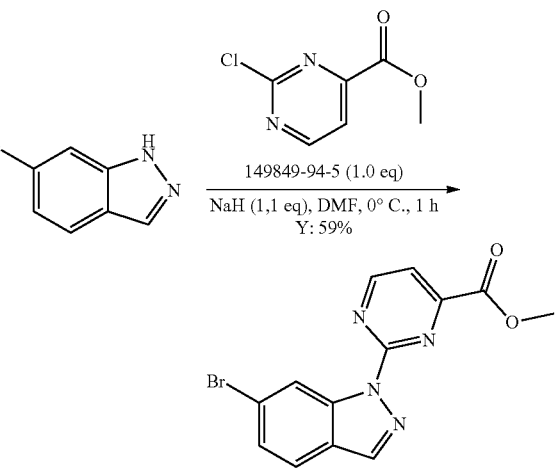

To a solution of 6-bromo-1H-indazole (Cas No. 79762-54-2, 400 mg, 2.04 mmol, 1.0 eq) in DMF (6 mL) was added NaH (90 mg, 2.24 mmol, 1.1 eq) at 0° C. After stirring at 0° C. for 15 min, Methyl 2-chloropyrimidine-4-carboxylate (CAS No. 149849-94-5, 352 mg, 2.04 mmol, 1.0 eq) dissolved in DMF (2 mL) was added and the reaction mixture was stirred at 0° C. for 1 h. The reaction mixture was poured into H₂O (40 mL) and stirred at rt for 15 min. The precipitate was collected by filtration and dried to give methyl 2-(6-bromo-1H-indazol-1-yl)pyrimidine-4-carboxylate. 400 mg, as a yellow solid, Y: 59%. ESI-MS (M+H)+: 333.0.

Step 2. Synthesis of (2-(6-bromo-1H-indazol-1-yl)pyrimidin-4-yl)methanol

To a solution of methyl 2-(6-bromo-1H-indazol-1-yl)pyrimidine-4-carboxylate (300 mg, 0.9 mmol, 1.0 eq in THF (15 mL) was added LiBH₄ (1.8 mL, 1.8 mmol, 2.0 eq) dropwise at −78° C. After stirring at −78° C. for 5 min, the reaction was quenched with sat. NH₄Cl solution. The mixture was filtrated and the filtrate was extracted with EA (30 mL×3). The combined organic phases were dried and concentrated to give (2-(6-bromo-1H-indazol-1-yl)pyrimidin-4-yl)methanol. 110 mg, as a yellow solid, Y: 48%. ESI-MS (M+H)⁺: 305.0.

Step 3. Synthesis of 6-bromo-1-(4-(((tert-butyldimethylsilyl)oxy)methyl)pyrimidin-2-yl)-1H-indazole

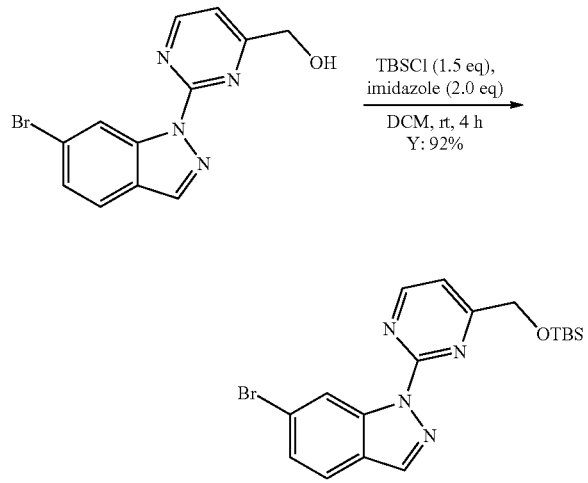

The preparation of 6-bromo-1-(4-(((tert-butyldimethylsilyl)oxy)methyl)pyrimidin-2-yl)-1H-indazole was similar to that of methyl 3-((tert-butyldimethylsilyloxy)methyl)cyclobutanecarboxylate (Example 1, Step 3) to give 140 mg as a white solid, Y: 92%. ESI-MS (M+H)⁺: 419.1. ¹H NMR (400 MHz, CDCl₃) δ: 9.02 (s, 1H), 8.83 (d, J=5.2 Hz, 1H), 8.27 (s, 1H), 7.65 (d, J=8.4 Hz, 1H), 7.47-7.44 (m, 2H), 4.95 (s, 2H), 0.92 (s, 9H), 0.08 (s, 6H).

Step 4. Synthesis of 1-(4-(((tert-butyldimethylsilyl)oxy)methyl)pyrimidin-2-yl)-6-(4,4,5,5-tetramethyl-1,3,2-dioxaborolan-2-yl)-1H-indazole

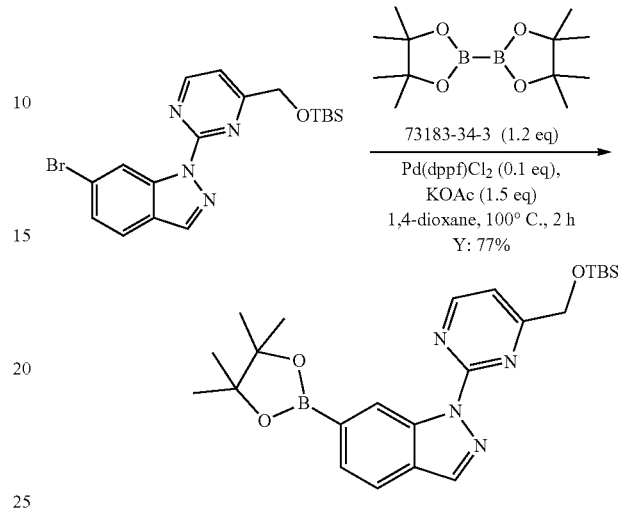

The preparation of 1-(4-(((tert-butyldimethylsilyl)oxy)methyl)pyrimidin-2-yl)-6-(4,4,5,5-tetramethyl-1,3,2-dioxaborolan-2-yl)-1H-indazole was similar to that of 1-(6-(((tert-butyldimethylsilyl)oxy)methyl)pyridin-2-yl)-6-(4,4,5,5-tetramethyl-1,3,2-dioxaborolan-2-yl)-1H-indazole (Example 1, Step 9) to give 120 mg as a brown solid, Y: 77%. ESI-MS (M+H)⁺: 467.2.

Step 5. Synthesis of (R)—N—((S)-((1s,3R)-3-(tert-butyldimethylsilyloxy)cyclobutyl)(6-(1-(4-((tert-butyldimethylsilyloxy)methyl)pyrimidin-2-yl)-1H-indazol-6-yl)pyridin-2-yl)methyl)-2-methylpropane-2-sulfinamide

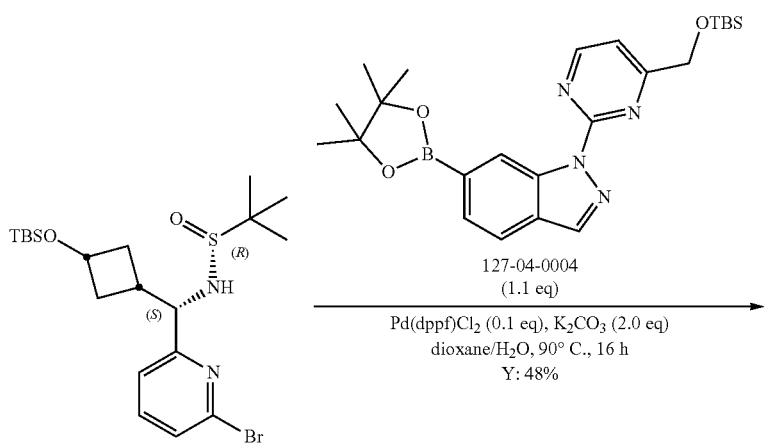

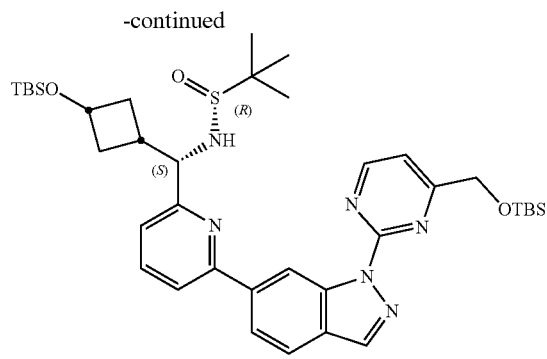

To a reaction mixture of (R)—N—((S)-(6-bromopyridin-2-yl)((1s,3R)-3-(tert-butyldimethylsilyloxy)cyclobutyl)methyl)-2-methylpropane-2-sulfinamide (Example 4, Step 5) 60 mg, 0.12 mmol, 1.0 eq), 1-(4-((tert-butyldimethylsilyloxy)methyl)pyrimidin-2-yl)-6-(4,4,5,5-tetramethyl-1,3,2-dioxaborolan-2-yl)-1H-indazole from previous step 65 mg, 0.14 mmol, 1.1 eq) and K$_2$CO$_3$ (33 mg, 0.24 mmol, 2.0 eq) in dioxane (3 mL) and H$_2$O (0.3 mL) was added Pd(dppf)Cl$_2$ (10 mg, 0.01 mmol, 0.1 eq). The reaction mixture was stirred at 90° C. for 16 h under N$_2$. After cooling to rt, the reaction mixture was concentrated and the residue was purified by silica gel using PE/EA (2/1) as eluent to give (R)—N—((S)-((1s,3R)-3-(tert-butyldimethylsilyloxy)cyclobutyl)(6-(1-(4-((tert-butyldimethylsilyloxy)methyl)pyrimidin-2-yl)-1H-indazol-6-yl)pyridin-2-yl)methyl)-2-methylpropane-2-sulfinamide as yellow oil (45 mg, Y: 48%). ESI-MS (M+H)$^+$: 735.4.

Synthesis of (1R,3s)-3-((S)-amino(6-(1-(4-(hydroxymethyl)pyrimidin-2-yl)-1H-indazol-6-yl)pyridin-2-yl)methyl)cyclobutanol (TFA)

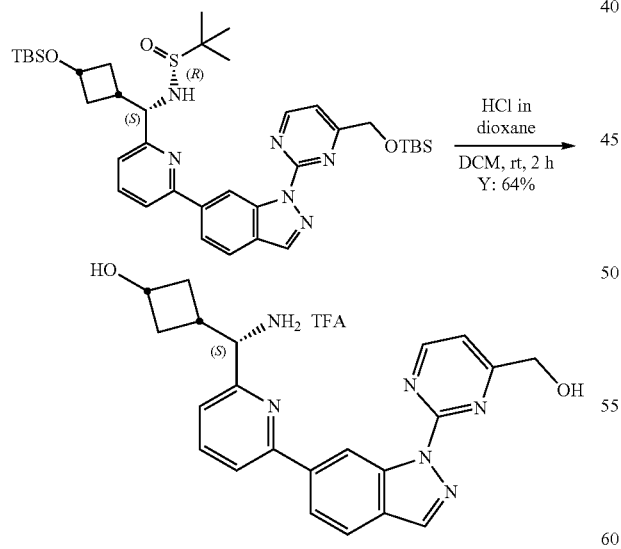

A solution of (R)—N—((S)-((1s,3R)-3-(tert-butyldimethylsilyloxy)cyclobutyl)(6-(1-(4-((tert-butyldimethylsilyloxy)methyl)pyrimidin-2-yl)-1H-indazol-6-yl)pyridin-2-yl)methyl)-2-methylpropane-2-sulfinamide (45 mg, 0.06 mmol, 1.0 eq) in DCM (3 mL) was added HCl in dioxane (0.5 mL, 4M). The mixture was stirred at rt for 2 h. After filtration and concentration, the residue was purified by HPLC-preparation (0.05% TFA in H$_2$O/CH$_3$CN=0%-100%) to give (1R,3s)-3-((S)-amino(6-(1-(4-(hydroxymethyl)pyrimidin-2-yl)-1H-indazol-6-yl)pyridin-2-yl)methyl)cyclobutanol (TFA) (15 mg, Y: 64%) as a white solid. ESI-MS (M+H)$^+$: 403.2. HPLC: 100% $^1$H NMR (400 MHz, CD$_3$OD) δ: 9.56 (s, 1H), 8.91 (s, 1H), 8.52 (s, 1H), 8.26 (d, J=8.4 Hz, 1H), 8.10 (d, J=7.6 Hz, 1H), 8.05-8.01 (m, 2H), 7.54 (s, 1H), 7.47 (d, J=7.6 Hz, 1H), 4.94 (s, 2H), 4.52-4.50 (m, 1H), 4.18-4.11 (m, 1H), 2.66-2.59 (m, 1H), 2.41-2.33 (m, 1H), 2.30-2.22 (m, 1H), 1.98-1.88 (m, 2H).

Example 9 cis 3-((S)-amino(6-(1-(6-(hydroxymethyl)pyrazin-2-yl)-1H-indazol-6-yl)pyridin-2-yl)methyl)cyclobutanol Step 1. Synthesis of methyl 6-(6-bromo-1H-indazol-1-yl)pyrazine-2-carboxylate

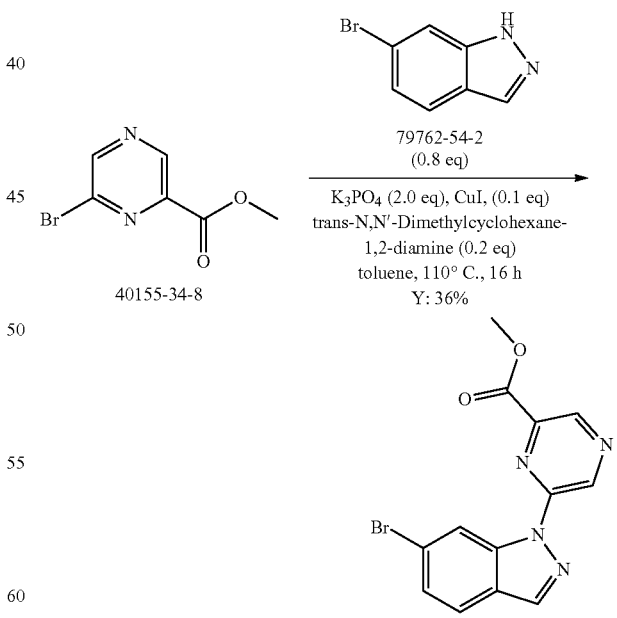

The preparation of methyl 6-(6-bromo-1H-indazol-1-yl)pyrazine-2-carboxylate was similar to that of (6-(6-bromo-1H-indazol-1-yl)pyridin-2-yl)methanol (Example 1, Step 7) to give 1.1 g as a yellow solid, Y: 36%. ESI-MS (M+H)$^+$: 333.0. $^1$H NMR (400 MHz, CDCl$_3$) δ: 9.61 (s, 1H), 9.21 (s, 1H), 9.17 (s, 1H), 8.28 (s, 1H), 7.71 (d, J=8.4 Hz, 1H), 7.52 (dd, J=8.4, 1.2 Hz, 1H), 4.15 (s, 3H).

Step 2. Synthesis of (6-(6-bromo-1H-indazol-1-yl)pyrazin-2-yl)methanol

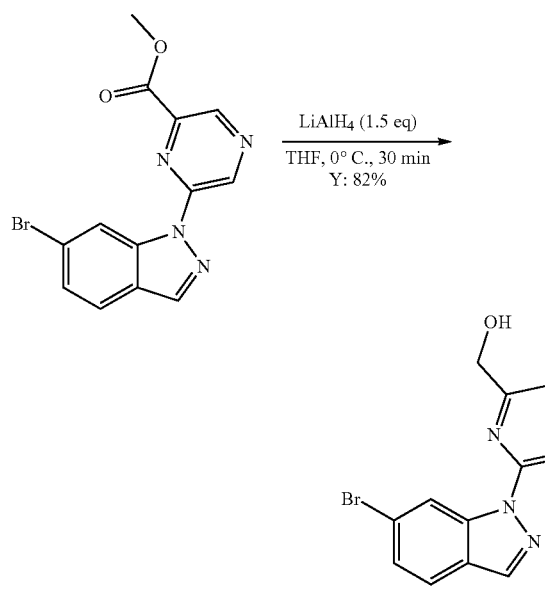

The preparation of (6-(6-bromo-1H-indazol-1-yl)pyrazin-2-yl)methanol was similar to that of (2-(6-bromo-1H-indazol-1-yl)pyrimidin-4-yl)methanol (Example 8, Step 2) to give 1.0 g as a yellow solid, Y: 82%. ESI-MS (M+H)$^+$: 305.0.

Step 3. Synthesis of 6-bromo-1-(6-(((tert-butyldimethylsilyl)oxy)methyl)pyrazin-2-yl)-1H-indazole

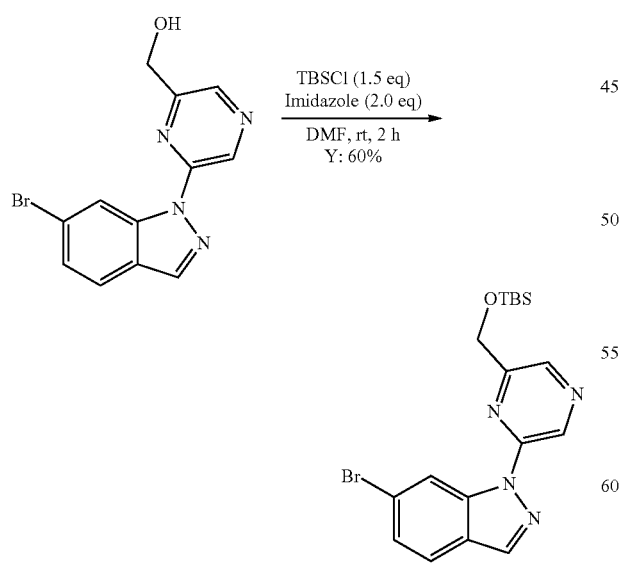

The preparation of 6-bromo-1-(6-(((tert-butyldimethylsilyl)oxy)methyl)pyrazin-2-yl)-1H-indazole was similar to that of methyl 3-(((tert-butyldimethylsilyloxy)methyl)cyclobutanecarboxylate (Example 1, Step 3) to give 830 mg as a yellow solid, Y: 60%. ESI-MS (M+H)$^+$: 419.1. $^1$H NMR (400 MHz, CDCl$_3$) δ: 9.29 (s, 1H), 8.93 (s, 1H), 8.63 (s, 1H), 8.21 (s, 1H), 7.66 (d, J=8.0 Hz, 1H), 7.44 (dd, J=8.8, 1.6 Hz, 1H), 4.98 (s, 2H), 1.01 (s, 9H), 0.19 (s, 6H).

Step 4. Synthesis of 1-(6-(((tert-butyldimethylsilyl)oxy)methyl)pyrazin-2-yl)-6-(4,4,5,5-tetramethyl-1,3,2-dioxaborolan-2-yl)-1H-indazole

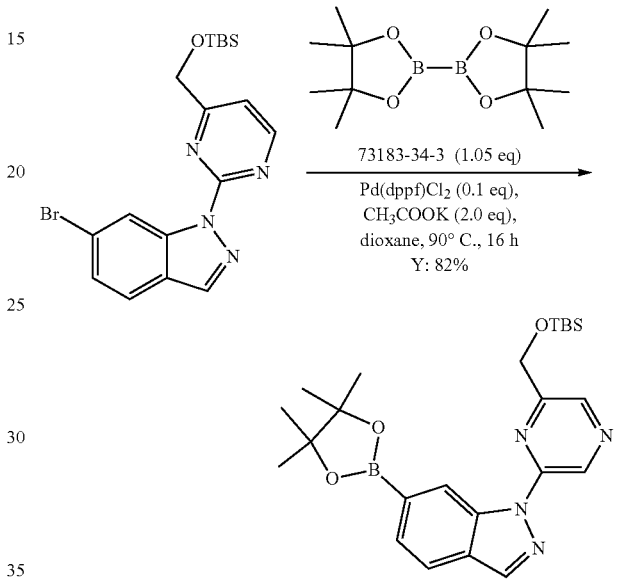

The preparation of 1-(6-(((tert-butyldimethylsilyl)oxy)methyl)pyrazin-2-yl)-6-(4,4,5,5-tetramethyl-1,3,2-dioxaborolan-2-yl)-1H-indazole was similar to that of 1-(6-(((tert-butyldimethylsilyl)oxy)methyl)pyridin-2-yl)-6-(4,4,5,5-tetramethyl-1,3,2-dioxaborolan-2-yl)-1H-indazole (Example 1, Step 9) to give 310 mg as a yellow solid, Y: 82%. ESI-MS (M+H)$^+$: 467.3.

Step 5. Synthesis of (R)—N—((S)-(cis 3-(tert-butyldimethylsilyloxy)cyclobutyl)(6-(1-(6-(((tert-butyldimethylsilyloxy)methyl)pyrazin-2-yl)-1H-indazol-6-yl)pyridin-2-yl)methyl)-2-methylpropane-2-sulfinamide

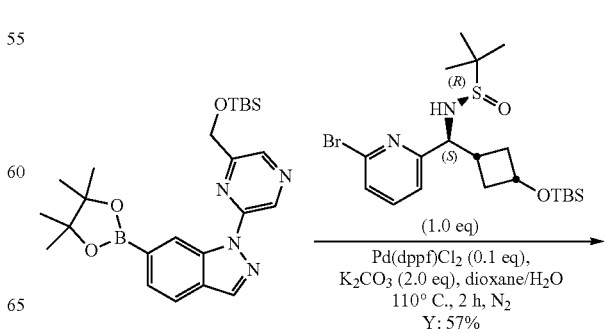

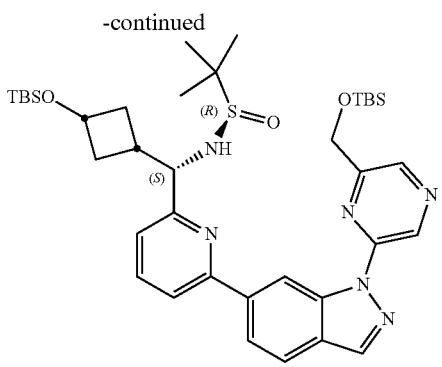

A mixture of 1-(6-((tert-butyldimethylsilyloxy)methyl)pyrazin-2-yl)-6-(4,4,5,5-tetramethyl-1,3,2-dioxaborolan-2-yl)-1H-indazole from in previous step 115 mg, 0.25 mmol, 1.0 eq), (R)—N—((S)-(6-bromopyridin-2-yl)((cis-3-(tert-butyldimethylsilyloxy)cyclobutyl)methyl)-2-methylpropane-2-sulfinamide (Example 4, Step 5) 120 mg, 0.25 mmol, 1.0 eq) and K₂CO₃ (70 mg, 0.5 mmol, 2.0 eq) in 1,4-dioxane/H₂O (4/1, 10 mL) was stirred while purging N₂ at rt for 10 min. To this system was added Pd(dppf)Cl₂ (25 mg, 0.03 mmol, 0.1 eq) and heated to 110° C. for 2 h. After concentrated, the mixture was purified by silica gel chromatography using PE/EA (2/1) as eluent to give (R)—N—((S)-(cis-3-(tert-butyldimethylsilyloxy)cyclobutyl)(6-(1-(6-((tert-butyldimethylsilyloxy)methyl)pyrazin-2-yl)-1H-indazol-6-yl)pyridin-2-yl)methyl)-2-methylpropane-2-sulfinamide as a yellow solid. 100 mg, Y: 57%, ESI-MS (M+H)⁺: 735.4. Step 6. Synthesis of cis 3-((S)-amino(6-(1-(6-(hydroxymethyl)pyrazin-2-yl)-1H-indazol-6-yl)pyridin-2-yl)methyl)cyclobutanol

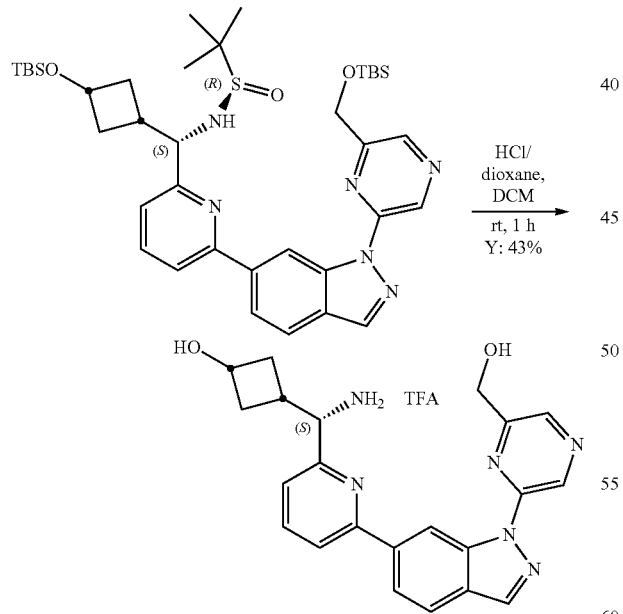

To a solution of (R)—N—((S)-(cis-3-(tert-butyldimethylsilyloxy)cyclobutyl)(6-(1-(6-((tert-butyldimethylsilyloxy)methyl)pyrazin-2-yl)-1H-indazol-6-yl)pyridin-2-yl)methyl)-2-methylpropane-2-sulfinamide (100 mg, 0.14 mmol, 1.0 eq) in DCM (3 mL) was added HCl/Dioxane (4 M, 0.5 mL, excess). The mixture was stirred at rt for 1 h.

After concentration, the residue was dissolved in THF, adjusted pH=7-8 with NaHCO₃ solution and extracted with EA (50 mL×2). The combined organic phase was washed with brine and dried over Na₂SO₄. After filtration and concentration, the residue was purified by prep-HPLC (CH₃CN/0.05% TFA in H₂O=0%~100%) to give cis-3-((S)-amino(6-(1-(6-(hydroxymethyl)pyrazin-2-yl)-1H-indazol-6-yl)pyridin-2-yl)methyl)cyclobutanol as a yellow solid. 30 mg, Y: 43%, ESI-MS (M+H)⁺: 403.2. HPLC: 100%. $^1$H NMR (400 MHz, CD₃OD) δ: 9.62 (s, 1H), 9.24 (s, 1H), 8.54 (s, 1H), 8.39 (s, 1H), 8.17 (dd, J=8.4, 0.8 Hz, 1H), 8.07-7.96 (m, 3H), 7.43 (d, J=7.6 Hz, 1H), 4.93 (s, 2H), 4.47 (d, J=9.6 Hz, 1H), 4.15-4.10 (m, 1H), 2.63-2.58 (m, 1H), 2.40-2.20 (m, 2H), 1.95-1.85 (m, 2H).

Example 10 (1R,3S)-3-((S)-amino(6-(1-(6-(trifluoromethyl)pyridin-2-yl)-1H-indazol-6-yl)pyridin-2-yl)methyl)cyclobutanol Step 1. Synthesis of 6-bromo-1-(6-(trifluoromethyl)pyridin-2-yl)-1H-indazole

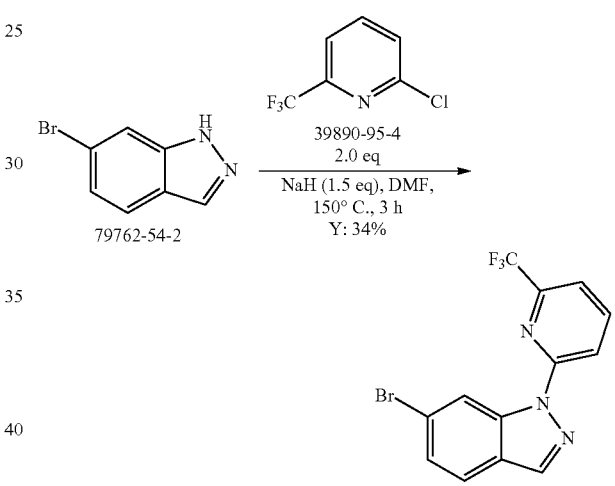

The preparation of 6-bromo-1-(6-(trifluoromethyl)pyridin-2-yl)-1H-indazole was similar to that of methyl 2-(6-bromo-1H-indazol-1-yl)pyrimidine-4-carboxylate (Example 8, Step 1). 600 mg, as a yellow solid, Y: 34%. ESI-MS (M+H)⁺: 342.0.

Step 2. Synthesis of 6-(4,4,5,5-tetramethyl-1,3,2-dioxaborolan-2-yl)-1-(6-(trifluoromethyl)pyridin-2-yl)-1H-indazole

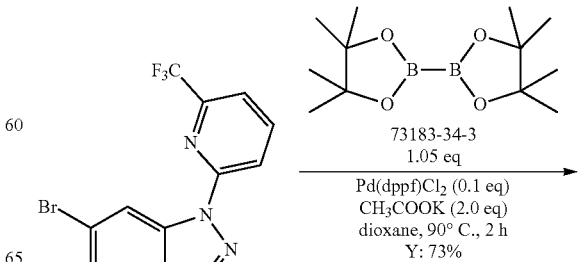

-continued

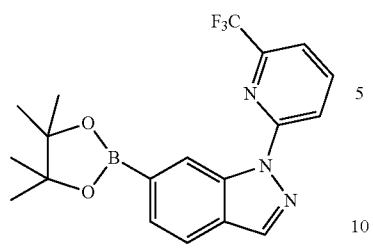

The preparation of 6-(4,4,5,5-tetramethyl-1,3,2-dioxaborolan-2-yl)-1-(6-(trifluoromethyl)pyridin-2-yl)-1H-indazole was the same as that of 1-(6-(((tert-butyldimethylsilyl)oxy)methyl)pyridin-2-yl)-6-(4,4,5,5-tetramethyl-1,3,2-dioxaborolan-2-yl)-1H-indazole (Example 1, Step 9). 500 mg, as a yellow solid, Y: 73%. ESI-MS (M+H)$^+$: 390.2.

Step 3 Synthesis of (R)—N—((S)-(6-bromopyridin-2-yl)((1s,3R)-3-hydroxycyclobutyl)methyl)-2-methylpropane-2-sulfinamide

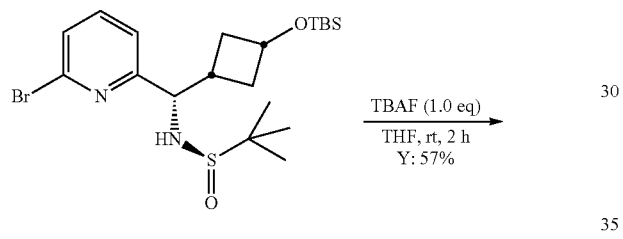

To a solution of (R)—N—((S)-(6-bromopyridin-2-yl)((1s,3R)-3-((tert-butyldimethylsilyl)oxy)cyclobutyl)methyl)-2-methylpropane-2-sulfinamide (example 4 step 5) (12 g, 25.3 mmol) in THF (200 ml) was added TBAF (6.6 g, 25.3 mmol, 1.0 eq) at rt. The mixture was stirred at rt for 2 h. The mixture was quenched with NaHCO$_3$ (aq.) and extracted with DCM (100 mL×3). The organics were washed with brine, dried, concentrated under reduced pressure. The residue was purified by silica gel chromatography with DCM/MeOH (40/1) to QCP-15087909-01 as a off-white solid (5.2 g; Y: 57%). ESI-MS (M+H)$^+$: 361.1. $^1$H NMR (400 MHz, CDCl$_3$) δ: 7.50 (t, J=7.6 Hz, 1H), 7.37 (d, J=7.6 Hz, 1H), 7.17 (d, J=7.6 Hz, 1H), 4.34 (t, J=7.2 Hz, 1H), 4.15-4.08 (m, 2H), 2.57-2.51 (m, 1H), 2.32-2.22 (m, 3H), 1.89-1.77 (m, 1H), 1.19 (s, 9H).

Step 4. Synthesis of (R)—N—((S)-((1s,3R)-3-hydroxycyclobutyl)(6-(1-(6-(trifluoromethyl)pyridin-2-yl)-1H-indazol-6-yl)pyridin-2-yl)methyl)-2-methylpropane-2-sulfinamide

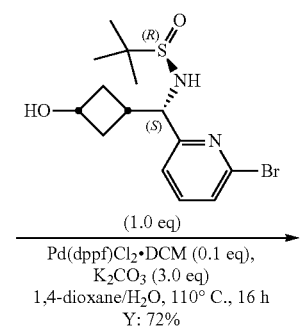

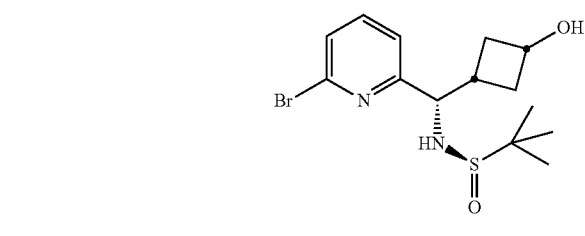

The preparation of (R)—N—((S)-((1s,3R)-3-hydroxycyclobutyl)(6-(1-(6-(trifluoromethyl)pyridin-2-yl)-1H-indazol-6-yl)pyridin-2-yl)methyl)-2-methylpropane-2-sulfinamide was similar to that of (R)—N—((S)-(cis 3-(tert-butyldimethylsilyloxy)cyclobutyl)(6-(1-(6-((tert-butyldimethylsilyloxy)methyl)pyrazin-2-yl)-1H-indazol-6-yl)pyridin-2-yl)methyl)-2-methylpropane-2-sulfinamide (Example 9, Step 5) to give 110 mg as a yellow solid. Y: 72%, ESI-MS (M+H)$^+$: 544.2.

Step 5. Synthesis of (1R,3s)-3-((S)-amino(6-(1-(6-(trifluoromethyl)pyridin-2-yl)-1H-indazol-6-yl)pyridin-2-yl)methyl)cyclobutanol

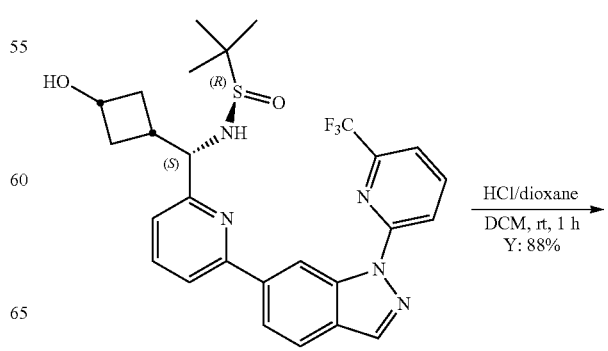

-continued

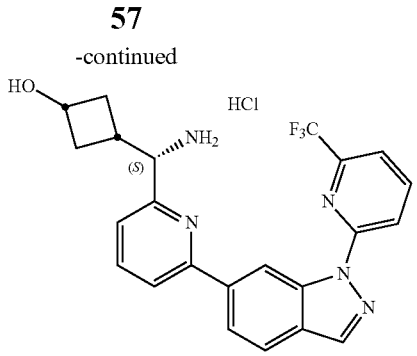

The preparation of (1R,3s)-3-((S)-amino(6-(1-(6-(trifluoromethyl)pyridin-2-yl)-1H-indazol-6-yl)pyridin-2-yl)methyl)cyclobutanol was similar to that of cis 3-((S)-amino(6-(1-(6-(hydroxymethyl)pyrazin-2-yl)-1H-indazol-6-yl)pyridin-2-yl)methyl)cyclobutanol (Example 9, Step 6) to give 85 mg (HCl salt) as a yellow solid. Y: 88%, ESI-MS (M+H)$^+$: 440.2. HPLC: 100%. $^1$H NMR (400 MHz, CD$_3$OD) δ: 9.54 (s, 1H), 8.41 (s, 1H), 8.37 (d, J=8.8 Hz, 1H), 8.25-8.20 (m, 2H), 8.05-7.99 (m, 3H), 7.72 (d, J=7.6 Hz, 1H), 7.46 (dd, J=6.8, 1.6 Hz, 1H), 4.46 (d, J=9.6 Hz, 1H), 4.18-4.11 (m, 1H), 2.66-2.59 (m, 1H), 2.45-2.36 (m, 1H), 2.28-2.20 (m, 1H), 1.97-1.85 (m, 2H).

Example 11 (1R,3S)-3-((S)-amino(6-(1-(4-ethylpyrimidin-2-yl)-1H-indazol-6-yl)pyridin-2-yl)methyl)cyclobutanol Step 1. Synthesis of 6-bromo-1-(4-ethylpyrimidin-2-yl)-1H-indazole

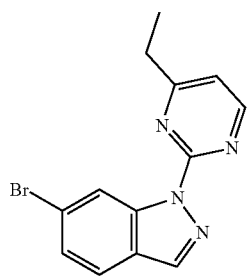

To a solution of 6-bromo-1H-indazole (2.5 g, 12.7 mmol, 1.0 eq) in dry DMF (10 mL) was slowly added NaH (560 mg, 14.0 mmol, 1.1 eq) at rt. After stirring at rt for 10 min, 2-chloro-4-ethylpyrimidine (2.0 g, 14.0 mmol, 1.1 eq) was added to the mixture. Then the mixture was stirred at 130° C. for 4 h under N$_2$ atmosphere. After cooling down to rt, the mixture was diluted with H$_2$O (50 mL) and stirred at rt for 10 min. The precipitate was collected by filtration and was purified by silica gel chromatography (PE/EA=3/1) to give 6-bromo-1-(4-ethylpyrimidin-2-yl)-1H-indazole as a yellow solid. 3.5 g, Y: 91%. ESI-MS (M+H)$^+$: 303.1. $^1$H NMR (400 MHz, CDCl$_3$) δ: 9.06 (s, 1H), 8.69 (d, J=5.2 Hz, 1H), 8.26 (s, 1H), 7.64 (d, J=8.4 Hz, 1H), 7.42 (d, J=8.0 Hz, 1H), 7.07 (d, J=5.2 Hz, 1H), 2.96 (q, J=7.6 Hz, 2H), 1.43 (t, J=7.6 Hz, 3H).

Step 2. Synthesis of 1-(4-ethylpyrimidin-2-yl)-6-(4,4,5,5-tetramethyl-1,3,2-dioxaborolan-2-yl)-1H-indazole

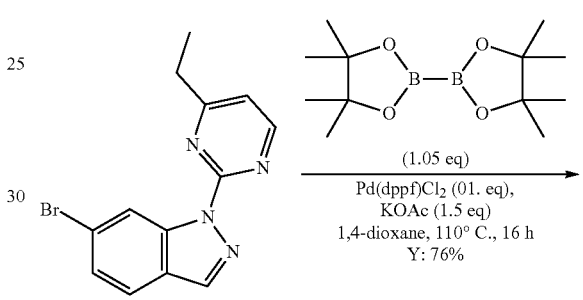

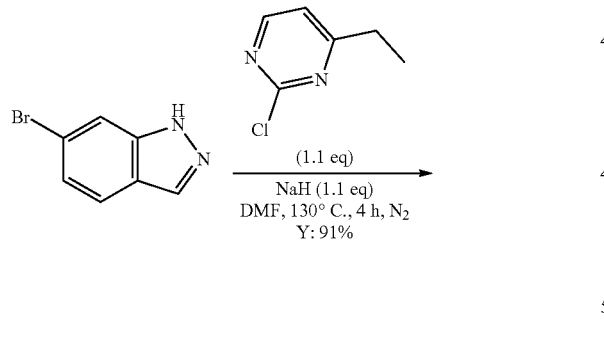

A mixture of 6-bromo-1-(4-ethylpyrimidin-2-yl)-1H-indazole (170 mg, 0.56 mmol, 1.0 eq), 4,4,4',4',5,5,5',5'-octamethyl-2,2'-bi(1,3,2-dioxaborolane) (150 mg, 0.59 mmol, 1.05 eq) and CH$_3$COOK (110 mg, 1.12 mmol, 2.0 eq) in 1,4-dioxane (20 mL) was stirred while purging N$_2$ at rt for 10 min. To this system was added Pd(dppf)Cl$_2$ (51 mg, 0.06 mmol, 0.1 eq) and heated to 110° C. for 16 h. The mixture was diluted with EA (50 mL) and washed with brine (50 mL). The organic phase was dried (Na$_2$SO$_4$) and concentrated to give 1-(4-ethylpyrimidin-2-yl)-6-(4,4,5,5-tetramethyl-1,3,2-dioxaborolan-2-yl)-1H-indazole, which was used for Step 3 without further purification. 150 mg, as a brown solid, Y: 76%. ESI-MS (M+H)$^+$: 351.2.

Step 3. Synthesis of (R)—N—((S)-(6-(1-(4-ethylpyrimidin-2-yl)-1H-indazol-6-yl)pyridin-2-yl)((1s,3R)-3-hydroxycyclobutyl)methyl)-2-methylpropane-2-sulfinamide

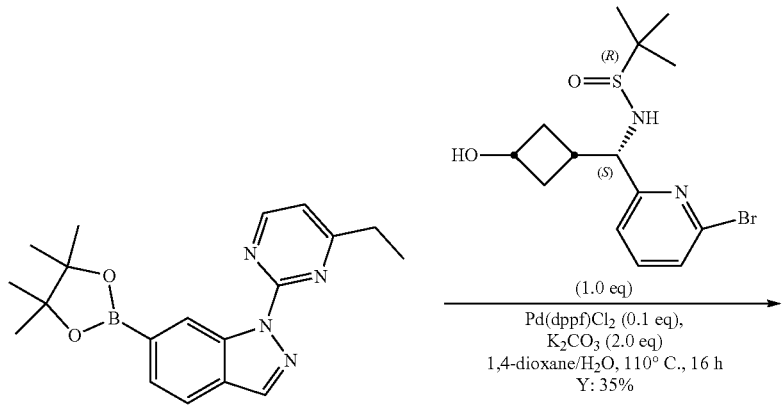

The preparation of (R)—N—((S)-(6-(1-(4-ethylpyrimidin-2-yl)-1H-indazol-6-yl)pyridin-2-yl)((1s,3R)-3-hydroxycyclobutyl)methyl)-2-methylpropane-2-sulfinamide was similar to that of (R)—N—((S)-((1s,3R)-3-hydroxycyclobutyl)(6-(1-(6-(trifluoromethyl)pyridin-2-yl)-1H-indazol-6-yl)pyridin-2-yl)methyl)-2-methylpropane-2-sulfinamide (Example 10, Step 4) to give 50 mg as a yellow solid. Y: 35%, ESI-MS (M+H)$^+$: 505.2.

Step 4. Synthesis of (1R,3s)-3-((S)-amino(6-(1-(4-ethylpyrimidin-2-yl)-1H-indazol-6-yl)pyridin-2-yl)methyl)cyclobutanol

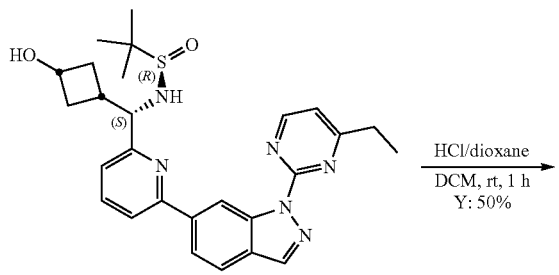

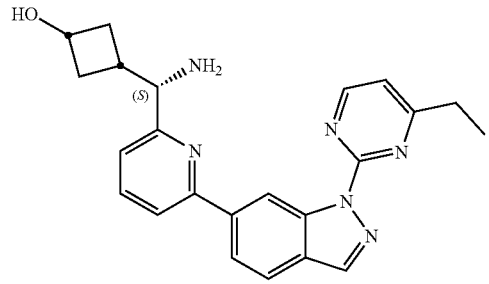

The preparation of (1R,3s)-3-((S)-amino(6-(1-(4-ethylpyrimidin-2-yl)-1H-indazol-6-yl)pyridin-2-yl)methyl)cyclobutanol was similar to that of cis 3-((S)-amino(6-(1-(6-(hydroxymethyl)pyrazin-2-yl)-1H-indazol-6-yl)pyridin-2-yl)methyl)cyclobutanol (Example 9, Step 6) to give 20 mg as a yellow solid (TFA salt). Y: 50%, ESI-MS (M+H)$^+$: 401.2, HPLC: 100%. $^1$H NMR (400 MHz, CD$_3$OD) δ: 9.45 (s, 1H), 8.75 (s, 1H), 8.44 (s, 1H), 8.22 (d, J=8.4 Hz, 1H), 8.05-7.98 (m, 3H), 7.45 (d, J=6.4 Hz, 1H), 7.29 (s, 1H), 4.49 (d, J=9.2 Hz, 1H), 4.18-4.11 (m, 1H), 3.01 (q, J=7.6 Hz, 2H), 2.66-2.58 (m, 1H), 2.41-2.21 (m, 2H), 1.97-1.87 (m, 2H), 1.52 (t, J=7.6 Hz, 3H).

Example 12. (1R,3s)-3-((S)-amino(6-(1-(6-eth-ylpyridin-2-yl)-1H-indazol-6-yl)pyridin-2-yl)methyl)cyclobutanol Step 1. Synthesis of 2-bromo-6-ethylpyridine

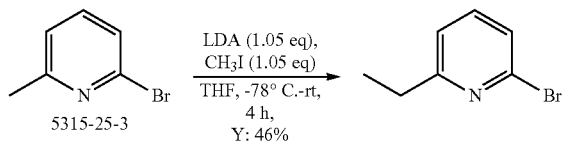

To a solution of 2-bromo-6-methylpyridine (CAS #5315-25-3) (2.0 g, 11.7 mmol, 1.0 eq) in THF (10 mL) was added LDA (12.3 mL, 12.3 mmol, 1.05 eq) at −78° C. After stirring at −78° C. for 1 h, CH₃I (1.8 g, 12.3 mmol, 1.05 eq) was added to the mixture. The mixture was stirred at rt for 3 h. The mixture was quenched with sat. NH₄Cl (2 mL), diluted with water (50 mL) and extracted with EA (2×100 mL). The combined organic phase was washed with brine and dried over Na₂SO₄. After concentration, the residue was purified by silica gel chromatography with PE/EA (20/1) as eluent to give 2-bromo-6-ethylpyridine. 1.0 g, as a yellow solid, Y: 46%. ESI-MS (M+H)⁺: 185.9, 187.9.

Step 2. Synthesis of 6-bromo-1-(6-ethylpyridin-2-yl)-1H-indazole

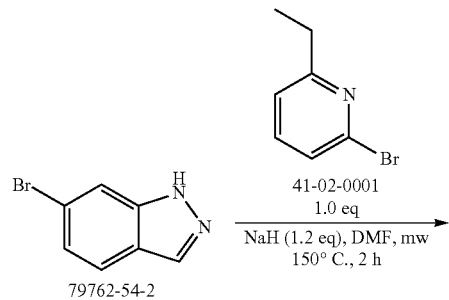

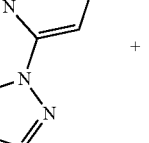

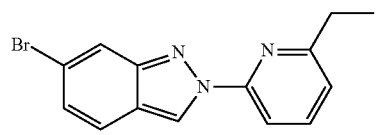

The preparation of 6-bromo-1-(6-ethylpyridin-2-yl)-1H-indazole was similar to that of 6-bromo-1-(4-ethylpyrimidin-2-yl)-1H-indazole (Example 11, Step 1). The mixture of 6-bromo-1-(6-ethylpyridin-2-yl)-1H-indazole and 6-bromo-2-(6-ethylpyridin-2-yl)-2H-indazole was purified by pre-TLC (PE/EA=10/1) to give 41-02-0002 and 6-bromo-2-(6-ethylpyridin-2-yl)-2H-indazole. R$_f$ value of 6-bromo-1-(6-ethylpyridin-2-yl)-1H-indazoR¹ is more than that of 6-bromo-2-(6-ethylpyridin-2-yl)-2H-indazole.

6-bromo-1-(6-ethylpyridin-2-yl)-1H-indazole, 230 mg, as a yellow solid, Y: 26%. ESI-MS (M+H)⁺: 302.0, 304.0.

6-bromo-2-(6-ethylpyridin-2-yl)-2H-indazole, 170 mg, as a yellow solid, Y: 19%. ESI-MS (M+H)⁺: 302.0, 304.0.

Step 3. Synthesis of 1-(6-ethylpyridin-2-yl)-6-(4,4,5,5-tetramethyl-1,3,2-dioxaborolan-2-yl)-1H-indazole

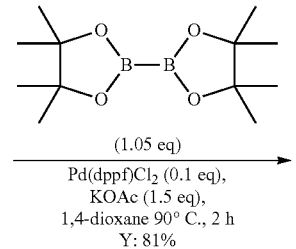

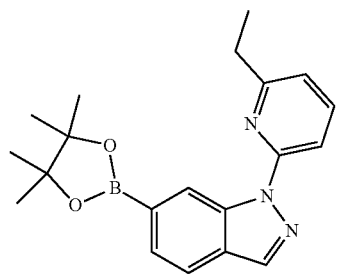

The preparation of 1-(6-ethylpyridin-2-yl)-6-(4,4,5,5-tetramethyl-1,3,2-dioxaborolan-2-yl)-1H-indazole was similar to that of 1-(4-ethylpyrimidin-2-yl)-6-(4,4,5,5-tetramethyl-1,3,2-dioxaborolan-2-yl)-1H-indazole (Example 11, Step 2). 216 mg, as a yellow solid, Y: 81%. ESI-MS (M+H)⁺: 350.2.

Step 4. Synthesis of (R)—N—((S)-(6-(1-(6-ethylpyridin-2-yl)-1H-indazol-6-yl)pyridin-2-yl)((1s,3R)-3-hydroxycyclobutyl)methyl)-2-methylpropane-2-sulfinamide

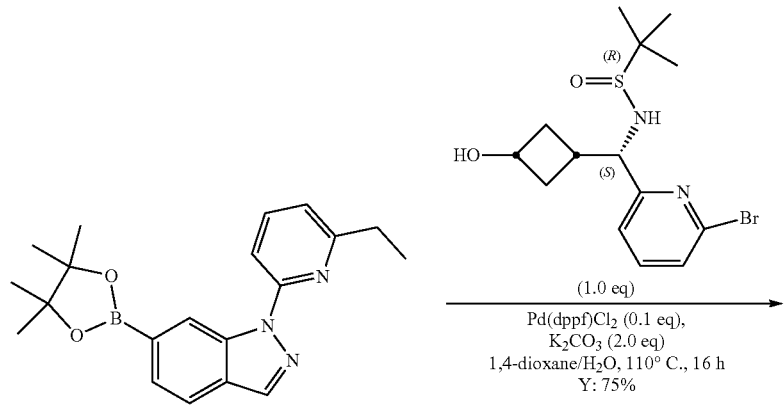

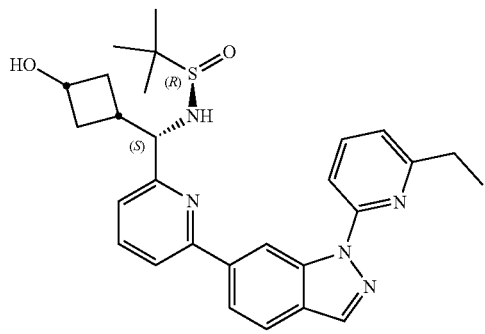

The preparation of (R)—N—((S)-(6-(1-(6-ethylpyridin-2-yl)-1H-indazol-6-yl)pyridin-2-yl)((1s,3R)-3-hydroxycyclobutyl)methyl)-2-methylpropane-2-sulfinamide was similar to that of (R)—N—((S)-((1s,3R)-3-hydroxycyclobutyl)(6-(1-(6-(trifluoromethyl)pyridin-2-yl)-1H-indazol-6-yl)pyridin-2-yl)methyl)-2-methylpropane-2-sulfinamide (Example 10, Step 4) to give 100 mg as a yellow solid, Y: 75%. ESI-MS (M+H)+: 504.2.

Step 5. Synthesis of (1R,3s)-3-((S)-amino(6-(1-(6-ethylpyridin-2-yl)-1H-indazol-6-yl)pyridin-2-yl)methyl)cyclobutanol

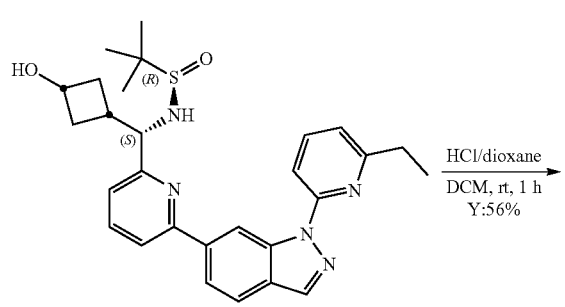

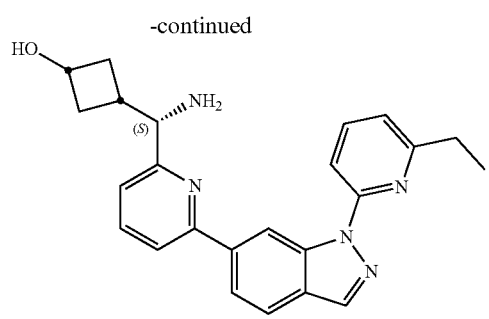

The preparation of (1R,3s)-3-((S)-amino(6-(1-(6-ethylpyridin-2-yl)-1H-indazol-6-yl)pyridin-2-yl)methyl)cyclobutanol was similar to that of cis 3-((S)-amino(6-(1-(6-(hydroxymethyl)pyrazin-2-yl)-1H-indazol-6-yl)pyridin-2-yl)methyl)cyclobutanol (Example 9, Step 6) to give 35 mg as a white solid, Y: 56%. ESI-MS (M+H)+: 400.2. HPLC: 100%. $^1$H NMR (400 MHz, CD$_3$OD) δ: 9.63 (s, 1H), 8.30 (s, 1H), 8.01 (d, J=8.0 Hz, 1H), 7.94-7.84 (m, 5H), 7.34-7.31 (m, 1H), 7.17 (d, J=6.4 Hz, 1H), 4.10-4.03 (m, 1H), 3.93 (d, J=8.4 Hz, 1H), 3.00 (q, J=7.6 Hz, 2H), 2.58-2.52 (m, 1H), 2.23-2.11 (m, 2H), 1.87-1.74 (m, 2H), 1.52 (t, J=8.0 Hz, 3H).

Example 13 (1R,3s)-3-((S)-amino(6-(1-(4-(trifluoromethyl)pyrimidin-2-yl)-1H-indazol-6-yl)pyridin-2-yl)methyl)cyclobutanol

Step 1. Synthesis of 6-bromo-1-(4-(trifluoromethyl)pyrimidin-2-yl)-1H-indazole

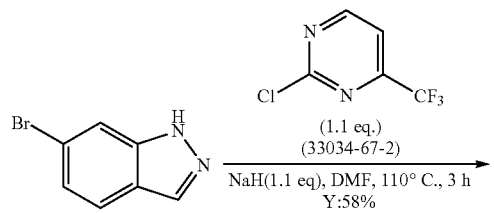

The preparation of 6-bromo-1-(4-(trifluoromethyl)pyrimidin-2-yl)-1H-indazole was similar to that of 6-bromo-1-(4-ethylpyrimidin-2-yl)-1H-indazole (Example 11, Step 1) to give 400 mg as a yellow solid. Y: 58%. ESI-MS (M+H)⁺: 343.1. ¹H NMR (400 MHz, CDCl₃) δ: 9.10 (d, J=4.8 Hz, 1H), 8.97 (s, 1H), 8.33 (s, 1H), 7.68 (d, J=8.4 Hz, 1H), 7.59-7.41 (m, 2H).

Step 2. Synthesis of 6-(4,4,5,5-tetramethyl-1,3,2-dioxaborolan-2-yl)-1-(4-(trifluoromethyl)pyrimidin-2-yl)-1H-indazole

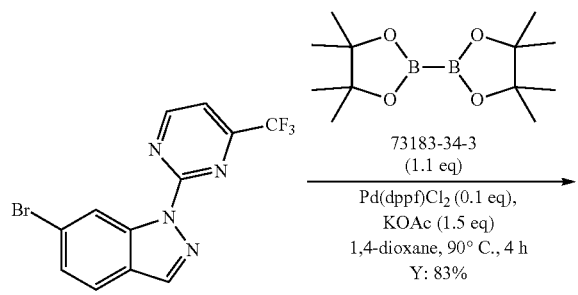

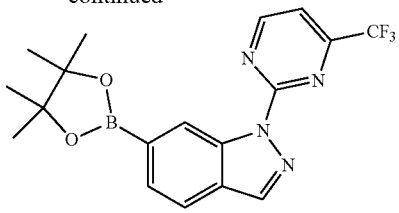

The preparation of 6-(4,4,5,5-tetramethyl-1,3,2-dioxaborolan-2-yl)-1-(4-(trifluoromethyl)pyrimidin-2-yl)-1H-indazole was similar to that of 1-(4-ethylpyrimidin-2-yl)-6-(4,4,5,5-tetramethyl-1,3,2-dioxaborolan-2-yl)-1H-indazole (Example 11, Step 2) to give 380 mg as a white solid. Y: 83%. ESI-MS (M+H)⁺: 391.2.

Step 3. Synthesis of (R)—N—((S)-((1s,3R)-3-hydroxycyclobutyl)(6-(1-(4-(trifluoromethyl)pyrimidin-2-yl)-1H-indazol-6-yl)pyridin-2-yl)methyl)-2-methylpropane-2-sulfinamide

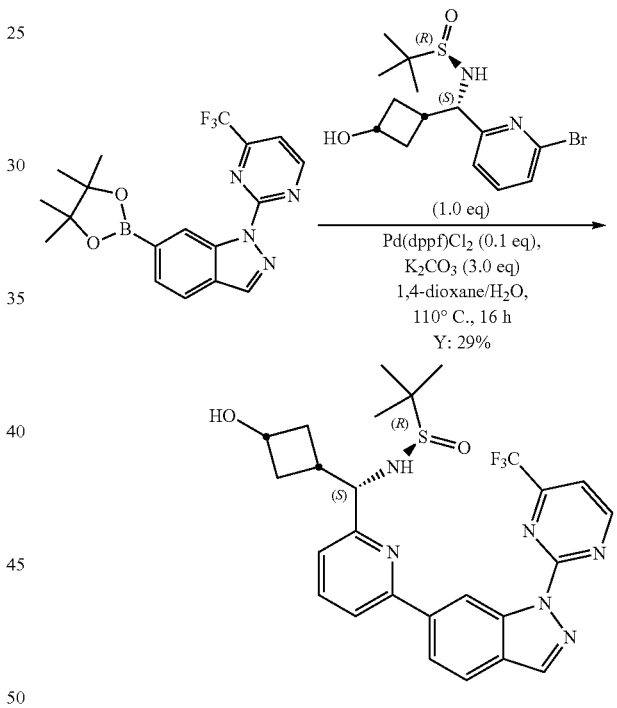

To a solution of 6-(4,4,5,5-tetramethyl-1,3,2-dioxaborolan-2-yl)-1-(4-(trifluoromethyl)pyrimidin-2-yl)-1H-indazole (108 mg, 0.28 mmol, 1.0 eq) and (R)—N—((S)-(6-bromopyridin-2-yl)((1s,3R)-3-hydroxycyclobutyl)methyl)-2-methylpropane-2-sulfinamide Example 10 step 3) 100 mg, 0.28 mmol, 1.0 eq) in 1,4-dioxane/H₂O (10/1, 22 mL) were added Pd(dppf)Cl₂.DCM (23 mg, 0.028 mmol, 1.0 eq) and K₂CO₃ (115 mg, 0.83 mmol, 3.0 eq). The mixture was stirred at 110° C. under N₂ for 16 h. After cooling to rt, diluted with water (100 mL) and extracted with EA (30 mL×3). The combined organic fractions were washed with brine, dried and evaporated. The residue was purified by pre-TLC (DCM/MeOH=30/1) to give (R)—N—((S)-((1s,3R)-3-hydroxycyclobutyl)(6-(1-(4-(trifluoromethyl)pyrimidin-2-yl)-1H-indazol-6-yl)pyridin-2-yl)methyl)-2-methylpropane-2-sulfinamide (40 mg, Y: 29%) as a yellow solid. ESI-MS (M+H)⁺: 545.2.

Step 4. Synthesis of (1R,3s)-3-((S)-amino(6-(1-(4-(trifluoromethyl)pyrimidin-2-yl)-1H-indazol-6-yl)pyridin-2-yl)methyl)cyclobutanol

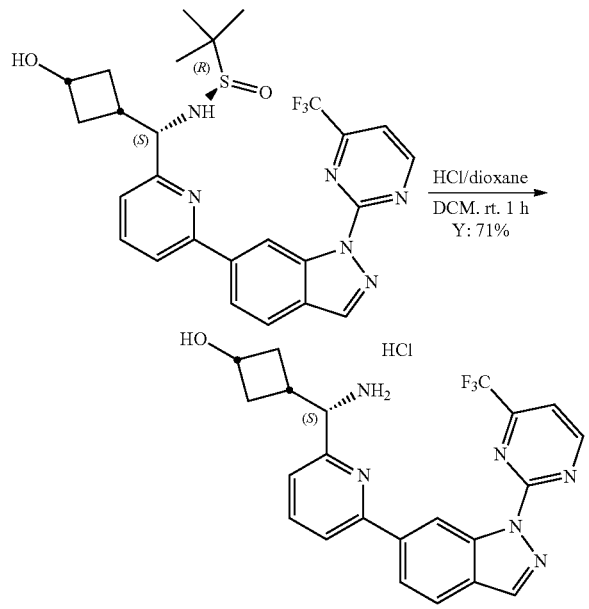

To a solution of (R)—N—((S)-((1s,3R)-3-hydroxycyclobutyl)(6-(1-(4-(trifluoromethyl)pyrimidin-2-yl)-1H-indazol-6-yl)pyridin-2-yl)methyl)-2-methylpropane-2-sulfinamide (40 mg, 0.073 mmol, 1.0 eq) in DCM (10 mL) was added 4 M HCl/dioxane (2 mL, excess). The mixture was stirred at rt for 1 h. The precipitate was filtered and washed with DCM, dried in vacuo to give (1R,3s)-3-((S)-amino(6-(1-(4-(trifluoromethyl)pyrimidin-2-yl)-1H-indazol-6-yl)pyridin-2-yl)methyl)cyclobutanol (25 mg, Y: 71%) as a yellow solid. ESI-MS (M+H)$^+$: 441.2. HPLC: 100%. $^1$H NMR (400 MHz, CD$_3$OD)(S: 9.41 (s, 1H), 9.29-9.16 (m, 1H), 8.61-8.51 (m, 1H), 8.28 (d, J=8.4 Hz, 1H), 8.04-8.03 (m, 3H), 7.83-7.77 (m, 1H), 7.50-7.45 (m, 1H), 4.49 (d, J=9.2 Hz, 1H), 4.18-4.11 (m, 1H), 2.67-2.59 (m, 1H), 2.43-2.37 (m, 1H), 2.28-2.21 (m, 1H), 1.98-1.86 (m, 2H).

Example 14 cis-3-((S)-amino(6-(1-(6-(difluoromethyl)pyridin-2-yl)-1H-indazol-6-yl)pyridin-2-yl)methyl)cyclobutanol

Step 2. Synthesis of 6-(6-bromo-1H-indazol-1-yl)picolinaldehyde

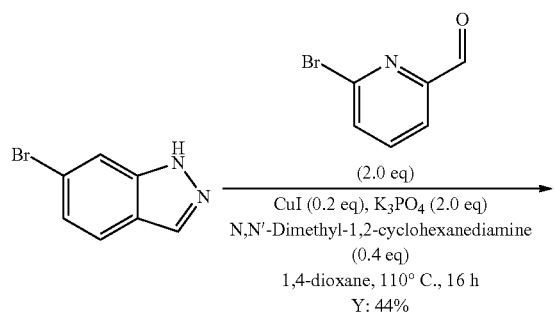

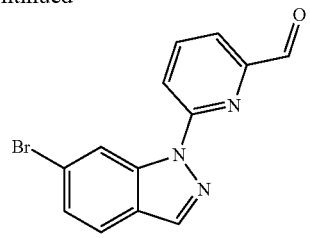

To a mixture of 6-bromo-1H-indazole (3 g, 15.3 mmol, 1.0 eq), 6-bromopicolinaldehyde (5.6 g, 30.6 mmol, 2.0 eq) and N,N'-Dimethyl-1,2-cyclohexanediamine (852 mg, 6 mmol, 0.4 eq) in 1,4-dioxane (50 mL) were added CuI (570 mg, 3 mmol, 0.2 eq) and K$_3$PO$_4$ (6.5 g, 30.6 mmol, 2.0 eq). The mixture was stirred at 110° C. for 16 h under N$_2$. After concentration, the residue was purified by silica gel chromatography with PE/EA (10/1) as eluent to give 6-(6-bromo-1H-indazol-1-yl)picolinaldehyde (2 g, Y: 44%) as a yellow solid. ESI-MS (M+H)$^+$: 302.1.

Step 2. Synthesis of 6-bromo-1-(6-(difluoromethyl)pyridin-2-yl)-1H-indazole

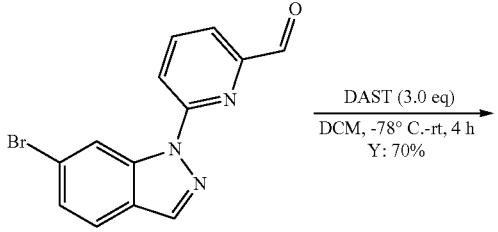

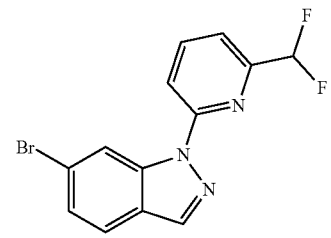

To a solution of 6-(6-bromo-1H-indazol-1-yl)picolinaldehyde (2 g, 6.6 mmol, 1.0 eq) in DCM (30 mL) was slowly added DAST (3.2 g, 19.8 mmol, 3.0 eq) at −78° C. The mixture was stirred from −78° C. to rt for 4 h. The reaction was quenched by pouring it into ice water and by washing the organic layer thoroughly with saturated sodium bicarbonate solution, followed by water. The solution was evaporated under reduced pressure to give 6-bromo-1-(6-(difluoromethyl)pyridin-2-yl)-1H-indazole (1.5 g, Y: 70%) as a brown solid. ESI-MS (M+H)$^+$: 324.1.

Step 3. Synthesis of 1-(6-(difluoromethyl)pyridin-2-yl)-6-(4,4,5,5-tetramethyl-1,3,2-dioxaborolan-2-yl)-1H-indazole

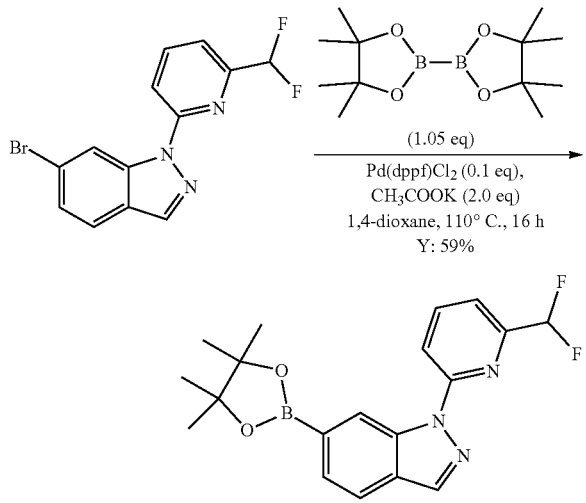

A mixture of 6-bromo-1-(6-(difluoromethyl)pyridin-2-yl)-1H-indazole (1.5 g, 4.6 mmol, 1.0 eq), 4,4,4',4',5,5,5',5'-octamethyl-2,2'-bi(1,3,2-dioxaborolane) (1.2 g, 4.9 mmol, 1.05 eq) and CH₃COOK (902 mg, 9.2 mmol, 2.0 eq) in 1,4-dioxane (20 mL) was stirred while purging N₂ at rt for 10 min. To this system was added Pd(dppf)Cl₂ (375 mg, 0.46 mmol, 0.1 eq) and heated to 110° C. for 16 h. After concentration, the residue was purified by silica gel chromatography with PE/EA (100/1) as eluent to give 1-(6-(difluoromethyl)pyridin-2-yl)-6-(4,4,5,5-tetramethyl-1,3,2-dioxaborolan-2-yl)-1H-indazole (1 g, Y: 59%) as a yellow solid. ESI-MS (M+H)⁺: 372.1. ¹H NMR (400 MHz, CDCl₃) δ: 9.23 (s, 1H), 8.21 (s, 1H), 8.15 (d, J=8.0 Hz, 1H), 7.96 (t, J=8.0 Hz, 1H), 7.77 (d, J=8.0 Hz, 1H), 7.71 (d, J=8.0 Hz, 1H), 7.49 (d, J=7.6 Hz, 1H), 6.93-6.65 (m, 1H), 1.40 (s, 12H).

Step 4. Synthesis of (R)—N—((S)-(6-(1-(6-(difluoromethyl)pyridin-2-yl)-1H-indazol-6-yl)pyridin-2-yl)(cis-3-hydroxycyclobutyl)methyl)-2-methylpropane-2-sulfinamide

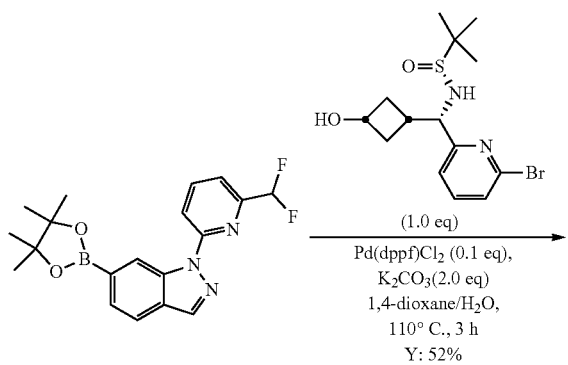

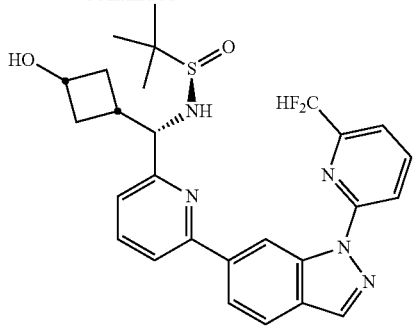

The preparation of (R)—N—((S)-(6-(1-(6-(difluoromethyl)pyridin-2-yl)-1H-indazol-6-yl)pyridin-2-yl)((cis-3-hydroxycyclobutyl)methyl)-2-methylpropane-2-sulfinamide was similar to that of (R)—N—((S)-((1s,3R)-3-hydroxycyclobutyl)(6-(1-(6-(trifluoromethyl)pyridin-2-yl)-1H-indazol-6-yl)pyridin-2-yl)methyl)-2-methylpropane-2-sulfinamide (Example 10, Step 4) to give 110 mg as a yellow solid, Y: 52%. ESI-MS (M+H)⁺: 526.2.

Step 5. Synthesis of cis-3-((S)-amino(6-(1-(6-(difluoromethyl)pyridin-2-yl)-1H-indazol-6-yl)pyridin-2-yl)methyl)cyclobutanol

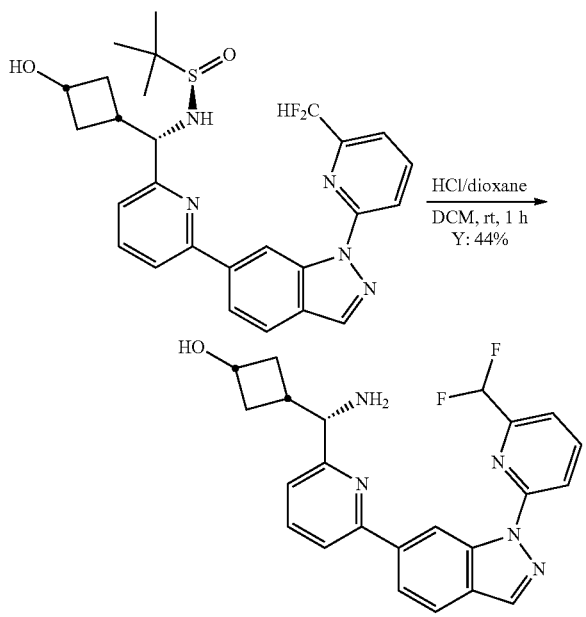

The preparation of cis-3-((S)-amino(6-(1-(6-(difluoromethyl)pyridin-2-yl)-1H-indazol-6-yl)pyridin-2-yl)methyl)cyclobutanol was similar to that of (1R,3s)-3-((S)-amino(6-(1-(4-(trifluoromethyl)pyrimidin-2-yl)-1H-indazol-6-yl)pyridin-2-yl)methyl)cyclobutanol (Example 13, Step 4) to give 39 mg as a white solid, Y: 44%. ESI-MS (M+H)⁺: 422.1. HPLC: 100%. ¹H NMR (400 MHz, CD₃OD) δ: 9.63 (s, 1H), 8.34 (s, 1H), 8.22 (d, J=8.4 Hz, 1H), 8.11 (t, J=8.0 Hz, 1H), 8.06 (d, J=8.4 Hz, 1H), 7.95-7.89 (m, 3H), 7.55 (d, J=7.6 Hz, 1H), 7.33-7.31 (m, 1H), 7.08-6.80 (m, 1H), 4.11-4.04 (m, 1H), 3.95 (d, J=9.2 Hz, 1H), 2.59-2.55 (m, 1H), 2.24-2.12 (m, 2H), 1.88-1.76 (m, 2H).

Example 15 (1R,3s)-3-((S)-amino(6-(1-(6-eth-ylpyrazin-2-yl)-1H-indazol-6-yl)pyridin-2-yl)methyl)cyclobutanol Step 1. Synthesis of 2-chloro-6-ethylpyrazine

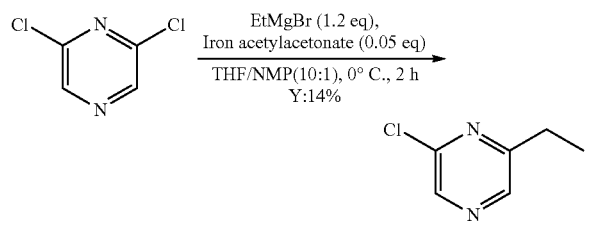

To a solution of 2,6-dichloropyrazine (4.0 g, 27.0 mmol, 1.0 eq) and Iron acetylacetonate (477 mg, 1.35 mmol, 0.05 eq) in THF/NMP (20 mL/2 mL) was slowly added EtMgBr (1.0 M in THF, 32.4 mL, 32.4 mmol, 1.2 eq) at 0° C. The mixture was stirred at 0° C. for 3 h. The mixture was quenched with H$_2$O (50 mL) and extracted with EA (50 mL×3). The combined organic fractions were dried over Na$_2$SO$_4$, filtrated and concentrated. The residue was purified by silica gel chromatography (PE/EA=8/1) to give 2-chloro-6-ethylpyrazine (520 mg, Y: 14%) as brown oil. ESI-MS (M+H)$^+$: 143.1. $^1$H NMR (400 MHz, CDCl$_3$) δ: 8.43 (s, 1H), 8.37 (s, 1H), 2.84 (q, J=7.6 Hz, 2H), 1.34 (t, J=7.6 Hz, 3H).

Step 2. Synthesis of 6-bromo-1-(6-ethylpyrazin-2-yl)-1H-indazole

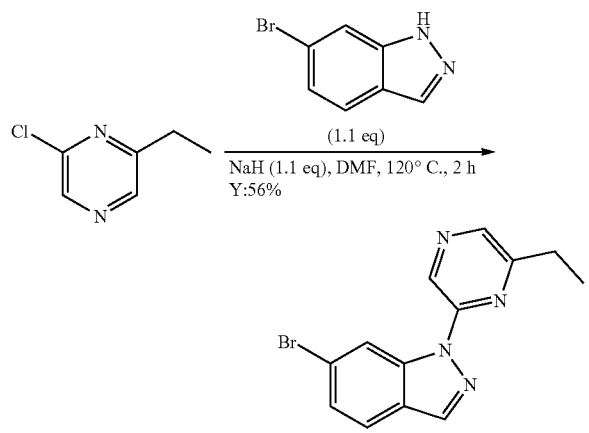

A mixture of 2-chloro-6-ethylpyrazine (520 mg, 3.7 mmol, 1.0 eq), 6-bromo-1H-indazole (798 mg, 4.1 mmol, 1.1 eq) and NaH (164 mg, 4.1 mmol, 1.1 eq) in DMF (10 mL) was stirred while purging N$_2$ at 120° C. for 2 h. The mixture was diluted with EA (100 mL) and washed with H$_2$O (50 mL×3). The organic phase was dried over Na$_2$SO$_4$. After filtration and concentration, the residue was purified by silica gel chromatography (PE/EA=10/1) to give 6-bromo-1-(6-ethylpyrazin-2-yl)-1H-indazole (620 mg, Y: 56%) as a yellow solid. ESI-MS (M+H)$^+$: 303.1. $^1$H NMR (400 MHz, CDCl$_3$) δ: 9.20 (s, 1H), 9.03 (s, 1H), 8.34 (s, 1H), 8.20 (s, 1H), 7.65 (d, J=8.4 Hz, 1H), 7.43 (d, J=8.4 Hz, 1H), 2.97 (q, J=7.6 Hz, 2H), 1.48 (t, J=7.6 Hz, 3H).

Step 3. Synthesis of 1-(6-ethylpyrazin-2-yl)-6-(4,4,5,5-tetramethyl-1,3,2-dioxaborolan-2-yl)-1H-indazole

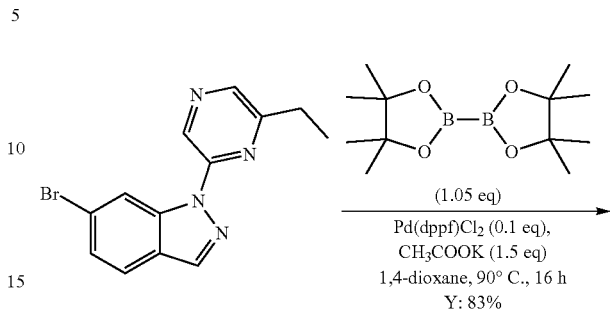

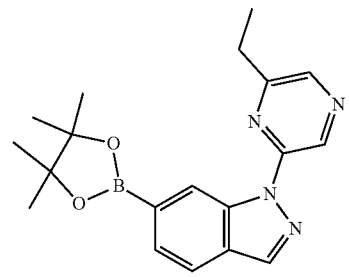

A mixture of 6-bromo-1-(6-ethylpyrazin-2-yl)-1H-indazole (250 mg, 0.83 mmol, 1.0 eq), 4,4,4',4',5,5,5',5'-octamethyl-2,2'-bi(1,3,2-dioxaborolane) (221 mg, 0.87 mmol, 1.05 eq) and CH$_3$COOK (122 mg, 1.25 mmol, 1.5 eq) in 1,4-dioxane (30 mL) was stirred while purging N$_2$ at rt for 10 min. To this system was added Pd(dppf)Cl$_2$ (65 mg, 0.08 mmol, 0.1 eq) and heated to 90° C. for 16 h. After concentration, the residue was purified by silica gel chromatography (PE/EA=10/1) to give 1-(6-ethylpyrazin-2-yl)-6-(4,4,5,5-tetramethyl-1,3,2-dioxaborolan-2-yl)-1H-indazole (240 mg, Y: 83%) as a yellow solid. ESI-MS (M+H)$^+$: 351.2.

Step 4. Synthesis of (R)—N—((S)-(6-(1-(6-ethylpyrazin-2-yl)-1H-indazol-6-yl)pyridin-2-yl)((1s,3R)-3-hydroxycyclobutyl)methyl)-2-methylpropane-2-sulfinamide

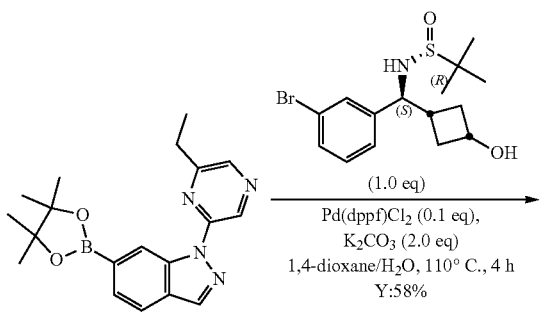

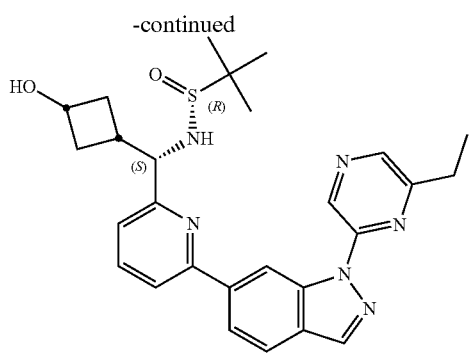

A mixture of 1-(6-ethylpyrazin-2-yl)-6-(4,4,5,5-tetramethyl-1,3,2-dioxaborolan-2-yl)-1H-indazole (240 mg, 0.69 mmol, 1.0 eq), (R)—N—((S)-(6-bromopyridin-2-yl)((1s,3R)-3-hydroxycyclobutyl)methyl)-2-methylpropane-2-sulfinamide (Example 10, Step 3) 247 mg, 0.69 mmol, 1.0 eq) and $K_2CO_3$ (190 g, 1.38 mmol, 2.0 eq) in 1, 4-dioxane/$H_2O$ (30 mL/0.5 mL) was stirred while purging $N_2$ at rt for 10 min. To this system was added Pd(dppf)$Cl_2$ (57 mg, 0.07 mmol, 0.1 eq) and heated to 110° C. for 4 h. After concentration, the residue was purified by silica gel chromatography (EA) to give (R)—N—((S)-(6-(1-(6-ethylpyrazin-2-yl)-1H-indazol-6-yl)pyridin-2-yl)((1s,3R)-3-hydroxycyclobutyl)methyl)-2-methylpropane-2-sulfinamide (200 mg, Y: 58%) as a yellow solid. ESI-MS (M+H)$^+$: 505.2.

Step 5. Synthesis of (1R,3s)-3-((S)-amino(6-(1-(6-ethylpyrazin-2-yl)-1H-indazol-6-yl)pyridin-2-yl)methyl)cyclobutanol

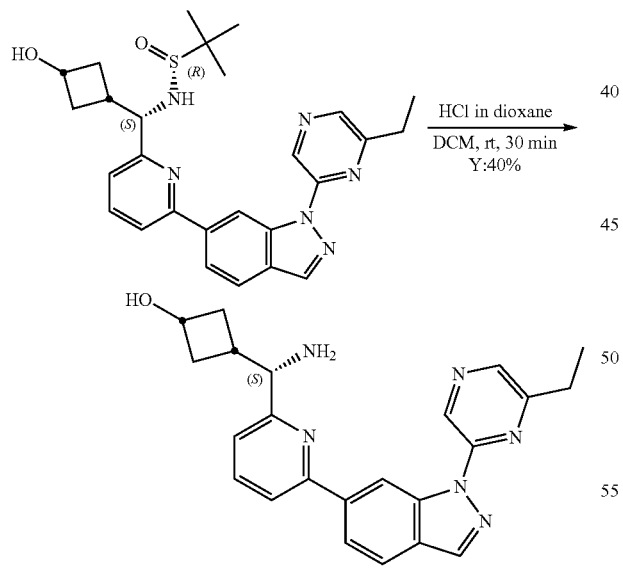

To a solution of (R)—N—((S)-(6-(1-(6-ethylpyrazin-2-yl)-1H-indazol-6-yl)pyridin-2-yl)((1s,3R)-3-hydroxycyclobutyl)methyl)-2-methylpropane-2-sulfinamide (200 mg, 0.4 mmol, 1.0 eq) in DCM (10 mL) was added HCl in dioxane (1 mL, 4 M, excess). The mixture was stirred at rt for 30 min. After concentration, the residue was dissolved in THF, adjusted pH=7-8 with NaOH solution and extracted with EA (3×60 mL). The combined organic phase was washed with brine and dried over $Na_2SO_4$. After filtration and concentration, the residue was purified by prep-HPLC ($CH_3CN$/0.05% $NH_4OH$ in $H_2O$=0%-100%) to give (1R,3s)-3-((S)-amino(6-(1-(6-ethylpyrazin-2-yl)-1H-indazol-6-yl)pyridin-2-yl)methyl)cyclobutanol (64 mg, Y: 40%) as a white solid. ESI-MS (M+H)$^+$: 401.2. HPLC: 100%. $^1$H NMR (400 MHz, $CD_3OD$) δ: 9.53 (s, 1H), 9.17 (s, 1H), 8.38 (d, J=4.0 Hz, 2H), 8.08 (d, J=8.4 Hz, 1H), 7.97-7.87 (m, 3H), 7.37-7.35 (m, 1H), 4.11-4.04 (m, 1H), 3.99 (d, J=8.4 Hz, 1H), 3.05 (q, J=7.6 Hz, 2H), 2.60-2.53 (m, 1H), 2.24-2.13 (m, 2H), 1.89-1.75 (m, 2H), 1.56 (t, J=7.6 Hz, 3H).

Example 16 (1R,3s)-3-((S)-amino(6-(1-(6-(fluoromethyl)pyridin-2-yl)-1H-indazol-6-yl)pyridin-2-yl)methyl)cyclobutanol Step 1. Synthesis of 6-bromo-1-(6-(fluoromethyl)pyridin-2-yl)-1H-indazole

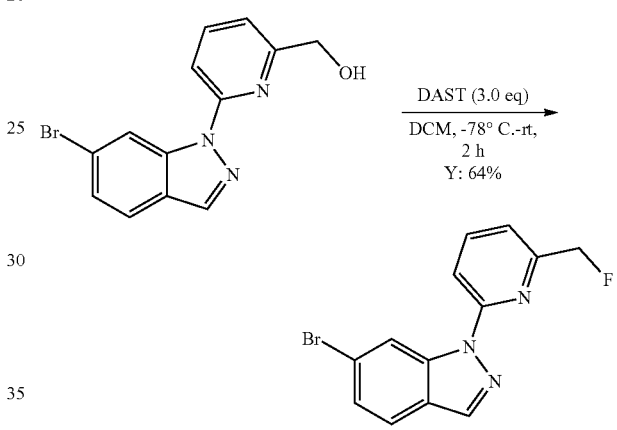

To a solution of (6-(6-bromo-1H-indazol-1-yl)pyridin-2-yl)methanol (Example 1, Step 7, 1.0 g, 3.3 mmol, 1.0 eq) in DCM (100 mL) was added DAST (1.6 g, 9.9 mmol, 3.0 eq) at −78° C. The mixture was warmed to rt and stirred for 2 h. After concentration, the residue was purified by silica gel chromatography using PE/EA (5/1) as eluent to give 6-bromo-1-(6-(fluoromethyl)pyridin-2-yl)-1H-indazole (640 mg, Y: 64%) as a yellow solid. ESI-MS (M+H)$^+$: 306.0. $^1$H NMR (400 MHz, CDCL3) δ: 8.99 (s, 1H), 8.15 (s, 1H), 7.98 (d, J=8.4 Hz, 1H), 7.89 (t, J=7.6 Hz, 1H), 7.62 (d, J=8.4 Hz, 1H), 7.39 (d, J=8.4 Hz, 1H), 7.33 (d, J=7.2 Hz, 1H), 5.60 (d, J=47.2 Hz, 2H).

Step 2. Synthesis of 1-(6-(fluoromethyl)pyridin-2-yl)-6-(4,4,5,5-tetramethyl-1,3,2-dioxaborolan-2-yl)-1H-indazole

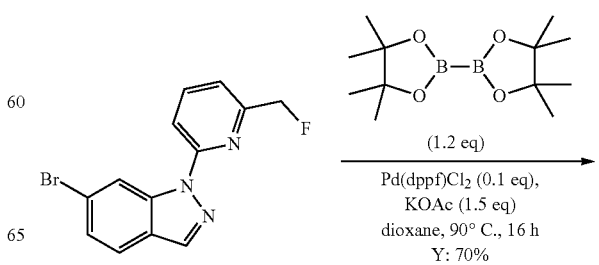

-continued

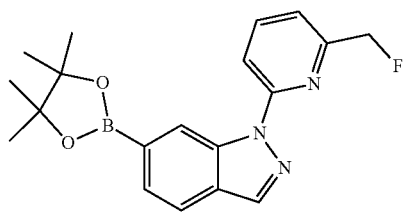

A mixture of 6-bromo-1-(6-(fluoromethyl)pyridin-2-yl)-1H-indazole (320 mg, 1.05 mmol, 1.0 eq), 4,4,4',4',5,5,5',5'-octamethyl-2,2'-bi(1,3,2-dioxaborolane) (320 mg, 1.26 mmol, 1.2 eq) and CH₃COOK (155 mg, 1.58 mmol, 1.5 eq) in dioxane (6 mL) was stirred while purging N₂ at rt for 10 min. To this system was added Pd(dppf)Cl₂ (82 mg, 0.1 mmol, 0.1 eq) and heated to 90° C. for 16 h. The mixture was diluted with EA (20 mL) and washed with brine (20 mL). The organic was dried over Na₂SO₄. After filtration and concentration, 260 mg of 1-(6-(fluoromethyl)pyridin-2-yl)-6-(4,4,5,5-tetramethyl-1,3,2-dioxaborolan-2-yl)-1H-indazole as brown oil was obtained which was used for next step without further purification. Y: 70%. ESI-MS (M+H)⁺: 354.1.

Step 3. Synthesis of (R)—N—((S)-(6-(1-(6-(fluoromethyl)pyridin-2-yl)-1H-indazol-6-yl)pyridin-2-yl)((1s,3R)-3-hydroxycyclobutyl)methyl)-2-methylpropane-2-sulfinamide

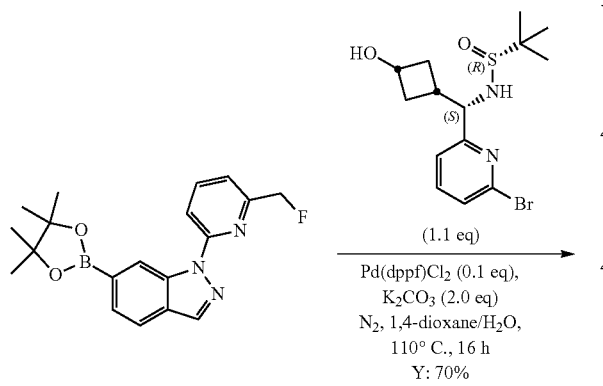

A mixture of 1-(6-(fluoromethyl)pyridin-2-yl)-6-(4,4,5,5-tetramethyl-1,3,2-dioxaborolan-2-yl)-1H-indazole (65 mg, 0.18 mmol, 1.0 eq), (R)—N—((S)-(6-bromopyridin-2-yl)((1s,3R)-3-hydroxycyclobutyl)methyl)-2-methylpropane-2-sulfinamide (Example 10, step 3, 65 mg, 0.18 mmol, 1.0 eq) and K₂CO₃ (50 mg, 0.36 mmol, 2.0 eq) in 1, 4-dioxane/H₂O (4/1, 5 mL) was stirred while purging N₂ at rt for 10 min. To this system was added Pd(dppf)Cl₂ (16 mg, 0.02 mmol, 0.1 eq) and heated to 110° C. for 2 h. The mixture was purified by silica gel chromatography using PE/EA (1/1) as eluent to give (R)—N—((S)-(6-(1-(6-(fluoromethyl)pyridin-2-yl)-1H-indazol-6-yl)pyridin-2-yl)((1s,3R)-3-hydroxycyclobutyl)methyl)-2-methylpropane-2-sulfinamide as a yellow solid. 65 mg, Y: 70%. ESI-MS (M+H)⁺: 508.2.

Step 4. Synthesis of (1R,3s)-3-((S)-amino(6-(1-(6-(fluoromethyl)pyridin-2-yl)-1H-indazol-6-yl)pyridin-2-yl)methyl)cyclobutanol

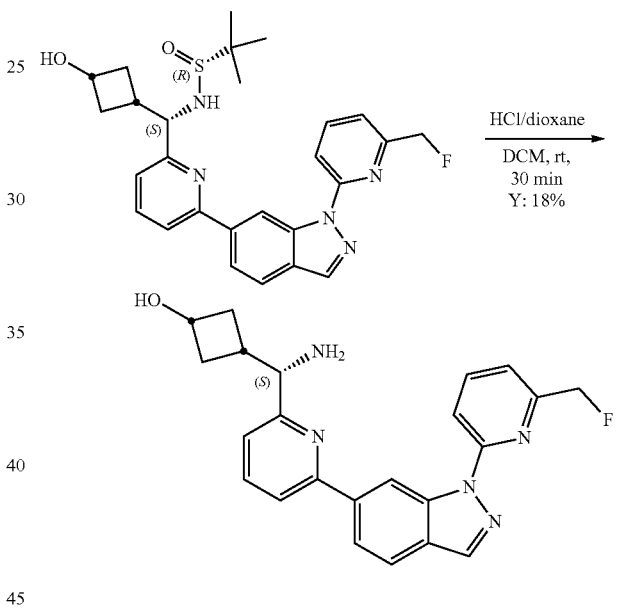

To a solution of (R)—N—((S)-(6-(1-(6-(fluoromethyl)pyridin-2-yl)-1H-indazol-6-yl)pyridin-2-yl)((1s,3R)-3-hydroxycyclobutyl)methyl)-2-methylpropane-2-sulfinamide (65 mg, 0.13 mmol, 1.0 eq) in DCM (5 mL) was added HCl in dioxane (0.4 mL, excess). The mixture was stirred at rt for 30 min. The solvent was removed in vacuo. The residue was dissolved in THF, adjusted pH=7-8 with NaOH solution and extracted with EA (100 mL×2). The combined organic phase was washed with brine and dried over Na2SO4. After filtration and concentration, the residue was purified by prep-HPLC (CH₃CN/0.05% NH₄OH in H₂O=0%-100%) to give (1R,3s)-3-((S)-amino(6-(1-(6-(fluoromethyl)pyridin-2-yl)-1H-indazol-6-yl)pyridin-2-yl)methyl)cyclobutanol as a yellow solid. 9 mg, Y: 18%, ESI-MS (M+H)⁺: 404.1. HPLC: 100%. ¹H NMR (400 MHz, CD₃OD) δ: 9.57 (s, 1H), 8.30 (s, 1H), 8.05-7.97 (m, 3H), 7.92-7.85 (m, 3H), 7.37 (d, J=6.8 Hz, 1H), 7.31 (t, J=4.0 Hz, 1H), 5.61 (d, J=47.2 Hz, 1H), 4.08-4.04 (m, 1H), 3.93 (d, J=8.4 Hz, 1H), 2.55-2.53 (m, 1H), 2.21-2.13 (m, 2H), 1.84-1.76 (m, 2H).

Example 17 cis-3-((S)-amino(6-(1-(6-(hydroxymethyl)pyridin-2-yl)-1H-indazol-6-yl)pyrazin-2-yl)methyl)cyclobutanol Step 1. Synthesis of (cis-3-(tert-butyldimethylsilyloxy)cyclobutyl)methanol

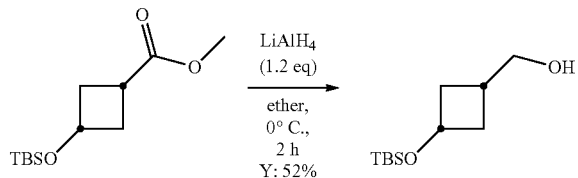 [SMILES: COC(=O)[C@H]1C[C@@H](O[Si](C)(C)C(C)(C)C)C1 ; CC(C)(C)[Si](C)(C)O[C@H]1C[C@@H](CO)C1]

To a solution of cis-methyl 3-(tert-butyldimethylsilyloxy)cyclobutanecarboxylate (Example 4, Step 2, 98 g, 0.402 mol) in ether (100 mL) was added a suspension of LiAlH₄ (18.3 g, 0.482 mol, 1.2 eq) in dry ether (500 mL) dropwise at 0° C. The mixture solution was stirred at 0° C. for 2 h, then quenched with H₂O (18 mL), 15% NaOH (18 mL) and H₂O (55 mL), then dried over Na₂SO₄. The solution was filtered and concentrated in vacuo to give (cis-3-(tert-butyldimethylsilyloxy)cyclobutyl)methanol (45 g, Y: 52%) as colorless oil. ESI-MS (M+H)⁺: 217.2. ¹H NMR (400 MHz, CDCl₃) δ: 4.16-4.10 (m, 1H), 3.59 (t, J=5.6 Hz, 2H), 2.37-2.30 (m, 2H), 1.95-1.91 (m, 1H), 1.69-1.62 (m, 2H), 1.43-1.41 (m, 1H), 0.88 (s, 9H), 0.04 (s, 6H).

Step 2. Synthesis of cis-3-(tert-butyldimethylsilyloxy)cyclobutanecarbaldehyde

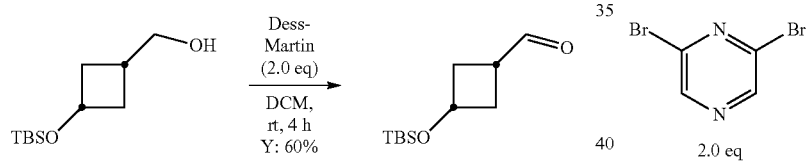

To a solution of ((cis-3-(tert-butyldimethylsilyloxy)cyclobutyl)methanol (60 g, 0.278 mol) in DCM (500 mL) was added Dess-Martin periodane (236 g, 0.556 mol, 2.0 eq) at 0° C. The mixture was stirred at rt under nitrogen for 4 h. The mixture was washed with brine, dried over Na₂SO₄, filtered, and the solvent evaporated in vacuo. The residue was purified by silica gel chromatography with PE/EA (10/1) to give cis-3-(tert-butyldimethylsilyloxy)cyclobutanecarbaldehyde as colorless oil (38 g, Y: 60%). ESI-MS (M+H)⁺: 215.2. ¹H NMR (400 MHz, CDCl₃) δ: 9.64 (d, J=2.8 Hz, 1H), 4.30-4.23 (m, 1H), 2.64-2.55 (m, 1H), 2.46-2.41 (m, 2H), 2.19-2.11 (m, 2H), 0.89 (s, 9H), 0.06 (s, 6H).

Step 3. Synthesis of (R)—N-((cis-3-(tert-butyldimethylsilyloxy)cyclobutyl)methylene)-2-methylpropane-2-sulfinamide

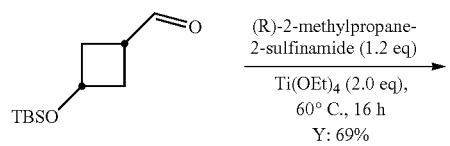

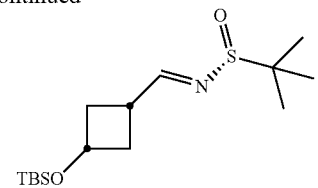

To a solution of cis-3-(tert-butyldimethylsilyloxy)cyclobutanecarbaldehyde (27 g, 0.126 mol) in THF (300 mL) were added (R)-2-methylpropane-2-sulfinamide (18.3 g, 0.151 mol, 1.2 eq) and Ti(OEt)₄ (58 g, 0.252 mol, 2.0 eq) at rt. The mixture was stirred at 60° C. for 16 h. The residue was purified by silica gel chromatography with PE/EA (5/1) to give (R)—N-((cis-3-(tert-butyldimethylsilyloxy)cyclobutyl)methylene)-2-methylpropane-2-sulfinamide as colorless oil. 27.5 g; Y: 69%. ESI-MS (M+H)⁺: 318.2. ¹H NMR (400 MHz, CDCl₃) δ: 8.05 (d, J=4.8 Hz, 1H), 4.28-4.24 (m, 1H), 2.82-2.80 (m, 1H), 2.56-2.49 (m, 2H), 2.14-2.08 (m, 2H), 1.20 (s, 9H), 0.89 (s, 9H), 0.05 (s, 6H).

Step 4. Synthesis of (R)—N—((S)-(6-bromopyrazin-2-yl)(cis-3-(tert-butyldimethylsilyloxy)cyclobutyl)methyl)-2-methylpropane-2-sulfinamide

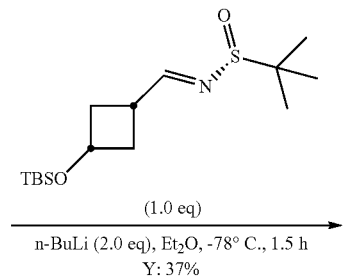

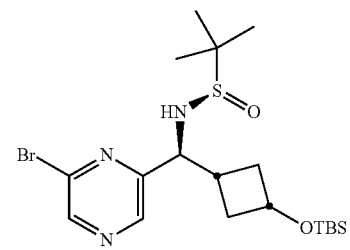

To a solution of 2,6-dibromopyrazine (750 mg, 3.18 mmol, 2.0 eq) in dry Et₂O (50 mL) was added n-BuLi (2.5 M, 1.3 mL, 3.18 mmol, 2.0 eq) at −78° C. The mixture was stirred at −78° C. for 30 min. Then (R)—N-((cis-3-(tert-butyldimethylsilyloxy)cyclobutyl)methylene)-2-methylpropane-2-sulfinamide (507 mg, 1.60 mmol, 1.0 eq) was added into the mixture and the mixture was stirred for another 1 h at −78° C. The reaction was quenched with H₂O (20 mL) and extracted with EA (50 mL×2). The combined organic phase was washed with brine and dried over Na₂SO₄. After filtration and concentration, the residue was purified by silica gel chromatography using PE/EA (1/1) as eluent to give (R)—N—((S)-(6-bromopyrazin-2-yl)(cis-3-(tert-butyldimethylsilyloxy)cyclobutyl)methyl)-2-methylpropane-2-sulfinamide as yellow oil. 280 mg, Y: 37%. ESI-MS (M+H)⁺: 476.1.

Step 5. Synthesis of (R)—N—((S)-(cis-3-(tert-butyldimethylsilyloxy)cyclobutyl)(6-(1-(6-((tert-butyldimethylsilyloxy)methyl)pyridin-2-yl)-1H-indazol-6-yl)pyrazin-2-yl)methyl)-2-methylpropane-2-sulfinamide

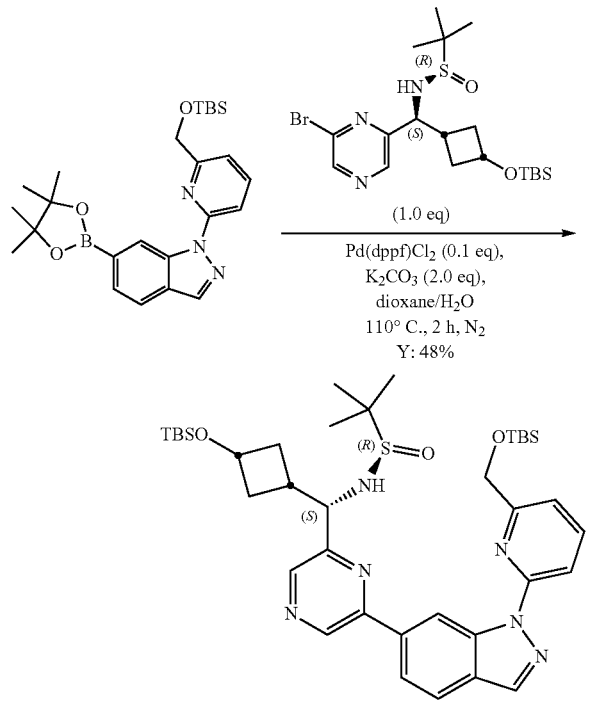

The preparation of (R)—N—((S)-(cis-3-(tert-butyldimethylsilyloxy)cyclobutyl)(6-(1-(6-((tert-butyldimethylsilyloxy)methyl)pyridin-2-yl)-1H-indazol-6-yl)pyrazin-2-yl)methyl)-2-methylpropane-2-sulfinamide was similar to that of (R)—N—((S)-(6-(1-(6-(fluoromethyl)pyridin-2-yl)-1H-indazol-6-yl)pyridin-2-yl)((1s,3R)-3-hydroxycyclobutyl)methyl)-2-methylpropane-2-sulfinamide (Example 16, Step 3) to give 170 mg as a yellow solid, Y: 48%. ESI-MS (M+H)+: 735.4.

Step 6. Synthesis of cis-3-((S)-amino(6-(1-(6-(hydroxymethyl)pyridin-2-yl)-1H-indazol-6-yl)pyrazin-2-yl)methyl)cyclobutanol

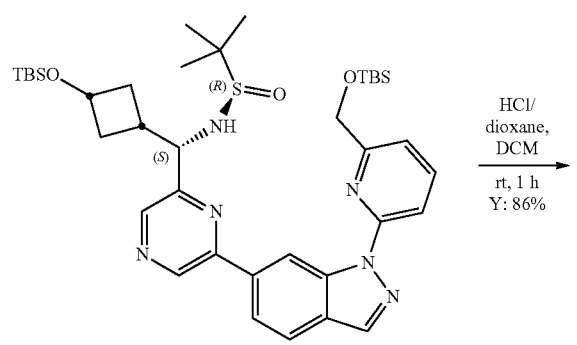

The preparation of cis-3-((S)-amino(6-(1-(6-(hydroxymethyl)pyridin-2-yl)-1H-indazol-6-yl)pyrazin-2-yl)methyl)cyclobutanol was similar to that of (1R,3s)-3-((S)-amino(6-(1-(6-(fluoromethyl)pyridin-2-yl)-1H-indazol-6-yl)pyridin-2-yl)methyl)cyclobutanol (Example 16, Step 4) to give 80 mg as a yellow solid, Y: 86%, ESI-MS (M+H)+: 403.2. HPLC: 100%. $^1$H NMR (400 MHz, CD$_3$OD) δ: 9.63-9.60 (m, 1H), 9.07-9.06 (m, 1H), 8.54 (s, 1H), 8.27-8.25 (m, 1H), 8.02-8.00 (m, 1H), 7.91-7.87 (m, 3H), 7.37-7.36 (m, 1H), 4.84 (s, 2H), 4.13-4.02 (m, 2H), 2.62-2.54 (m, 1H), 2.27-2.13 (m, 2H), 1.90-1.75 (m, 2H).

Example 18 cis-3-((S)-amino(6-(1-(6-(fluoromethyl)pyridin-2-yl)-1H-indazol-6-yl)pyrazin-2-yl)methyl)cyclobutanol Step 1. Synthesis of (R)—N—((S)-(cis-3-(tert-butyldimethylsilyloxy)cyclobutyl)(6-(1-(6-(fluoromethyl)pyridin-2-yl)-1H-indazol-6-yl)pyrazin-2-yl)methyl)-2-methylpropane-2-sulfinamide (containing 15% trans isomer)

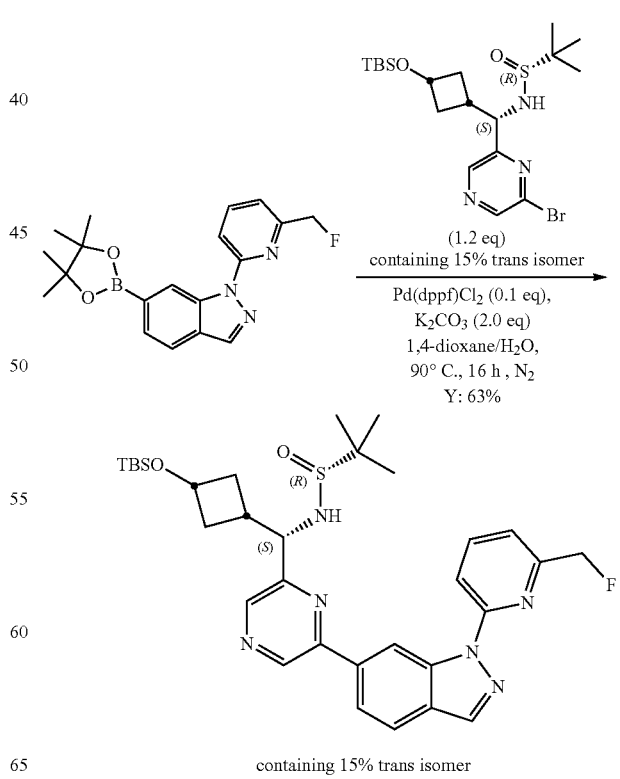

containing 15% trans isomer

A mixture of 1-(6-(fluoromethyl)pyridin-2-yl)-6-(4,4,5,5-tetramethyl-1,3,2-dioxaborolan-2-yl)-1H-indazole (Example 16, Step 2, 150 mg, 0.42 mmol, 1.0 eq), (R)—N—((S)-(6-bromopyrazin-2-yl)(cis-3-(tert-butyldimethylsilyloxy)cyclobutyl)methyl)-2-methylpropane-2-sulfinamide (Example 17, Step 4, 240 mg, 0.51 mmol, 1.0 eq) and K$_2$CO$_3$ (116 mg, 0.84 mmol, 2.0 eq) in 1,4-dioxane/H$_2$O (4/1, 10 mL) was stirred while purging N$_2$ at rt for 10 min. To this system was added Pd(dppf)Cl$_2$ (77 mg, 0.04 mmol, 0.1 eq) and heated to 90° C. for 16 h under N$_2$ atmosphere. After concentration, the residue was purified by silica gel chromatography using PE/EA (2/1) as eluent to give (R)—N—((S)-(cis-3-(tert-butyldimethylsilyloxy)cyclobutyl)(6-(1-(6-(fluoromethyl)pyridin-2-yl)-1H-indazol-6-yl)pyrazin-2-yl)methyl)-2-methylpropane-2-sulfinamide (containing 15% trans isomer). 166 mg, as a yellow solid, Y: 63%. ESI-MS (M+H)$^+$: 623.2.

Step 2. Synthesis of cis-3-((S)-amino(6-(1-(6-(fluoromethyl)pyridin-2-yl)-1H-indazol-6-yl)pyrazin-2-yl)methyl)cyclobutanol

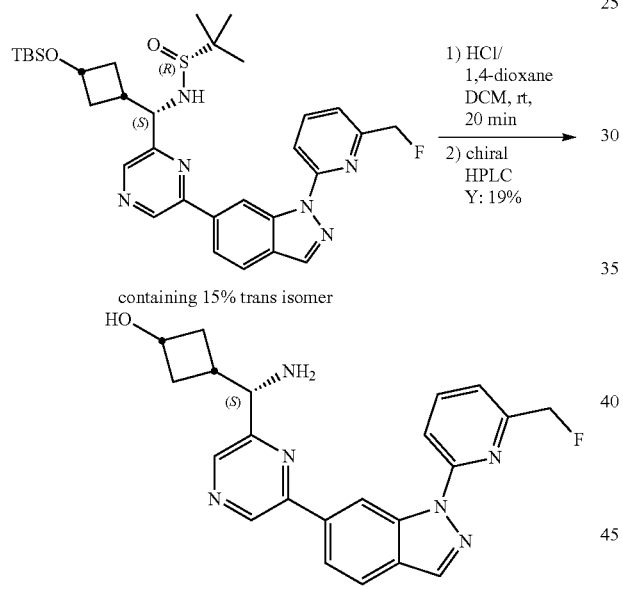

To a solution of (R)—N—((S)-(cis-3-(tert-butyldimethylsilyloxy)cyclobutyl)(6-(1-(6-(fluoromethyl)pyridin-2-yl)-1H-indazol-6-yl)pyrazin-2-yl)methyl)-2-methylpropane-2-sulfinamide (containing 15% trans isomer) (166 mg, 0.27 mmol, 1.0 eq) in DCM (5 mL) was added slowly HCl/1,4-dioxane (4 M, 0.5 mL, excess). Then the mixture was stirred at rt for 20 min. After filtration, the residue was purified by prep-HPLC (CH$_3$CN/0.05% TFA in H$_2$O=0%~100%) and prep-chiral HPLC to give cis-3-((S)-amino(6-(1-(6-(fluoromethyl)pyridin-2-yl)-1H-indazol-6-yl)pyrazin-2-yl)methyl)cyclobutanol. 21 mg, as a yellow solid, Y: 19%. ESI-MS (M+H)$^+$: 405.2. HPLC: 100%.

Preparative-SFC conditions Instrument: Gilson-281, Column: WHELK, Mobile phase: Hexane (0.1% DEA)/Ethanol (0.1% DEA)=80/20, Flow rate: 50 mL/min, Detection wavelength: 214&254 nm, Cycle time: 32 min, Sample solution: 80 mg dissolved in 5 mL Methanol, Injection volume: 0.5 mL $^1$H NMR (400 MHz, CD$_3$OD) δ: 9.63 (s, 1H), 9.28 (s, 1H), 8.68 (s, 1H), 8.36 (s, 1H), 8.15 (d, J=8.4 Hz, 1H), 8.07-7.99 (m, 3H), 7.40 (d, J=6.8 Hz, 1H), 5.65 (d, J=44.0 Hz, 2H), 4.62 (d, J=9.6 Hz, 1H), 4.14 (t, J=7.6 Hz, 1H), 2.64-2.60 (m, 1H), 2.41-2.24 (m, 2H), 2.01-1.86 (m, 2H).

Example 19 cis-3-((S)-amino(6-(1-(6-(trifluoromethyl)pyridin-2-yl)-1H-indazol-6-yl)pyrazin-2-yl)methyl)cyclobutanol Step 1. Synthesis of (R)—N—((S)-(cis-3-(tert-butyldimethylsilyloxy)cyclobutyl)(6-(1-(6-(trifluoromethyl)pyridin-2-yl)-1H-indazol-6-yl)pyrazin-2-yl)methyl)-2-methylpropane-2-sulfinamide (containing 15% trans isomer)

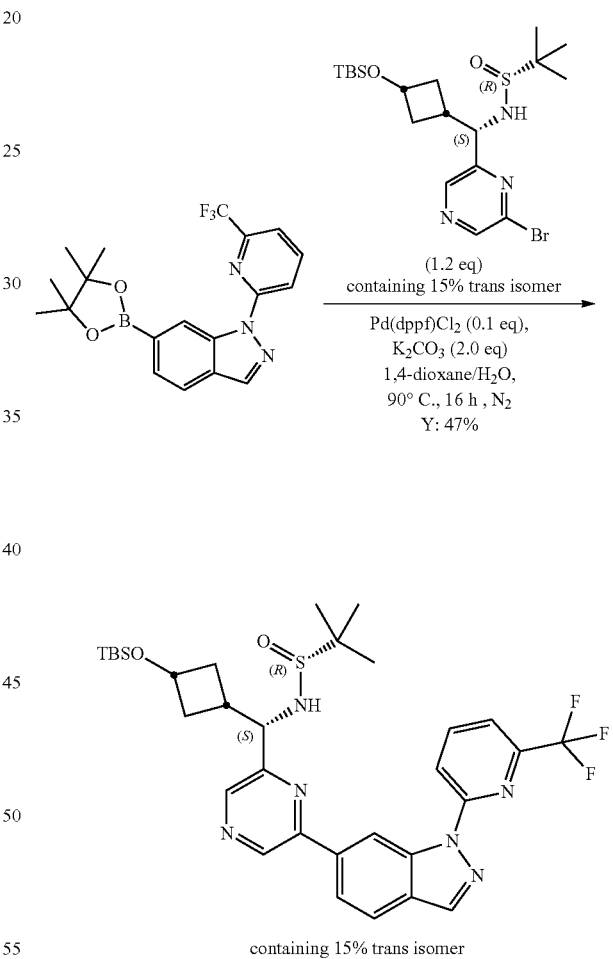

The preparation of (R)—N—((S)-(cis-3-(tert-butyldimethylsilyloxy)cyclobutyl)(6-(1-(6-(trifluoromethyl)pyridin-2-yl)-1H-indazol-6-yl)pyrazin-2-yl)methyl)-2-methylpropane-2-sulfinamide (containing 15% trans isomer) was similar to that of (R)—N—((S)-(cis-3-(tert-butyldimethylsilyloxy)cyclobutyl)(6-(1-(6-(fluoromethyl)pyridin-2-yl)-1H-indazol-6-yl)pyrazin-2-yl)methyl)-2-methylpropane-2-sulfinamide (Example 18, Step 1) (containing 15% trans isomer) to give 112 mg as yellow oil, Y: 47%. ESI-MS (M+H)$^+$: 659.3.

Step 2. Synthesis of cis-3-((S)-amino(6-(1-(6-(trifluoromethyl)pyridin-2-yl)-1H-indazol-6-yl)pyrazin-2-yl)methyl)cyclobutanol

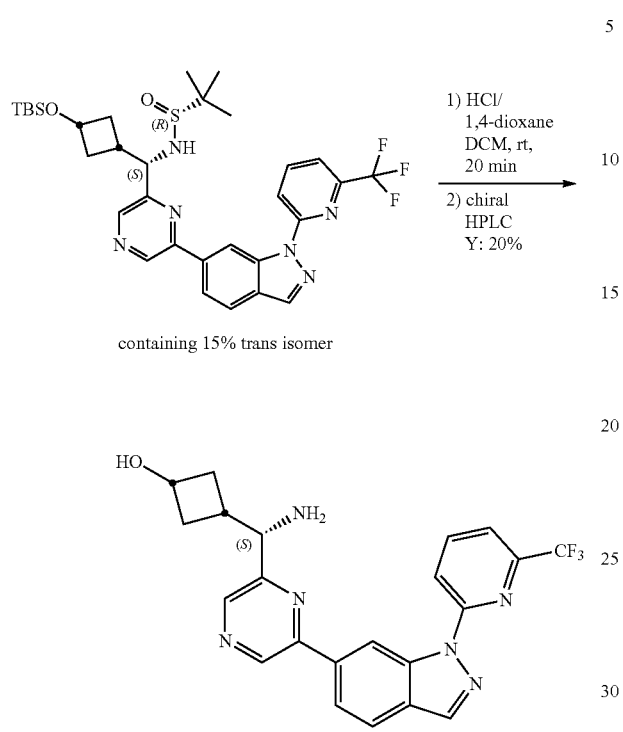

containing 15% trans isomer

The preparation of cis-3-((S)-amino(6-(1-(6-(trifluoromethyl)pyridin-2-yl)-1H-indazol-6-yl)pyrazin-2-yl)methyl)cyclobutanol was similar to that of cis-3-((S)-amino(6-(1-(6-(fluoromethyl)pyridin-2-yl)-1H-indazol-6-yl)pyrazin-2-yl)methyl)cyclobutanol (Example 18, Step 2) and purified by prep-chiral HPLC to give 15 mg as a yellow solid, Y: 20%. ESI-MS (M+H)$^+$: 441.2.

Preparative-SFC conditions Instrument: Gilson-281, Column: CE-3, Mobile Phase: n-Hexane (0.1% DEA)/EtOH (0.1% DEA)=80/20, Flow rate: 50 mL/min, Wavelength: 214 & 254 nm

Example 20 1-(6-(6-(6-((S)-amino(cis-3-hydroxycyclobutyl)methyl)pyridin-2-yl)-1H-indazol-1-yl)pyridin-2-yl)cyclopropanecarbonitrile

Step 1. Synthesis of 1-(6-(6-bromo-1H-indazol-1-yl)pyridin-2-yl)cyclopropanecarbonitrile

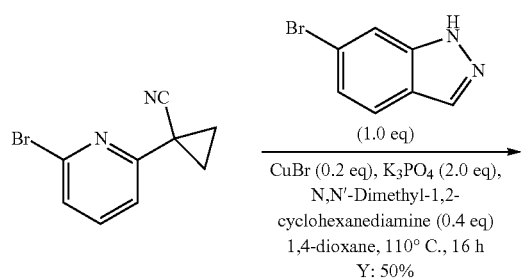

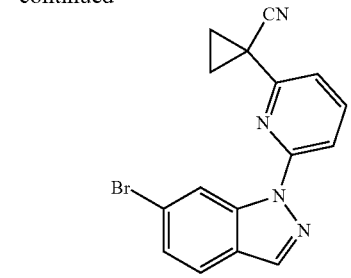

A mixture of 1-(6-bromopyridin-2-yl)cyclopropanecarbonitrile (300 mg, 1.35 mmol, 1.0 eq), 6-bromo-1H-indazole (263 mg, 1.35 mmol, 1.0 eq), K$_3$PO$_4$ (572 mg, 2.7 mmol, 2.0 eq), CuBr (39 mg, 0.27 mmol, 0.2 eq) and N,N'-Dimethyl-1,2-cyclohexanediamine (48 mg, 0.54 mmol, 0.4 eq) in 1,4-dioxane (20 mL) was stirred at 110° C. for 16 h under N$_2$ atmosphere. After concentration, the residue was purified by silica gel chromatography using PE/EA (5/1) as eluent to give 1-(6-(6-bromo-1H-indazol-1-yl)pyridin-2-yl)cyclopropanecarbonitrile. 230 mg, as a yellow solid, Y: 50%. ESI-MS (M+H)$^+$: 339.0

Step 2. Synthesis of 1-(6-(6-(4,4,5,5-tetramethyl-1,3,2-dioxaborolan-2-yl)-1H-indazol-1-yl)pyridin-2-yl)cyclopropanecarbonitrile

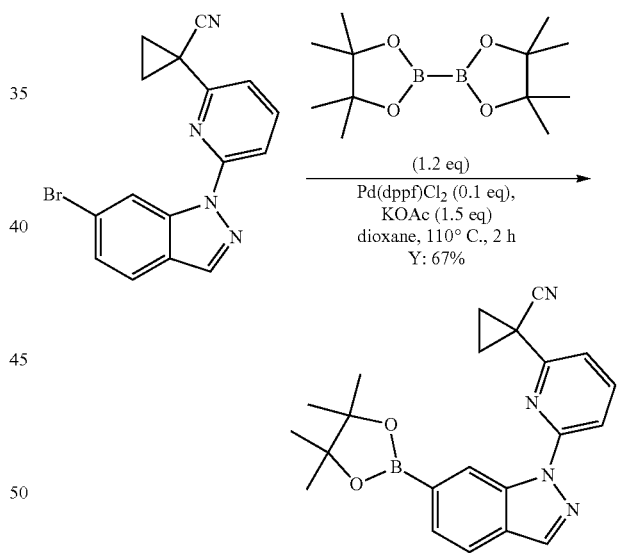

A mixture of 1-(6-(6-bromo-1H-indazol-1-yl)pyridin-2-yl)cyclopropanecarbonitrile (230 mg, 0.68 mmol, 1.0 eq), 4,4,4',4',5,5,5',5'-octamethyl-2,2'-bi(1,3,2-dioxaborolane) (207 mg, 0.82 mmol, 1.2 eq) and KOAc (133 mg, 1.36 mmol, 2.0 eq) in 1,4-dioxane (20 mL) was stirred while purging N$_2$ at rt for 10 min. To this system was added Pd(dppf)Cl$_2$ (62 mg, 0.068 mmol, 0.1 eq) and heated to 110° C. for 2 h. The mixture was diluted with EtOAc (50 mL) and washed with H$_2$O (50 mL) and brine (50 mL). The organic was dried (Na$_2$SO$_4$) and concentrated in vacuo to give 1-(6-(6-(4,4,5,5-tetramethyl-1,3,2-dioxaborolan-2-yl)-1H-indazol-1-yl)pyridin-2-yl)cyclopropanecarbonitrile. 175 mg as a yellow solid, Y: 67%. ESI-MS (M+H)$^+$: 387.2.

Step 3. Synthesis of (R)—N—((S)-(6-(1-(6-(1-cyanocyclopropyl)pyridin-2-yl)-1H-indazol-6-yl)pyridin-2-yl)((1s,3R)-3-hydroxycyclobutyl)methyl)-2-methylpropane-2-sulfinamide

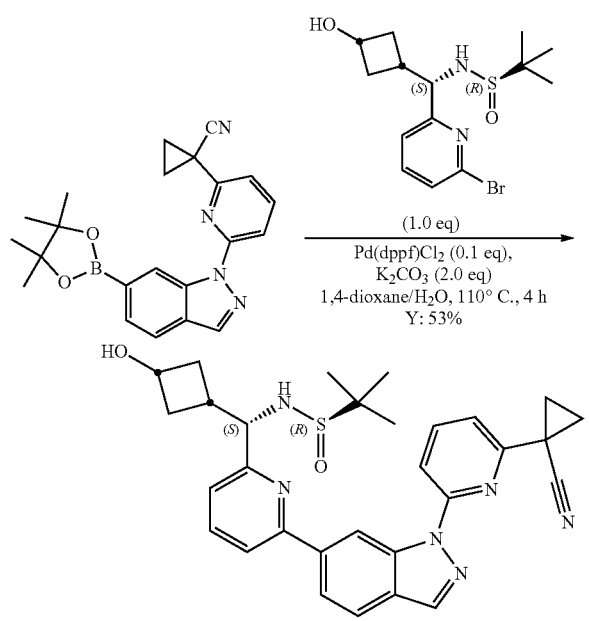

A mixture of 1-(6-(6-(4,4,5,5-tetramethyl-1,3,2-dioxaborolan-2-yl)-1H-indazol-1-yl)pyridin-2-yl)cyclopropanecarbonitrile (175 mg, 0.45 mmol, 1.0 eq), (R)—N—((S)-(6-bromopyridin-2-yl)(cis-3-hydroxycyclobutyl)methyl)-2-methylpropane-2-sulfinamide (Example 10, Step 3, 162 mg, 0.45 mmol, 1.0 eq) and K$_2$CO$_3$ (124 mg, 0.9 mmol, 2.0 eq) in 1,4-dioxane/H$_2$O (20 mL/1 mL) was stirred while purging N$_2$ at rt for 10 min. To this system was added Pd(dppf)Cl$_2$ (41 mg, 0.045 mmol, 0.1 eq) and heated to 110° C. for 4 h. The mixture was diluted with EtOAc (50 mL) and washed with brine (50 mL). The organic was dried (Na$_2$SO$_4$) and concentrated in vacuo. The crude mixture was purified by silica gel chromatography using PE/EA (1/1) as eluent to give (R)—N—((S)-(6-(1-(6-(1-cyanocyclopropyl)pyridin-2-yl)-1H-indazol-6-yl)pyridin-2-yl)((1s,3R)-3-hydroxycyclobutyl)methyl)-2-methylpropane-2-sulfinamide. 130 mg, as a yellow solid, Y: 53%. ESI-MS (M+H)$^+$: 541.2.

Step 4. Synthesis of 1-(6-(6-(6-((S)-amino(cis-3-hydroxycyclobutyl)methyl)pyridin-2-yl)-1H-indazol-1-yl)pyridin-2-yl)cyclopropanecarbonitrile

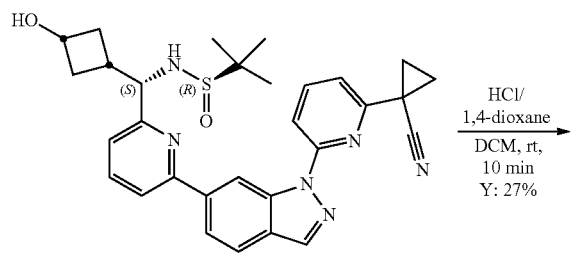

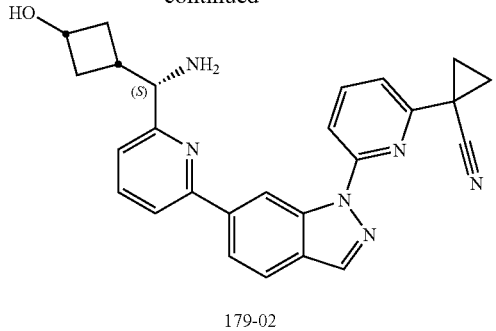

To a solution of (R)—N—((S)-(6-(1-(6-(1-cyanocyclopropyl)pyridin-2-yl)-1H-indazol-6-yl)pyridin-2-yl)((1s,3R)-3-hydroxycyclobutyl)methyl)-2-methylpropane-2-sulfinamide (130 mg, 0.24 mmol, 1.0 eq) in DCM (10 mL) was added 4M HCl in 1,4-dioxane (0.5 mL, excess). The mixture was stirred at rt for 10 min. The solvent was removed in vacuo. The residue was purified by prep-HPLC (CH$_3$CN/0.05% NH$_4$HCO$_3$ in H$_2$O=0%-100%) to give 1-(6-(6-(6-((S)-amino(cis-3-hydroxycyclobutyl)methyl)pyridin-2-yl)-1H-indazol-1-yl)pyridin-2-yl)cyclopropanecarbonitrile. 28 mg as a white solid, Y: 27%. ESI-MS (M+H)$^+$: 437.2. HPLC: 100%. $^1$H NMR (400 MHz, CD$_3$OD) δ: 9.19 (s, 1H), 8.20 (s, 1H), 7.95-7.89 (m, 2H), 7.86-7.80 (m, 3H), 7.75 (t, J=7.6 Hz, 1H), 7.37 (d, J=7.6 Hz, 1H), 7.23 (d, J=7.6 Hz, 1H), 3.98-3.91 (m, 1H), 3.88-3.86 (m, 1H), 2.46-2.43 (m, 1H), 2.10-2.04 (m, 2H), 1.96-1.93 (m, 2H), 1.84-1.83 (m, 2H), 1.79-1.60 (m, 2H).

Examples 21, 22, and 23 3-(amino(6-(1-(6-(hydroxymethyl)pyridin-2-yl)-1H-indazol-6-yl)pyridin-2-yl)methyl)cyclopentanol-A, 3-(amino(6-(1-(6-(hydroxymethyl)pyridin-2-yl)-1H-indazol-6-yl)pyridin-2-yl)methyl)cyclopentanol-B and 3-(amino(6-(1-(6-(hydroxymethyl)pyridin-2-yl)-1H-indazol-6-yl)pyridin-2-yl)methyl)cyclopentanol-C Step 1. Synthesis of methyl 3-hydroxycyclopentanecarboxylate

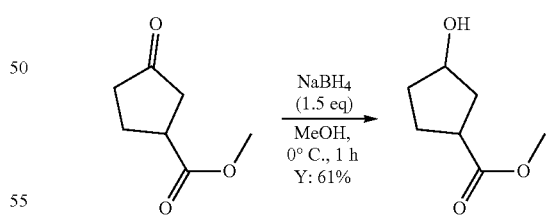

To a solution of methyl 3-oxocyclopentanecarboxylate (5.0 g, 35.2 mmol, TO eq) in MeOH (10 mL) was slowly added NaBH$_4$ (2.0 g, 52.8 mmol, 1.5 eq) at 0° C. Then the mixture was stirred at 0° C. for 1 h. The reaction was quenched with H$_2$O (5 mL). The mixture was extracted with DCM (30 mL×3). The combined organics were dried over Na$_2$SO$_4$, filtrated and concentrated. The residue was purified by silica gel chromatography (PE/EA=4/1) to give methyl 3-hydroxycyclopentanecarboxylate (3.1 g, Y: 61%) as a white solid. ESI-MS (M+H)$^+$: 145.1.

Step 2. Synthesis of methyl 3-(tert-butyldimethylsilyloxy)cyclopentanecarboxylate

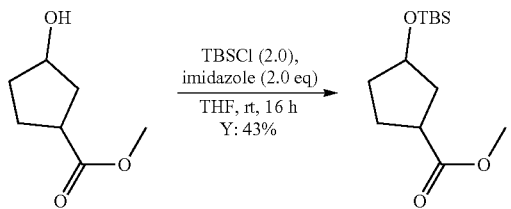

To a solution of methyl 3-hydroxycyclopentanecarboxylate (3.1 g, 21.5 mmol, 1.0 eq) in THF (40 mL), TBSCl (6.5 g, 43 mmol, 2.0 eq) and imidazole (2.9 g, 43 mmol, 2.0 eq) was added. The mixture was stirred at rt for 16 h. The solvent was removed in vacuo. The residue was purified by silica gel chromatography (PE/EA=10/1) to give methyl 3-(tert-butyldimethylsilyloxy)cyclopentanecarboxylate (2.3 g, Y: 43%) as light yellow oil. ESI-MS (M+H)$^+$: 259.1.

Step 3. Synthesis of (3-(tert-butyldimethylsilyloxy)cyclopentyl)methanol

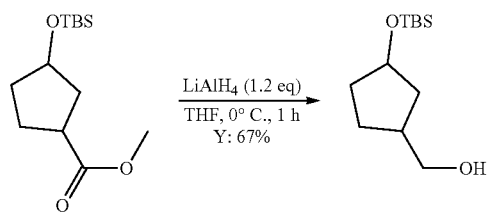 [SMILES: COC(=O)C1CCC(O[Si](C)(C)C(C)(C)C)C1 ; CC(C)(C)[Si](C)(C)OC1CCC(CO)C1]

To a solution of methyl 3-(tert-butyldimethylsilyloxy)cyclopentanecarboxylate (2.0 g, 7.8 mmol, 1.0 eq) in THF (40 mL) was added LiAlH$_4$ (356 mg, 9.3 mmol, 1.2 eq) at 0° C. The mixture was stirred at 0° C. for 1 h. The reaction was quenched with Na$_2$SO$_4$.10H$_2$O and the mixture was filtrated. The filtrate was extracted with EA (40 mL×3). The combined organic fractions were dried over Na$_2$SO$_4$, filtrated and concentrated. The residue was purified by silica gel chromatography (PE/EA=4/1) to give (3-(tert-butyldimethylsilyloxy)cyclopentyl)methanol (1.2 g, Y: 67%) as a white solid. ESI-MS (M+H)$^+$: 231.2.

Step 4. Synthesis of 3-(tert-butyldimethylsilyloxy)cyclopentanecarbaldehyde

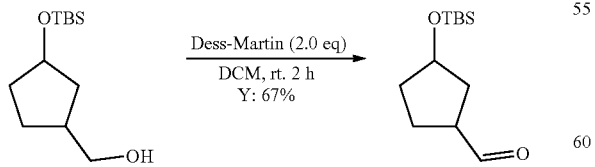

To a solution of (3-(tert-butyldimethylsilyloxy)cyclopentyl)methanol (1.2 g, 5.2 mmol, 1.0 eq) in DCM (30 mL) was added Dess-Martin (4.4 g, 10.4 mmol, 2.0 eq). The mixture was stirred at rt for 2 h. The solvent was removed in vacuo. The residue was purified by silica gel chromatography (PE/EA=10/1) to give 3-(tert-butyldimethylsilyloxy)cyclopentanecarbaldehyde (800 mg, Y: 67%) as a light yellow solid. ESI-MS (M+H)$^+$: 229.2.

Step 5. Synthesis of (1S,R,Z)—N-((3-(tert-butyldimethylsilyloxy)cyclopentyl)methylene)-2-methylpropane-2-sulfinamide

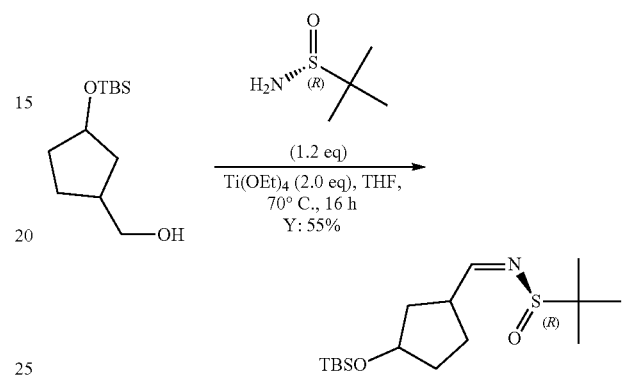

A mixture of 3-(tert-butyldimethylsilyloxy)cyclopentanecarbaldehyde (800 mg, 3.5 mmol, 1.0 eq), (R)-2-methylpropane-2-sulfinamide (508 mg, 4.2 mmol, 1.2 eq) and Ti(OEt)$_4$ (1.6 g, 7.0 mmol, 2.0 eq) in THF (50 mL) was stirred while purging N$_2$ at 70° C. for 16 h. The mixture was diluted with H$_2$O (50 mL) and extracted with EA (50 mL×3). The organic phases were washed with H$_2$O (60 mL) and brine (60 mL) and dried over Na$_2$SO$_4$. After concentration, the residue was purified by silica gel chromatography (PE/EA=8/1) to give (1S,R,Z)—N-((3-(tert-butyldimethylsilyloxy)cyclopentyl)methylene)-2-methylpropane-2-sulfinamide (640 mg, Y: 55%) as yellow oil. ESI-MS (M+H)$^+$: 332.2.

Step 6. Synthesis of (2R)—N-((6-bromopyridin-2-yl)(3-(tert-butyldimethylsilyloxy)cyclopentyl)methyl)-2-methylpropane-2-sulfinamide

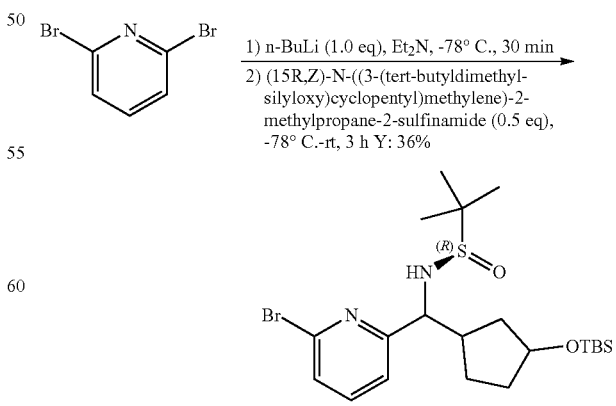

To a solution of 2,6-dibromopyridine (920 mg, 3.9 mmol, TO eq) in Et₂O (60 mL) was added n-BuLi (2.4 M in hexane, 1.6 mL, 3.9 mmol, TO eq) at −78° C. After stirring at −78° C. for min, (1SR,Z)—N-((3-(tert-butyldimethylsilyloxy)cyclopentyl)methylene)-2-methylpropane-2-sulfinamide (640 mg, 1.95 mmol, 0.5 eq) was added and the reaction was stirred for further 3 h at −78° C. The reaction was quenched with H₂O (40 mL) and the mixture was extracted with EA (50 mL×3). The combined organic fractions were dried over Na₂SO₄, filtrated and concentrated. The residue was purified by silica gel chromatography (PE/EA=1/1) to give (2R)—N-((6-bromopyridin-2-yl)(3-(tert-butyldimethylsilyloxy)cyclopentyl)methyl)-2-methylpropane-2-sulfinamide (340 mg, Y: 36%) as a yellow solid. ESI-MS (M+H)⁺: 489.2.

Step 7. Synthesis of (32R)—N-((3-(tert-butyldimethylsilyloxy)cyclopentyl)(6-(1-(6-((tert-butyldimethylsilyloxy)methyl)pyridin-2-yl)-1H-indazol-6-yl)pyridin-2-yl)methyl)-2-methylpropane-2-sulfinamide

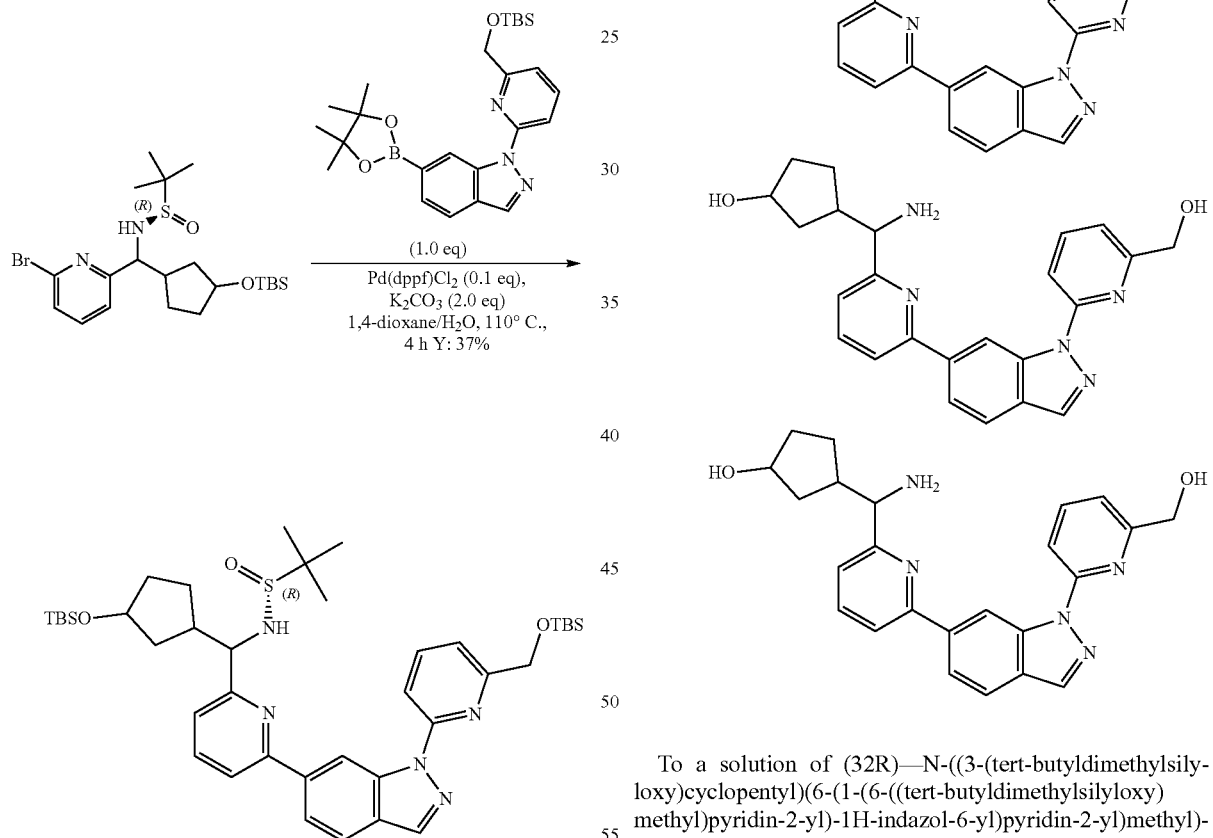

The preparation of (32R)—N-((3-(tert-butyldimethylsilyloxy)cyclopentyl)(6-(1-(6-((tert-butyldimethylsilyloxy)methyl)pyridin-2-yl)-1H-indazol-6-yl)pyridin-2-yl)methyl)-2-methylpropane-2-sulfinamide was similar to that of (R)—N—((S)-(6-(1-(6-(1-cyanocyclopropyl)pyridin-2-yl)-1H-indazol-6-yl)pyridin-2-yl)((1s,3R)-3-hydroxycyclobutyl)methyl)-2-methylpropane-2-sulfinamide (Example 20, Step 3) to give 190 mg as a yellow solid, Y: 37%. ESI-MS (M+H)⁺: 748.4.

Step 8. Synthesis of 3-(amino(6-(1-(6-(hydroxymethyl)pyridin-2-yl)-1H-indazol-6-yl)pyridin-2-yl)methyl)cyclopentanol-A, 3-(amino(6-(1-(6-(hydroxymethyl)pyridin-2-yl)-1H-indazol-6-yl)pyridin-2-yl)methyl)cyclopentanol-B and 3-(amino(6-(1-(6-(hydroxymethyl)pyridin-2-yl)-1H-indazol-6-yl)pyridin-2-yl)methyl)cyclopentanol-C

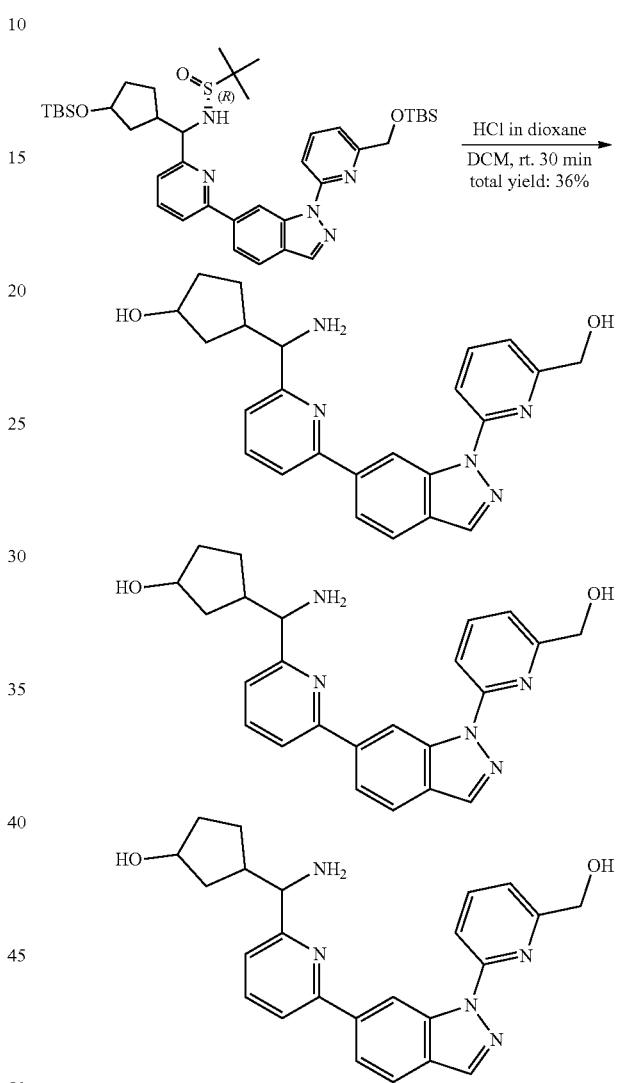

To a solution of (32R)—N-((3-(tert-butyldimethylsilyloxy)cyclopentyl)(6-(1-(6-((tert-butyldimethylsilyloxy)methyl)pyridin-2-yl)-1H-indazol-6-yl)pyridin-2-yl)methyl)-2-methylpropane-2-sulfinamide (190 mg, 0.25 mmol, 1.0 eq) in DCM (10 mL) was added HCl in dioxane (1 mL, excess). The mixture was stirred at rt. for 30 min. The mixture was adjusted to pH=7 with NaOH (aq). The solvent was removed in vacuo. The residue was purified by prep-HPLC (CH₃CN/0.05% NH₄OH in H₂O=0%-100%) to give 3-(amino(6-(1-(6-(hydroxymethyl)pyridin-2-yl)-1H-indazol-6-yl)pyridin-2-yl)methyl)cyclopentanol-A, 3-(amino(6-(1-(6-(hydroxymethyl)pyridin-2-yl)-1H-indazol-6-yl)pyridin-2-yl)methyl)cyclopentanol-B and 3-(amino(6-(1-(6-(hydroxymethyl)pyridin-2-yl)-1H-indazol-6-yl)pyridin-2-yl)methyl)cyclopentanol-C.

3-(amino(6-(1-(6-(hydroxymethyl)pyridin-2-yl)-1H-indazol-6-yl)pyridin-2-yl)methyl)cyclopentanol-A: 17 mg, Y: 16%, as a white solid. ESI-MS (M+H)+: 416.2. HPLC: 100%.

$^1$H NMR (400 MHz, CD$_3$OD) δ: 9.69 (s, 1H), 8.32 (s, 1H), 8.05 (dd, J=8.4, 1.2 Hz, 1H), 8.00-7.89 (m, 5H), 7.41-7.36 (m, 2H), 4.89 (s, 2H), 4.73-4.34 (m, 1H), 3.96 (d, J=8.4 Hz, 1H), 2.81-2.74 (m, 1H), 2.01-1.92 (m, 2H), 1.78-1.42 (m, 4H).

3-(amino(6-(1-(6-(hydroxymethyl)pyridin-2-yl)-1H-indazol-6-yl)pyridin-2-yl)methyl)cyclopentanol-B: 15 mg, Y: 14%, as colorless oil. ESI-MS (M+H)+: 416.2. HPLC: 100%.

$^1$H NMR (400 MHz, CD$_3$OD) δ: 9.68 (s, 1H), 8.32 (s, 1H), 8.04 (d, J=8.4 Hz, 1H), 8.00-7.88 (m, 5H), 7.42-7.36 (m, 2H), 4.89 (s, 2H), 4.31-4.21 (m, 1H), 4.04-4.01 (m, 1H), 2.58-2.52 (m, 1H), 2.25-2.16 (m, 1H), 1.91-1.42 (m, 5H).

3-(amino(6-(1-(6-(hydroxymethyl)pyridin-2-yl)-1H-indazol-6-yl)pyridin-2-yl)methyl)cyclopentanol-C: 6.9 mg, Y: 6%, as a white solid. ESI-MS (M+H)+: 416.2. HPLC: 100%.

$^1$H NMR (400 MHz, CD$_3$OD) δ: 9.68 (s, 1H), 8.32 (s, 1H), 8.04 (dd, J=8.4, 1.2 Hz, 1H), 8.00-7.88 (m, 5H), 7.42-7.35 (m, 2H), 4.89 (s, 2H), 4.29-4.25 (m, 1H), 3.87 (d, J=8.4 Hz, 1H), 2.77-2.70 (m, 1H), 2.17-1.98 (m, 2H), 1.68-1.42 (m, 4H).

Example 24 (1R,3s)-3-((S)-amino(6-(4-(2,2-difluoroethoxy)-1-(6-(hydroxymethyl)pyridin-2-yl)-1H-indazol-6-yl)pyridin-2-yl)methyl)cyclobutanol Step 1. Synthesis of 4-bromo-2,6-difluorobenzaldehyde

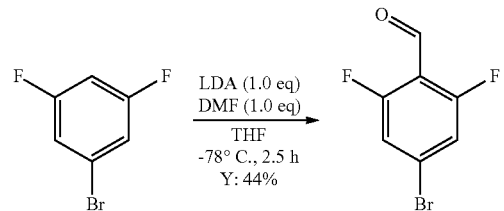 [SMILES: Fc1cc(F)cc(Br)c1 ; O=Cc1c(F)cc(Br)cc1F]

To a solution of 1-bromo-3,5-difluorobenzene (Cas No. 461-96-1, 210 g, 1.09 mol, 1.0 eq) in anhydrous THF (1000 mL), LDA/THF (545 mL, 1.09 mol, TO eq, 2 M) was added slowly under nitrogen atmosphere at −78° C. The reaction solution was stirred for 2 h at −78° C., and then anhydrous DMF (79.6 g, 1.09 mol, TO eq) was added dropwise. The reaction was stirred for 15 min at −78° C. and then a solution of AcOH in ethyl acetate (1/1, 300 mL) was added to adjusted pH=4-5 at −78° C. The reaction mixture was stirred at rt for 15 min, concentrated under reduced pressure, diluted with ethyl acetate (1000 mL) and washed with brine (600 mL×2). The organic layer was dried over anhydrous sodium sulfate, concentrated under reduced pressure and recrystallized from n-hexane to give the title compound (106 g, yield: 44%) as a light yellow solid. $^1$H NMR (400 MHz, CDCl$_3$) δ: 10.29 (s, 1H), 7.23 (s, 1H), 7.21 (s, 1H); ESI-MS (M+H)+: 220.9, 222.9.

Step 2. Synthesis of 4-bromo-2-fluoro-6-methoxybenzaldehyde

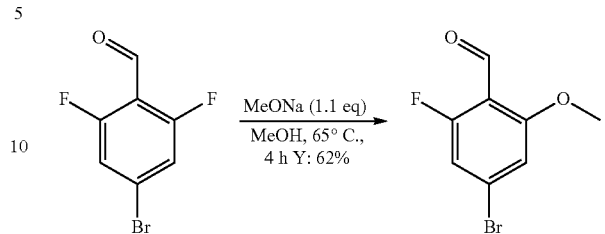

To a solution of 4-bromo-2,6-difluorobenzaldehyde (106 g, 482 mmol, 1.0 eq) in methanol (150 mL), MeONa (26.0 g, 482 mmol, 1.0 eq) was added at rt. The reaction mixture was stirred for 2 h at 60° C. and concentrated under reduced pressure. The residue was purified by silica gel column (PE/EA=10/1) to give 4-bromo-2-fluoro-6-methoxybenzaldehyde (69 g, yield: 62%) as a light yellow solid. $^1$H NMR (400 MHz, CDCl$_3$) δ: 10.36 (s, 1H), 6.97-6.94 (m, 2H), 3.95 (s, 3H); ESI-MS (M+H)+: 232.9, 234.9

Step 3. Synthesis of 6-bromo-4-methoxy-1H-indazole

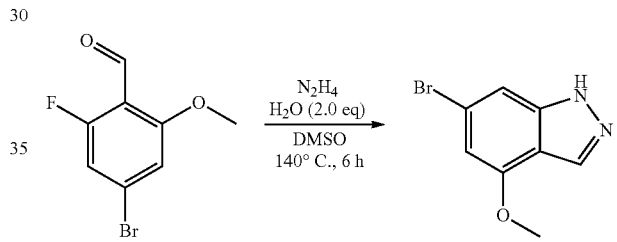

To a stirred solution of 4-bromo-2-fluoro-6-methoxybenzaldehyde (16.5 g, 70.8 mmol) in DMSO (100 mL) was added hydrazine monohydrate (7.1 g, 141 mmol, 2.0 eq). The reaction mixture was stirred at 140° C. for 6 h. After cooled to rt, the reaction solution was diluted with water (100 mL). The precipitate was collected by filtration and washed with water (10 mL×2) to give 6-bromo-4-methoxy-1H-indazole (15.8 g, Y: 98%) as a light yellow solid. $^1$H NMR (400 MHz, CDCl$_3$) δ: 8.10 (s, 1H), 7.27 (s, 1H), 6.61 (d, J=1.2 Hz, 1H), 3.96 (s, 3H); ESI-MS (M+H)+: 229.0.

Step 4. Synthesis of (6-(6-bromo-4-methoxy-1H-indazol-1-yl)pyridin-2-yl)methanol

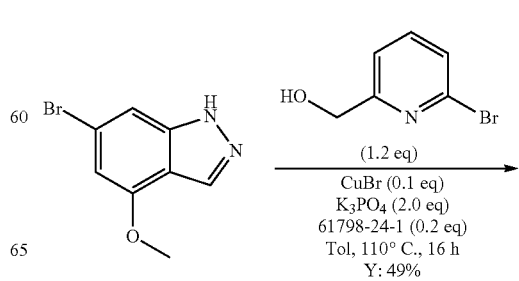

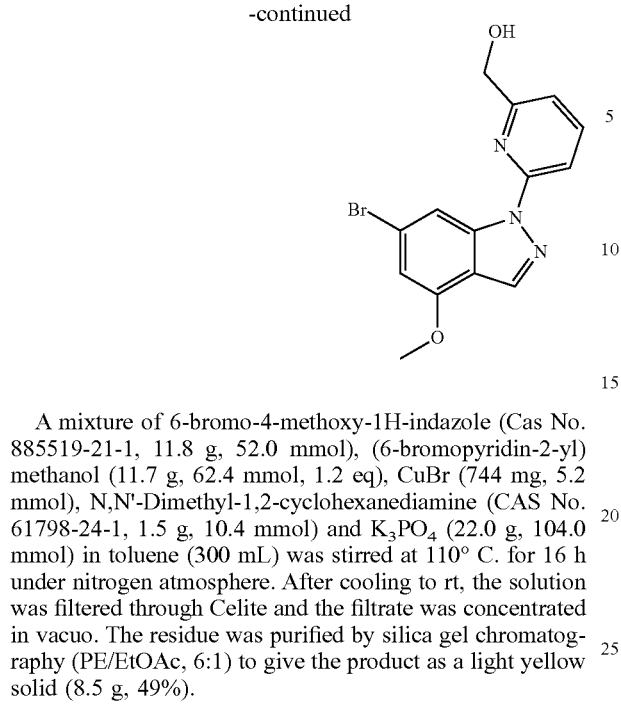

A mixture of 6-bromo-4-methoxy-1H-indazole (Cas No. 885519-21-1, 11.8 g, 52.0 mmol), (6-bromopyridin-2-yl)methanol (11.7 g, 62.4 mmol, 1.2 eq), CuBr (744 mg, 5.2 mmol), N,N'-Dimethyl-1,2-cyclohexanediamine (CAS No. 61798-24-1, 1.5 g, 10.4 mmol) and K₃PO₄ (22.0 g, 104.0 mmol) in toluene (300 mL) was stirred at 110° C. for 16 h under nitrogen atmosphere. After cooling to rt, the solution was filtered through Celite and the filtrate was concentrated in vacuo. The residue was purified by silica gel chromatography (PE/EtOAc, 6:1) to give the product as a light yellow solid (8.5 g, 49%).

ES (+) MS m/e=336/338 (M+1)

Step 5. Synthesis of 6-bromo-1-(6-(hydroxymethyl)pyridin-2-yl)-1H-indazol-4-ol

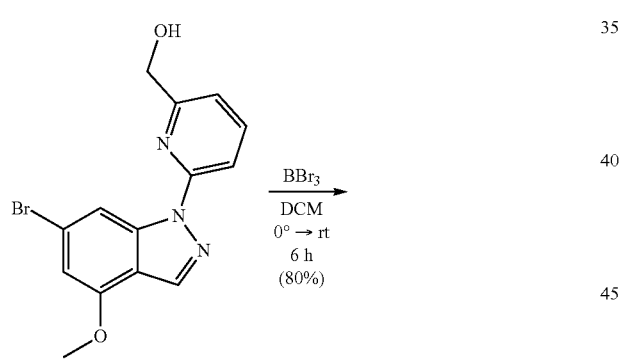

To a suspension of (6-(6-bromo-4-methoxy-1H-indazol-1-yl)pyridin-2-yl)methanol (8.0 g, 24.0 mmol) in DCM (100 mL) was added 3 M BBr₃ in DCM (24 mL, 72.0 mmol) slowly at 0° C. The reaction mixture was stirred for 6 h at rt. The reaction was quenched with MeOH (50 mL) and the product was collected by filtration and washed with MeOH (5 mL×2) to give the title compound (6.2 g, 80%) as a yellow solid. ES (+) MS m/e=321/323 (M+1)

Step 6. Synthesis of 6-bromo-4-((tert-butyldimethylsilyl)oxy)-1-(6-(((tert-butyldimethylsilyl)oxy)methyl)pyridin-2-yl)-1H-indazole

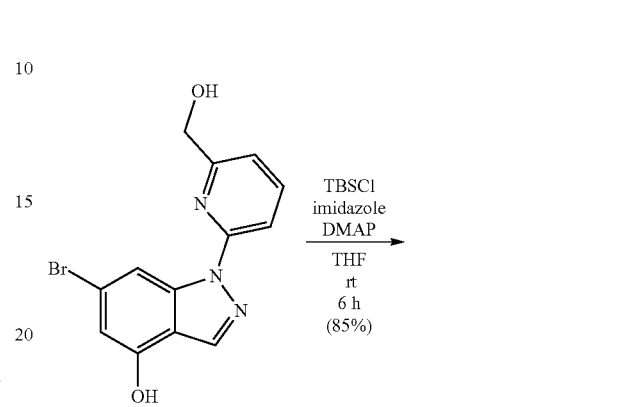

To a solution of 6-bromo-1-(6-(hydroxymethyl)pyridin-2-yl)-1H-indazol-4-ol (6.0 g, 18.75 mmol) in THF (150 mL) were added TBSCl (14.1 g, 93.75 mmol), 1H-imidazole (6.4 g, 93.75 mmol) and DMAP (230 mg, 1.88 mmol). The mixture was stirred at rt for 6 h, diluted with H₂O (200 mL) and extracted with EtOAc (100 mL×3). The combined organic layers were washed with brine (200 mL×2), dried over anhydrous Na₂SO₄, concentrated under reduced pressure to give the product (8.7 g, 85%) as a yellow solid. ES (+) MS m/e=548/550 (M+1)

Step 7. Synthesis of 6-bromo-1-(6-(((tert-butyldimethylsilyl)oxy)methyl)pyridin-2-yl)-1H-indazol-4-ol

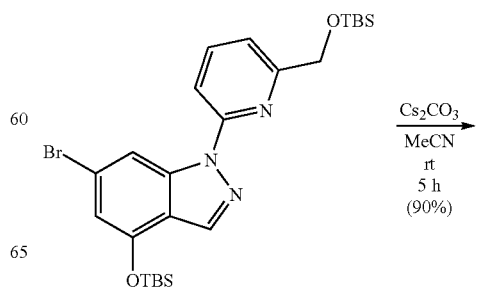

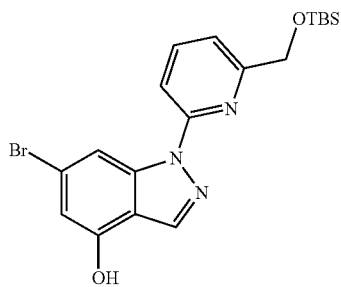

To a solution of 6-bromo-4-((tert-butyldimethylsilyl) oxy)-1-(6-(((tert-butyldimethylsilyl)oxy)methyl)pyridin-2-yl)-1H-indazole (8.0 g, 14.6 mmol) in MeCN (200 mL) were added Cs$_2$CO$_3$ (4.8 g, 14.6 mmol). The mixture was stirred at rt for 5 h, filtered through Celite before concentrating the filtrate in vacuo. The residue was purified by flash chromatography (silica gel, PE/EtOAc, 4:1) to give 6-bromo-1-(6-(((tert-butyldimethylsilyl)oxy)methyl)pyridin-2-yl)-1H-indazol-4-ol (5.7 g, 90%) as a light yellow solid. $^1$H NMR (400 MHz, d$_6$-DMSO) δ 8.48 (s, 1H), 8.21 (s, 1H), 7.84-7.82 (m, 2H), 7.39-7.36 (m, 1H), 6.70 (d, J=1.2 Hz, 1H), 4.92 (s, 2H), 1.00 (s, 9H), 0.08 (s, 6H). ES (+) MS m/e=434/436 (M+1)

Step 8. Synthesis of 6-bromo-1-(6-((tert-butyldimethylsilyloxy)methyl)pyridin-2-yl)-4-(2,2-difluoroethoxy)-1H-indazole

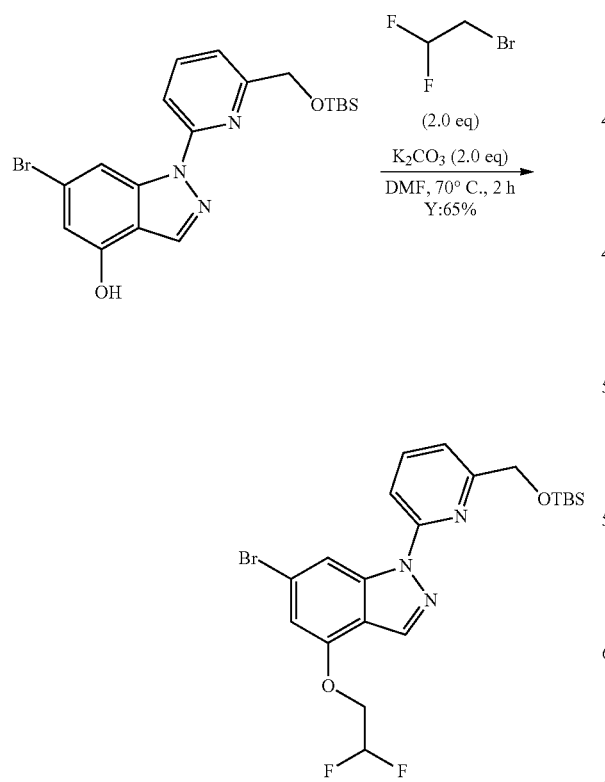

To a solution of 6-bromo-1-(6-((tert-butyldimethylsilyloxy)methyl)pyridin-2-yl)-1H-indazol-4-ol (500 mg, 1.15 mmol, 1.0 eq) in DMF (3 mL) was added 2-bromo-1,1-difluoroethane (331 mg, 2.30 mmol, 2.0 eq) and K$_2$CO$_3$ (317 mg, 2.30 mmol, 2.0 eq). The mixture was stirred at 70° C. for 2 h in a sealed tube. After cooling down to rt, the mixture was diluted with EA (20 mL) and washed with H$_2$O (20 mL×2). The organic was dried (Na$_2$SO$_4$) and concentrated in vacuo. The crude mixture was purified by silica gel chromatography using PE/EA (5/1) as eluent to give 6-bromo-1-(6-((tert-butyldimethylsilyloxy)methyl)pyridin-2-yl)-4-(2,2-difluoroethoxy)-1H-indazole as a yellow solid. 373 mg Y: 65%. ESI-MS (M+H)$^+$: 498.1.

Step 9. Synthesis of 1-(6-((tert-butyldimethylsilyloxy)methyl)pyridin-2-yl)-4-(2,2-difluoroethoxy)-6-(4,4,5,5-tetramethyl-1,3,2-dioxaborolan-2-yl)-1H-indazole

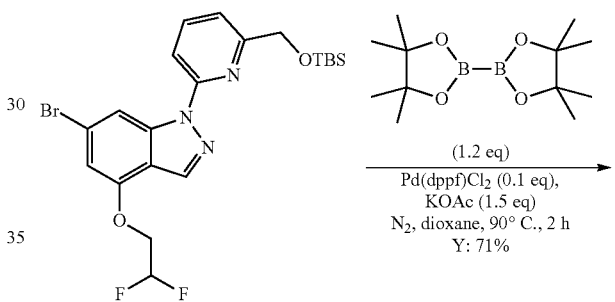

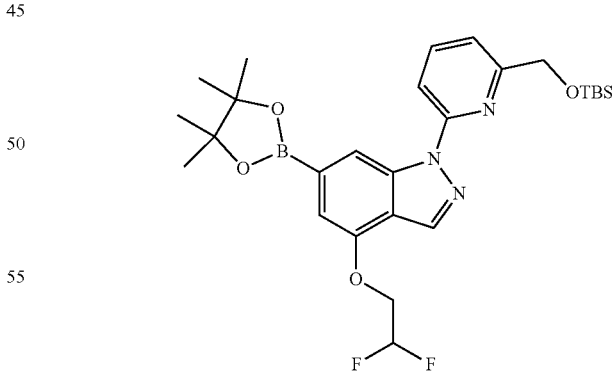

The preparation of 1-(6-((tert-butyldimethylsilyloxy)methyl)pyridin-2-yl)-4-(2,2-difluoroethoxy)-6-(4,4,5,5-tetramethyl-1,3,2-dioxaborolan-2-yl)-1H-indazole was similar to that of 1-(6-(6-(4,4,5,5-tetramethyl-1,3,2-dioxaborolan-2-yl)-1H-indazol-1-yl)pyridin-2-yl) cyclopropanecarbonitrile (Example 20, Step 2) to give 280 mg as yellow oil, Y: 71%. ESI-MS (M+H)$^+$: 546.2.

Step 10. Synthesis of (R)—N—((S)-(3-(tert-butyldimethylsilyloxy)cyclobutyl)(6-(1-(6-((tert-butyldimethylsilyloxy)methyl)pyridin-2-yl)-4-(2,2-difluoroethoxy)-1H-indazol-6-yl)pyridin-2-yl)methyl)-2-methylpropane-2-sulfinamide

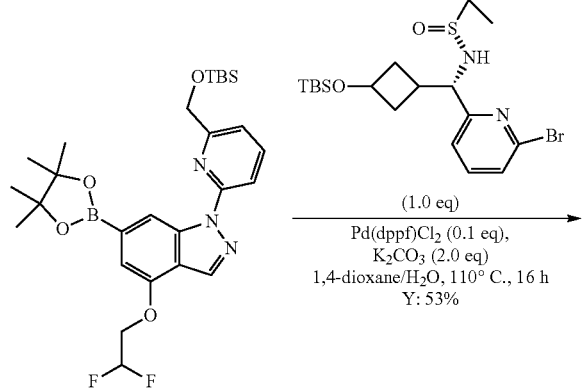

The preparation of (R)—N—((S)-(3-(tert-butyldimethylsilyloxy)cyclobutyl)(6-(1-(6-((tert-butyldimethylsilyloxy)methyl)pyridin-2-yl)-4-(2,2-difluoroethoxy)-1H-indazol-6-yl)pyridin-2-yl)methyl)-2-methylpropane-2-sulfinamide was similar to that of (R)—N—((S)-(6-(1-(6-(1-cyanocyclopropyl)pyridin-2-yl)-1H-indazol-6-yl)pyridin-2-yl)((1s,3R)-3-hydroxycyclobutyl)methyl)-2-methylpropane-2-sulfinamide (Example 20, Step 3) to give 140 mg as a yellow solid, Y: 53%. ESI-MS (M+H)⁺: 814.3.

Step 11. Synthesis of (1R,3s)-3-((S)-amino(6-(4-(2,2-difluoroethoxy)-1-(6-(hydroxymethyl)pyridin-2-yl)-1H-indazol-6-yl)pyridin-2-yl)methyl)cyclobutanol

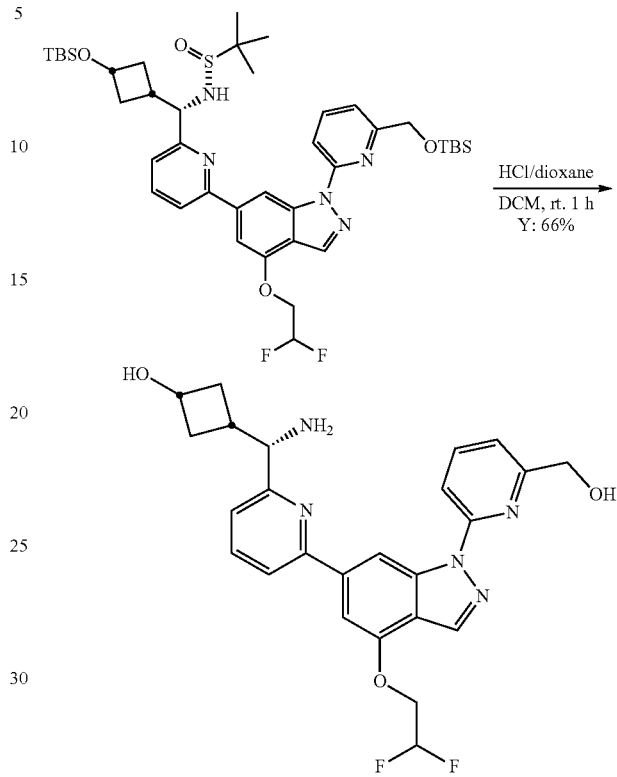

The preparation of (1R,3s)-3-((S)-amino(6-(4-(2,2-difluoroethoxy)-1-(6-(hydroxymethyl)pyridin-2-yl)-1H-indazol-6-yl)pyridin-2-yl)methyl)cyclobutanol was similar to that of 1-(6-(6-(6-((S)-amino(cis-3-hydroxycyclobutyl)methyl)pyridin-2-yl)-1H-indazol-1-yl)pyridin-2-yl)cyclopropanecarbonitrile (Example 20, Step 4) to give 55 mg as a white solid, Y: 66%. ESI-MS (M+H)⁺: 482.2. HPLC: 100%. ¹H NMR (400 MHz, CD₃OD) δ: 9.19 (s, 1H), 8.29 (s, 1H), 7.97-7.84 (m, 4H), 7.51 (s, 1H), 7.40 (d, J=7.2 Hz, 1H), 7.33-7.31 (m, 1H), 6.36 (tt, J=14.8, 3.6 Hz, 1H), 4.86 (s, 2H), 4.62-4.54 (m, 2H), 4.12-4.05 (m, 1H), 3.93 (d, J=8.4 Hz, 1H), 2.61-2.53 (m, 1H), 2.24-2.12 (m, 2H), 1.88-1.75 (m, 2H).

Example 25 (1R,3s)-3-((1S)-amino(6-(1-(4-(1-hydroxyethyl)pyrimidin-2-yl)-1H-indazol-6-yl)pyridin-2-yl)methyl)cyclobutanol

Step 1. Synthesis of 2-(6-bromo-1H-indazol-1-yl)-N-methoxy-N-methylpyrimidine-4-carboxamide

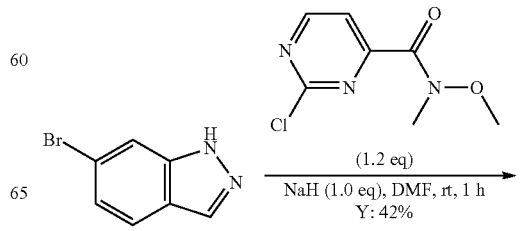

Step 3. Synthesis of 1-(2-(6-bromo-1H-indazol-1-yl)pyrimidin-4-yl)ethanol

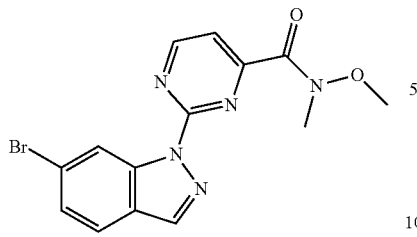

To a solution of 6-bromo-1H-indazole (3.0 g, 15.3 mmol, 1.0 eq) in DMF (10 mL) was added NaH (60% in oil, 612 mg, 15.3 mmol, 1.0 eq) at rt. The mixture was stirred at rt for 10 min. Then 2-chloro-N-methoxy-N-methylpyrimidine-4-carboxamide (3.7 g, 18.4 mmol, 1.2 eq) was added into the mixture. The mixture was stirred at rt for 1 h. The mixture was poured into water (60 mL). After filtration, the yellow solid was dried in vacuo. 2.3 g, Y: 42%. ESI-MS (M+H)+: 362.1.

Step 2. Synthesis of 1-(2-(6-bromo-1H-indazol-1-yl)pyrimidin-4-yl)ethanone

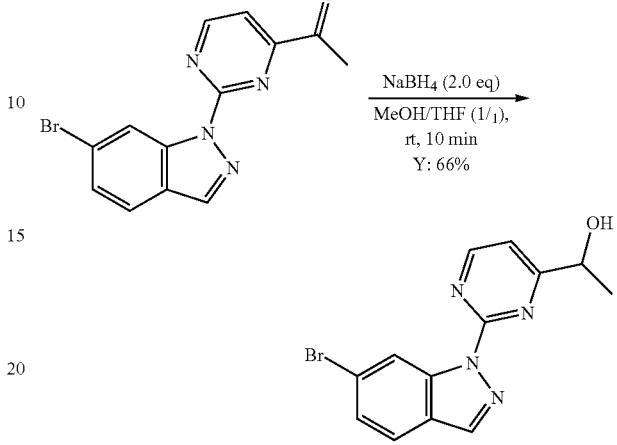

To a solution of 1-(2-(6-bromo-1H-indazol-1-yl)pyrimidin-4-yl)ethanone (1.37 g, 4.33 mmol, 1.0 eq) in MeOH/THF (10 mL/10 mL) was added NaBH₄ (329 mg, 8.66 mmol, 2.0 eq) at rt. The mixture was stirred at rt for 10 min. After concentration, the residue was dissolved in MeOH (5 mL) and diluted with water (30 mL). After filtration, the white solid was dried in vacuo. 909 mg, Y: 66%. ESI-MS (M+H)+: 319.1.

Step 4. Synthesis of 6-bromo-1-(4-(1-(tert-butyldimethylsilyloxy)ethyl)pyrimidin-2-yl)-1H-indazole

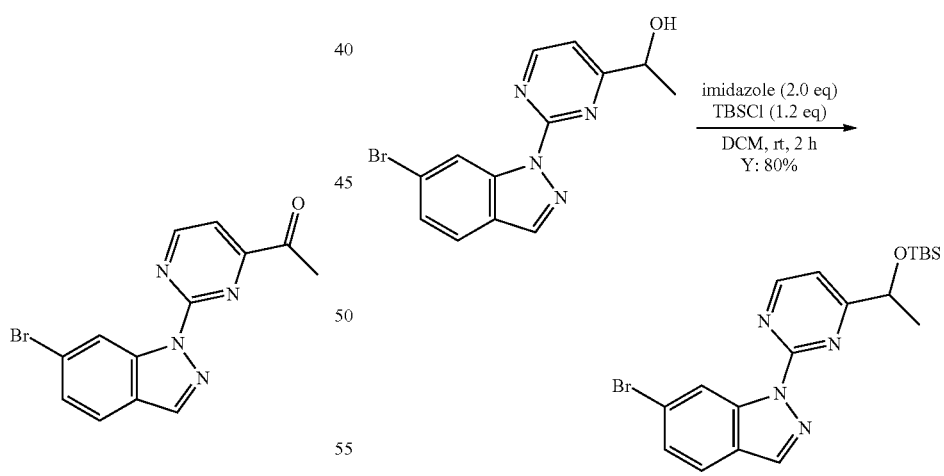

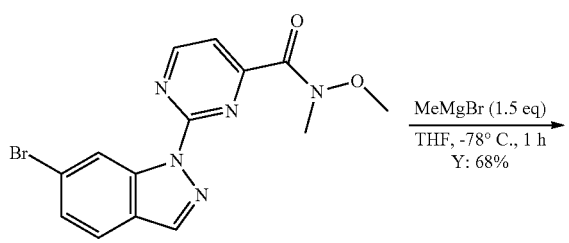

To a solution of 2-(6-bromo-1H-indazol-1-yl)-N-methoxy-N-methylpyrimidine-4-carboxamide (2.3 g, 6.37 mmol, 1.0 eq) in THF (20 mL) was added MeMgBr (2 M, 4.8 mL, 9.60 mmol, 1.5 eq) at −78° C. The mixture was stirred at −78° C. for 1 h. The mixture was quenched with water and extracted with DCM (3×80 mL). The combined organic phase was washed with brine and dried over Na₂SO₄. After filtration and concentration, the residue was recrystallized from EA. 1-(2-(6-bromo-1H-indazol-1-yl)pyrimidin-4-yl)ethanone. 1.37 g, as a yellow solid, Y: 68%, ESI-MS (M+H)+: 317.1.

To a solution of 1-(2-(6-bromo-1H-indazol-1-yl)pyrimidin-4-yl)ethanol (909 mg, 2.86 mmol, 1.0 eq) in DCM (20 mL) was added imidazole (389 mg, 5.72 mmol, 2.0 eq) and TBSCl (515 mg, 3.43 mmol, 1.2 eq) at rt. The mixture was stirred at rt for 2 h. The mixture was quenched with water and extracted with DCM (3×80 mL). The combined organic phase was washed with brine and dried over Na₂SO₄. After filtration and concentration, the residue was purified by silica gel chromatography using PE/EA (4/1) as eluent to give 6-bromo-1-(4-(1-(tert-butyldimethylsilyloxy)ethyl)pyrimidin-2-yl)-1H-indazole as a yellow solid. 988 mg, Y: 80%, ESI-MS (M+H)+: 433.2.

Step 5. Synthesis of 1-(4-(1-(tert-butyldimethylsilyloxy)ethyl)pyrimidin-2-yl)-6-(4,4,5,5-tetramethyl-1,3,2-dioxaborolan-2-yl)-1H-indazole

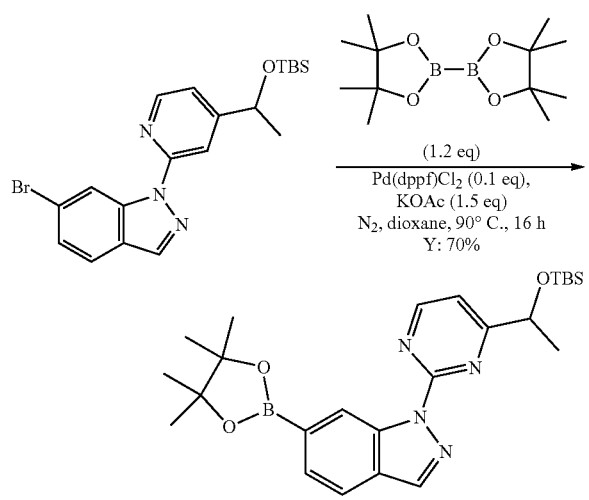

A mixture of 6-bromo-1-(4-(1-(tert-butyldimethylsilyloxy)ethyl)pyrimidin-2-yl)-1H-indazole (180 mg, 0.41 mmol, 1.0 eq), 4,4,4',4',5,5,5',5'-octamethyl-2,2'-bi(1,3,2-dioxaborolane) (130 mg, 0.50 mmol, 1.2 eq) and KOAc (80 mg, 0.82 mmol, 2.0 eq) in 1,4-dioxane (10 mL) was stirred while purging N₂ at rt for 10 min. To this system was added Pd(dppf)Cl₂ (30 mg, 0.04 mmol, 0.1 eq) and heated to 90° C. for 16 h. The mixture was diluted with EA (50 mL) and washed with brine (50 mL). The organic was dried (Na₂SO₄) and concentrated in vacuo to give 1-(4-(1-(tert-butyldimethylsilyloxy)ethyl)pyrimidin-2-yl)-6-(4,4,5,5-tetramethyl-1,3,2-dioxaborolan-2-yl)-1H-indazole. 140 mg, as a yellow solid, Y: 70%. ESI-MS (M+H)+: 481.2.

Step 6. Synthesis of (R)—N—((S)-((1s,3R)-3-(tert-butyldimethylsilyloxy)cyclobutyl)(6-(1-(4-((tert-butyldimethylsilyloxy)methyl)pyrimidin-2-yl)-1H-indazol-6-yl)pyridin-2-yl)methyl)-2-methylpropane-2-sulfinamide

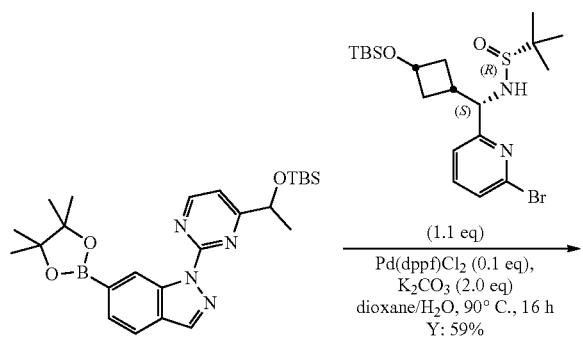

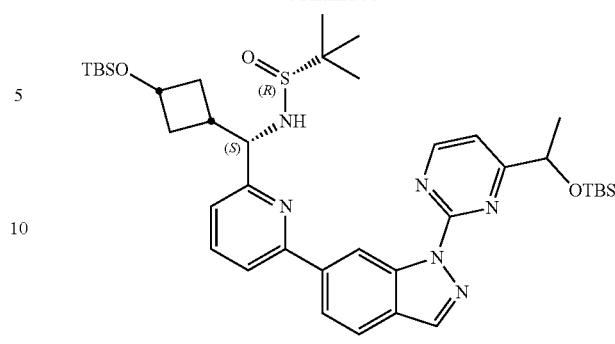

The preparation of (R)—N-((1S)-((1s,3R)-3-(tert-butyldimethylsilyloxy)cyclobutyl)(6-(1-(4-(1-(tert-butyldimethylsilyloxy)ethyl)pyrimidin-2-yl)-1H-indazol-6-yl)pyridin-2-yl)methyl)-2-methylpropane-2-sulfinamide was similar to that of (R)—N—((S)-(6-(1-(6-(1-cyanocyclopropyl)pyridin-2-yl)-1H-indazol-6-yl)pyridin-2-yl)((1s,3R)-3-hydroxycyclobutyl)methyl)-2-methylpropane-2-sulfinamide (Example 20, Step 3) to give 110 mg as yellow oil, Y: 59%. ESI-MS (M+H)+: 749.4.

Step 7. Synthesis of (1R,3s)-3-((1S)-amino(6-(1-(4-(1-hydroxyethyl)pyrimidin-2-yl)-1H-indazol-6-yl)pyridin-2-yl)methyl)cyclobutanol (TFA)

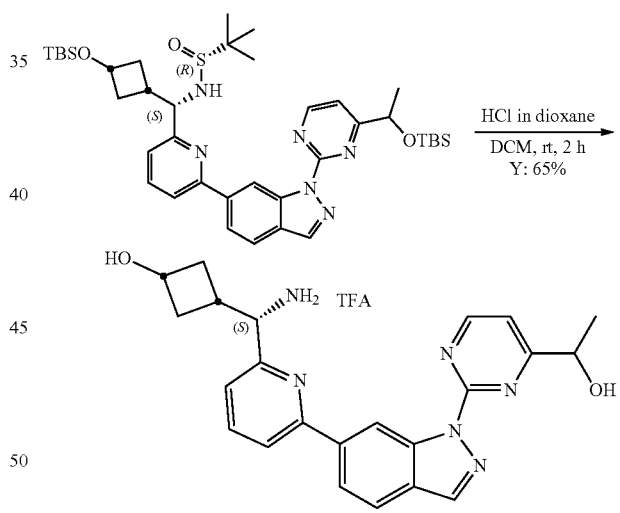

The preparation of (1R,3s)-3-((1S)-amino(6-(1-(4-(1-hydroxyethyl)pyrimidin-2-yl)-1H-indazol-6-yl)pyridin-2-yl)methyl)cyclobutanol (TFA) was similar to that of 1-(6-(6-(6-((S)-amino(cis-3-hydroxycyclobutyl)methyl)pyridin-2-yl)-1H-indazol-1-yl)pyridin-2-yl)cyclopropanecarbonitrile (Example 20, Step 4) to give 15 mg as a yellow solid, Y: 65%. ESI-MS (M+H)+: 417.2. HPLC: 100% ¹H NMR (400 MHz, CD₃OD) δ: 9.67 (s, 0.5H), 9.58 (s, 0.5H), 8.89 (t, J=4.8 Hz, 1H), 9.48 (s, 1H), 8.26-8.22 (m, 1H), 8.11-8.08 (m, 1H), 8.04-8.00 (m, 2H), 7.52-7.49 (m, 1H), 7.44 (d, J=7.6 Hz, 1H), 5.07-5.03 (m, 1H), 4.49-4.47 (m, 1H), 4.16-4.12 (m, 1H), 2.64-2.60 (m, 1H), 2.39-2.36 (m, 2H), 1.97-1.87 (m, 2H), 1.66-1.64 (m, 3H).

Example 26 (S)-(6-(6-(6-(amino(3,3-difluorocyclobutyl)methyl)pyridin-2-yl)-1H-indazol-1-yl)pyridin-2-yl)methanol Step 1. Synthesis of (6-bromopyridin-2-yl)(3,3-difluorocyclobutyl)methanol

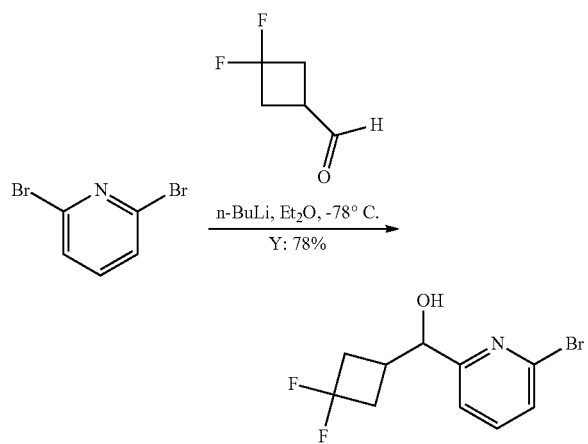

To a suspension of 2,6-dibromopyridine (6.39 g, 27.0 mmol) in Et₂O (200 mL) at −78° C. was added a 2.5 M solution of n-butyllithium in hexanes (9.9 mL, 25 mmol). After 30 min, 3,3-difluorocyclobutanecarbaldehyde (2.7 g, 22 mmol) in Et₂O was added. After 15 min, the reaction was allowed to warm to −10° C. over 30 minutes then quenched by addition of saturated NH₄Cl. The layers were separated and the aqueous layer was extracted once with diethyl ether. The combined ether layers were washed with brine, dried over MgSO₄, filtered, and concentrated. The residue was purified over SiO₂ (80 g, 10-30% EtOAc in heptane) to afford (6-bromopyridin-2-yl)(3,3-difluorocyclobutyl)methanol (4.9 g, 78%). LCMS (ESI+) 278.0 (M+H)⁺. ¹H NMR (400 MHz, CDCl₃) δ 7.53-7.62 (m, 1H), 7.42 (d, J=8.03 Hz, 1H), 7.24 (d, J=7.53 Hz, 1H), 4.71 (d, J=4.77 Hz, 1H), 2.45-2.76 (m, 4H), 2.29-2.45 (m, 1H)

Step 2. Synthesis of (6-bromopyridin-2-yl)(3,3-difluorocyclobutyl)methanone

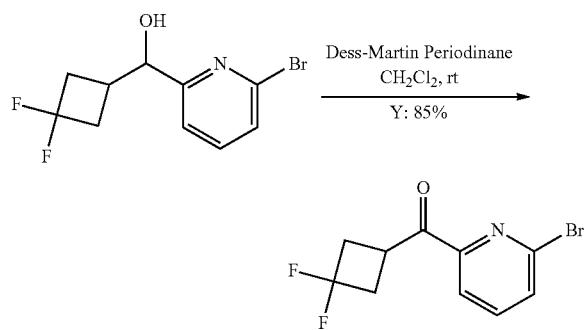

To a solution of (6-bromopyridin-2-yl)(3,3-difluorocyclobutyl)methanol (4.64 g, 16.7 mmol) in CH₂Cl₂ (100 mL) was added Dess-Martin periodinane (8.5 g, 20.0 mmol) as a solid. The reaction was stirred at room temperature for 1.5 h then water (3.0 mL) was added. The reaction was stirred for an hour then 10% sodium thiosulfate/sat NaHCO₃ was added and stirred for 1 h. The organic phase was separated and dried over MgSO₄, filtered, and concentrated. The residue was purified over SiO₂ (40 g, 0-5% EtOAc in heptane) to afford (6-bromopyridin-2-yl)(3,3-difluorocyclobutyl)methanone (3.914 g, 85%). LCMS (ESI+) 276.0 (M+H)⁺. ¹H NMR (400 MHz, CDCl₃) δ 8.04 (dd, J=1.25, 7.28 Hz, 1H), 7.66-7.76 (m, 2H), 4.21 (m, 1H), 4.06-4.16 (m, 1H), 2.81-2.97 (m, 4H)

Step 3. Synthesis of (R)—N-((6-bromopyridin-2-yl)(3,3-difluorocyclobutyl)methylene)-2-methylpropane-2-sulfinamide

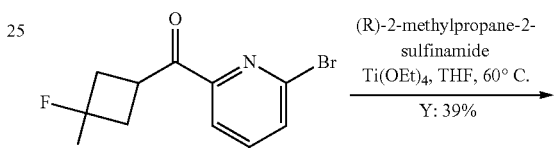

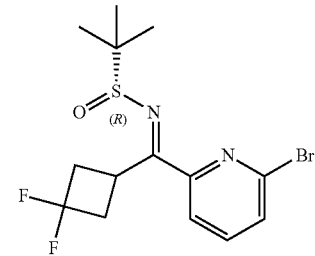

(6-bromopyridin-2-yl)(3,3-difluorocyclobutyl)methanone (3.94 g, 14.27 mmol) in anhydrous THF (50 mL) was treated with (R)-(+)-2-methyl-2-propanesulfinamide (2.27 g, 18.6 mmol) and titanium tetraethyloxide (8.43 mL, 28.5 mmol). The mixture was heated to 60° C. overnight and subsequently cooled to room temperature and quenched with water (5.0 mL) and EtOAc (50 mL). The suspension was filtered through Celite, rinsed with EtOAc and concentrated in vacuo. The residue was purified over SiO₂ (24 g, 30-40% EtOAc in heptane) to afford (A)-N-((6-bromopyridin-2-yl)(3,3-difluorocyclobutyl)methylene)-2-methylpropane-2-sulfinamide (2.10 g, 38.8%). LCMS (ESI+) 379.0 (M+H)⁺. ¹H NMR (400 MHz, CDCl₃) δ 7.60-7.67 (m, 1H), 7.50-7.59 (m, 2H), 3.59-3.68 (m, 1H), 2.74-3.14 (m, 4H), 1.27-1.32 (m, 9H).

Step 4. Synthesis of (R)-A-((S)-(6-bromopyridin-2-yl)(3,3-difluorocyclobutyl)methyl)-2-methylpropane-2-sulfinamide & (R)—N—((R)-(6-bromopyridin-2-yl)(3,3-difluorocyclobutyl)methyl)-2-methylpropane-2-sulfinamide

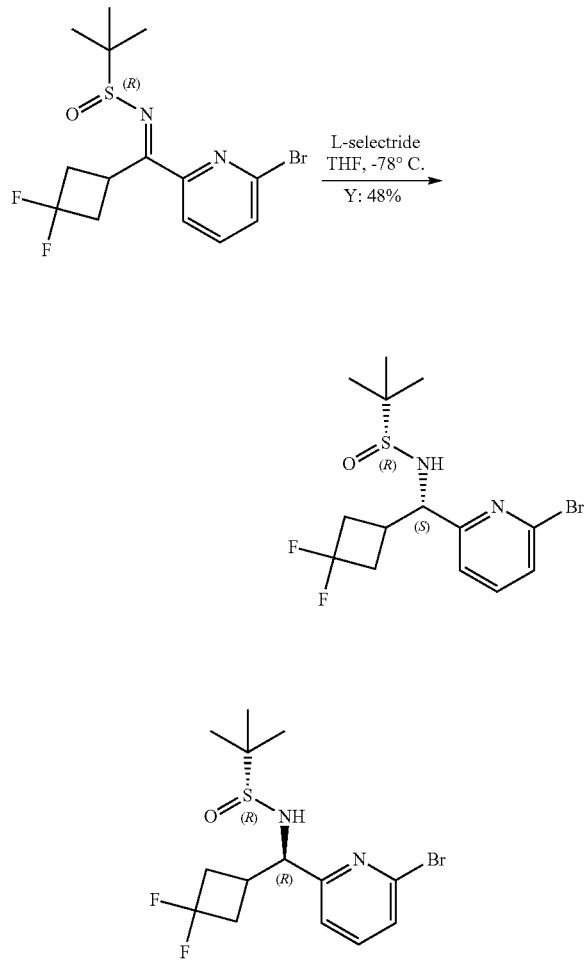

To a solution of (R)—N-((6-bromopyridin-2-yl)(3,3-difluorocyclobutyl)methylene)-2-methylpropane-2-sulfinamide (2.10 g, 5.5 mmol) in anhydrous THF (50 mL) at −78° C. was added a solution of L-Selectride (1.0 M in THF, 11.0 mmol, 11 mL) dropwise over 20 minutes. The reaction was allowed to stir at −78° C. for 1 h. The reaction was quenched by addition of saturated NH₄Cl. The mixture was diluted with EtOAc and the layers were separated. The organic phase was washed with brine, dried over MgSO₄, filtered, and concentrated in vacuo. The residue was purified over SiO₂ (24 g, 0-60% EtOAc in heptane) to afford a mixture of diastereomers (1.025 g; 48%). The diastereomers were separated using reverse phase HPLC (Column: Waters Sunfire C18 OBD 50×100 mm, 5 um. Solvent system: 30% to 60% (B, acetonitrile) over 15 minutes (A, H₂O) (flow rate: 80 mL/min). Modifier: 0.1% formic acid). Peak 1, (R)—N—((S)-(6-bromopyridin-2-yl)(3,3-difluorocyclobutyl)methyl)-2-methylpropane-2-sulfinamide (0.578 g). LCMS (ESI+) 381.0 (M+H)⁺. ¹H NMR (400 MHz, CDCl₃) δ 7.52-7.57 (m, 1H), 7.40-7.43 (m, 1H), 7.22 (d, J=7.53 Hz, 1H), 4.35 (d, J=8.78 Hz, 1H), 2.72-2.83 (m, 2H), 2.59-2.68 (m, 2H), 2.31-2.41 (m, 1H), 1.18 (s, 9H). Peak 2, (R)—N—((R)-(6-bromopyridin-2-yl)(3,3-difluorocyclobutyl)methyl)-2-methylpropane-2-sulfinamide (0.438 g). LCMS (ESI+) 381.0 (M+H)⁺. ¹H NMR (400 MHz, CDCl₃) δ 7.49-7.57 (m, 1H), 7.40 (dd, J=0.75, 8.03 Hz, 1H), 7.25 (dd, J=0.75, 7.53 Hz, 1H), 4.65 (br d, J=8.28 Hz, 1H), 4.28 (t, J=7.53 Hz, 1H), 2.43-2.67 (m, 4H), 2.27-2.42 (m, 1H), 1.28 (s, 9H).

Step 5. Synthesis of (R)—N—((S)-(6-(1-(6-(((tert-butyldimethylsilyl)oxy)methyl)pyridin-2-yl)-1H-indazol-6-yl)pyridin-2-yl)(3,3-difluorocyclobutyl)methyl)-2-methylpropane-2-sulfinamide

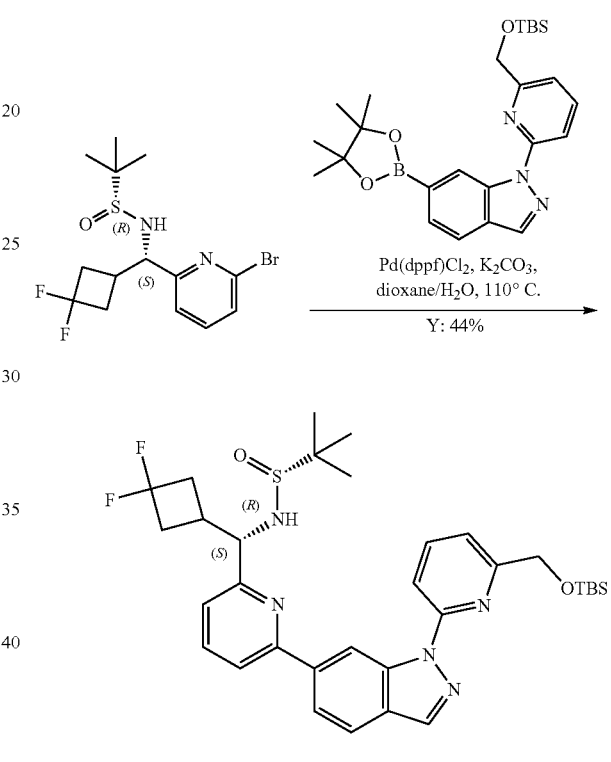

A suspension of 1-(6-(((tert-butyldimethylsilyl)oxy)methyl)pyridin-2-yl)-6-(4,4,5,5-tetramethyl-1,3,2-dioxaborolan-2-yl)-1H-indazole (Example 1, Step 9, 0.110 g, 0.236 mmol), K₂CO₃ (0.0816 g, 0.590 mmol), (R)—N—((S)-(6-bromopyridin-2-yl)(3,3-difluorocyclobutyl)methyl)-2-methylpropane-2-sulfinamide (Example 26, Step 4, 0.075 g, 0.20 mmol), and Pd(dppf)Cl₂ (8.0 mg, 0.010 mmol) in dioxane (0.66 mL) and water (0.22 mL) were purged with nitrogen for 15 minutes then warmed to 110° C. for 2 h. The mixture was cooled to room temperature, adsorbed onto silica and purified over SiO₂ (12 g, 50-100% EtOAc in heptane) to provide (R)—N—((S)-(6-(1-(6-(((tert-butyldimethylsilyl)oxy)methyl)pyridin-2-yl)-1H-indazol-6-yl)pyridin-2-yl)(3,3-difluorocyclobutyl)methyl)-2-methylpropane-2-sulfinamide (0.056 g; 44%). LCMS (ESI+) 640.3 (M+H)⁺. ¹H NMR (400 MHz, CDCl₃) δ 9.34 (s, 1H), 8.24 (s, 1H), 8.02 (dd, J=1.51, 8.53 Hz, 1H), 7.85-7.97 (m, 3H), 7.82 (d, J=4.02 Hz, 2H), 7.42 (d, J=7.28 Hz, 1H), 7.24 (t, J=4.27 Hz, 1H), 4.96 (s, 2H), 4.46-4.56 (m, 1H), 4.37 (br s, 1H), 2.65-2.92 (m, 3H), 2.46-2.58 (m, 2H), 1.18 (s, 9H), 1.00 (s, 9H), 0.17 (s, 6H).

Step 6. Synthesis of (S)-(6-(6-(6-(amino(3,3-difluorocyclobutyl)methyl)pyridin-2-yl)-1H-indazol-1-yl)pyridin-2-yl)methanol

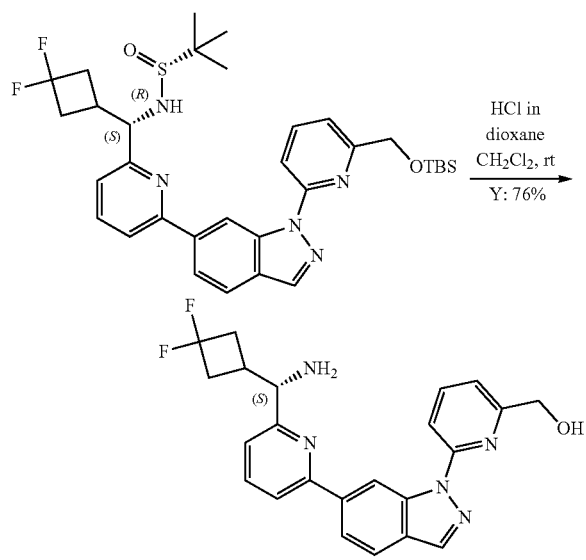

To a solution of (R)-A-((S)-(6-(1-(6-(((tert-butyldimethylsilyl)oxy)methyl)pyridin-2-yl)-1H-indazol-6-yl)pyridin-2-yl)(3,3-difluorocyclobutyl)methyl)-2-methylpropane-2-sulfinamide (0.056 g, 0.088 mmol) in CH$_2$Cl$_2$ (2 mL) was added a solution of hydrogen chloride (4.0 M in dioxane, 0.650 mL, 2.60 mmol). The resulting mixture was stirred at room temperature for 2 h. The mixture was diluted with Et$_2$O and stirred at room temperature for 30 min. The resulting precipitate was filtered to provide (S)-(2-(6-(6-(amino(3,3-difluorocyclobutyl)methyl)pyridin-2-yl)-1H-indazol-1-yl)pyrimidin-4-yl)methanol (0.028 g; 76%). LCMS (ESI+) 422.2 (M+H)$^+$. $^1$H NMR (400 MHz, DMSO-d$_6$) δ 9.59 (m, 1H), 8.55 (br s, 3H), 8.51 (d, J=1.00 Hz, 1H), 8.23 (dd, J=1.51, 8.5 Hz, 1H), 8.07 (m, 4H), 7.90 (dd, J=0.75, 8.03 Hz, 1H), 7.56 (dd, J=0.88, 7.40 Hz, 1H), 7.42 (dd, J=0.88, 7.40 Hz, 1H), 5.65 (m, 1H), 4.79 (s, 2H), 4.64 (m, 1H), 2.74 (m, 4H).

Example 27 (R)-(6-(6-(6-(amino(3,3-difluorocyclobutyl)methyl)pyridin-2-yl)-1H-indazol-1-yl)pyridin-2-yl)methanol

Step 1. Synthesis of (R)—N—((R)-(6-(1-(6-(((tert-butyldimethylsilyl)oxy)methyl)pyridin-2-yl)-17f-indazol-6-yl)pyridin-2-yl)(3,3-difluorocyclobutyl)methyl)-2-methylpropane-2-sulfinamide

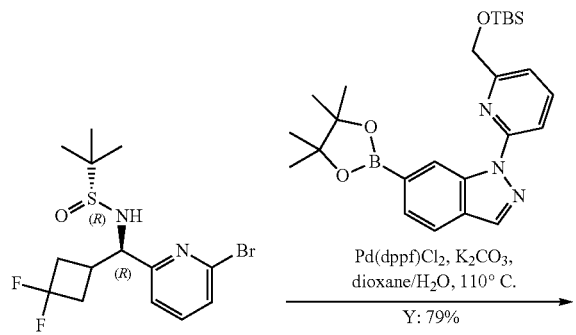

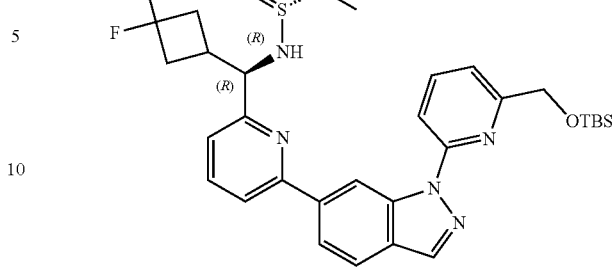

A suspension of 1-(6-(tert-butyldimethylsilyl)oxy)methyl)pyridin-2-yl)-6-(4,4,5,5-tetramethyl-1,3,2-dioxaborolan-2-yl)-1H-indazole (Example 1, Step 9, 0.110 g, 0.236 mmol), K$_2$CO$_3$ (81.6 mg, 0.590 mmol), (R)—N—((R)-(6-bromopyridin-2-yl)(3,3-difluorocyclobutyl)methyl)-2-methylpropane-2-sulfinamide (Example 26, step 4, 0.075 g, 0.20 mmol), Pd(dppf)Cl$_2$ (8.0 mg, 0.010 mmol) in dioxane (0.66 mL) and water (0.22 mL) were purged with nitrogen for 15 minutes then warmed to 70° C. for 2 h. The mixture was cooled to room temperature, adsorbed onto silica and purified over SiO$_2$ (12 g, 50-100% EtOAc:heptane) to provide (R)-A-((R)-(6-(1-(6-(((tert-butyldimethylsilyl)oxy)methyl)pyridin-2-yl)-1H-indazol-6-yl)pyridin-2-yl)(3,3-difluorocyclobutyl)methyl)-2-methylpropane-2-sulfinamide (0.100 g; 79%). LCMS (ESI+) 640.3 (M+H)$^+$. $^1$H NMR (400 MHz, CDCl$_3$) δ 9.27-9.31 (m, 1H), 8.23 (d, J=0.75 Hz, 1H), 7.74-8.04 (m, 6H), 7.42 (dd, J=1.13, 7.15 Hz, 1H), 7.29 (dd, J=1.00, 7.28 Hz, 1H), 5.23-5.50 (m, 1H), 4.96 (s, 2H), 4.49 (br t, J=6.65 Hz, 1H), 2.73 (br s, 1H), 2.47-2.67 (m, 4H), 1.30 (s, 9H), 1.00 (s, 9H), 0.17 (s, 6H).

Step 2. Synthesis of (R)-(6-(6-(6-(amino(3,3-difluorocyclobutyl)methyl)pyridin-2-yl)-1H-indazol-1-yl)pyridin-2-yl)methanol

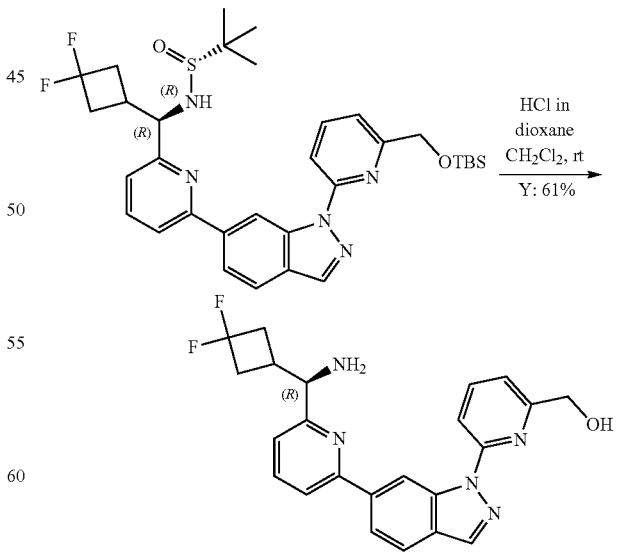

To a solution of (R)-A-((R)-(6-(1-(6-(((tert-butyldimethylsilyl)oxy)methyl)pyridin-2-yl)-1H-indazol-6-yl)pyridin-2-yl)(3,3-difluorocyclobutyl)methyl)-2-methylpropane-2- sulfinamide (0.100 g, 0.156 mmol) in CH₂Cl₂ (4 mL) was added a solution of hydrogen chloride (4.0 M in dioxane, 1.16 mL, 4.64 mmol). The resulting mixture was stirred at room temperature for 2 h. The mixture was diluted with Et₂O and stirred at room temperature for 30 min. The resulting precipitate was filtered to provide (R)-(2-(6-(6-(amino(3,3-difluorocyclobutyl)methyl)pyridin-2-yl)-1H-indazol-1-yl)pyrimidin-4-yl)methanol (0.040 g; 61%). LCMS (ESI+) 422.1 (M+H)⁺. ¹H NMR (400 MHz, DMSO-d₆) δ 9.57-9.61 (m, 1H), 8.57 (br s, 3H), 8.51 (d, J=1.00 Hz, 1H), 8.23 (dd, J=1.51, 8.53 Hz, 1H), 7.99-8.14 (m, 4H), 7.89 (dd, J=0.75, 8.03 Hz, 1H), 7.56 (dd, J=0.88, 7.40 Hz, 1H), 7.42 (dd, J=0.88, 7.40 Hz, 1H), 5.57-5.71 (m, 1H), 4.79 (s, 2H), 4.58-4.70 (m, 1H), 2.64-2.84 (m, 4H).

Example 28 (S)-(2-(6-(6-(amino(3,3-difluorocyclobutyl)methyl)pyridin-2-yl)-17f-indazol-1-yl)pyrimidin-4-yl)methanol Step 1. Synthesis of (R)—N—((S)-(6-(1-(4-(((tert-butyldimethylsilyl)oxy)methyl)pyrimidin-2-yl)-1H-indazol-6-yl)pyridin-2-yl)(3,3-difluorocyclobutyl)methyl)-2-methylpropane-2-sulfinamide

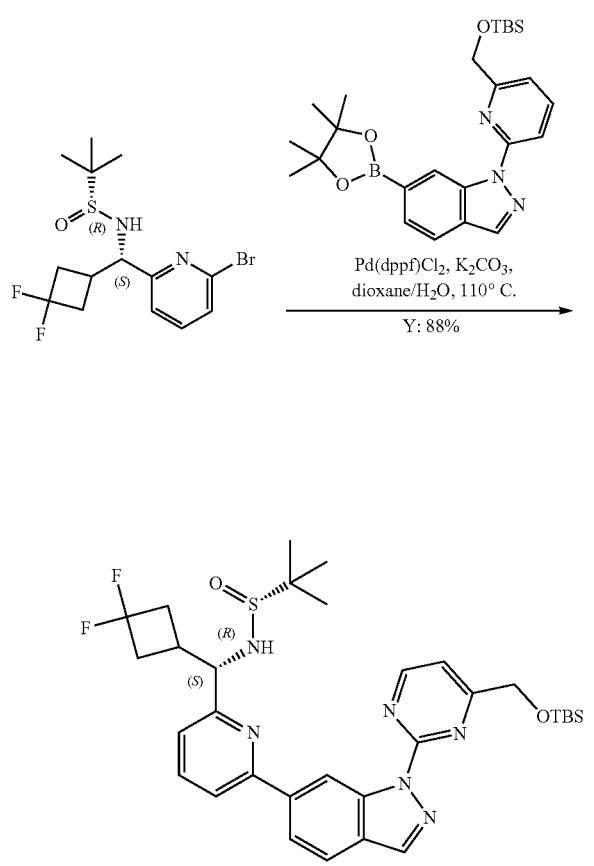

A suspension of 1-(4-(((tert-butyldimethylsilyl)oxy)methyl)pyrimidin-2-yl)-6-(4,4,5,5-tetramethyl-1,3,2-dioxaborolan-2-yl)-1H-indazole (Example 8, Step 4, 0.110 g, 0.236 mmol), K₂CO₃ (81.6 mg, 0.590 mmol), (R)—N—((S)-(6-bromopyridin-2-yl)(3,3-difluorocyclobutyl)methyl)-2-methylpropane-2-sulfinamide (Example 26, Step 4, 0.075 g, 0.20 mmol), and Pd(dppf)Cl₂ (8.0 mg, 0.010 mmol) in dioxane (0.66 mL) and water (0.22 mL) were purged with nitrogen for 15 min then warmed to 110° C. for 2 h. The mixture was cooled to room temperature adsorbed onto silica and purified over SiO₂ (12 g, 50-100% EtOAc:heptane) to provide (R)—N—((S)-(6-(1-(4-(((tert-butyldimethylsilyl)oxy)methyl)pyrimidin-2-yl)-1H-indazol-6-yl)pyridin-2-yl)(3,3-difluorocyclobutyl)methyl)-2-methylpropane-2-sulfinamide (0.111 g; 88%). LCMS (ESI+) 641.1 (M+H)⁺. ¹H NMR (400 MHz, CDCl₃) δ 9.33-9.45 (m, 1H), 8.80-8.91 (m, 1H), 8.32-8.40 (m, 1H), 7.78-8.04 (m, 4H), 7.48 (d, J=5.02 Hz, 1H), 7.27-7.37 (m, 1H), 4.98 (s, 2H), 4.48-4.64 (m, 1H), 2.47-2.90 (m, 5H), 1.31 (s, 9H), 1.00 (s, 9H), 0.17 (d, J=0.75 Hz, 6H).

Step 2. Synthesis of (S)-(2-(6-(6-(amino(3,3-difluorocyclobutyl)methyl)pyridin-2-yl)-1H-indazol-1-yl)pyrimidin-4-yl)methanol

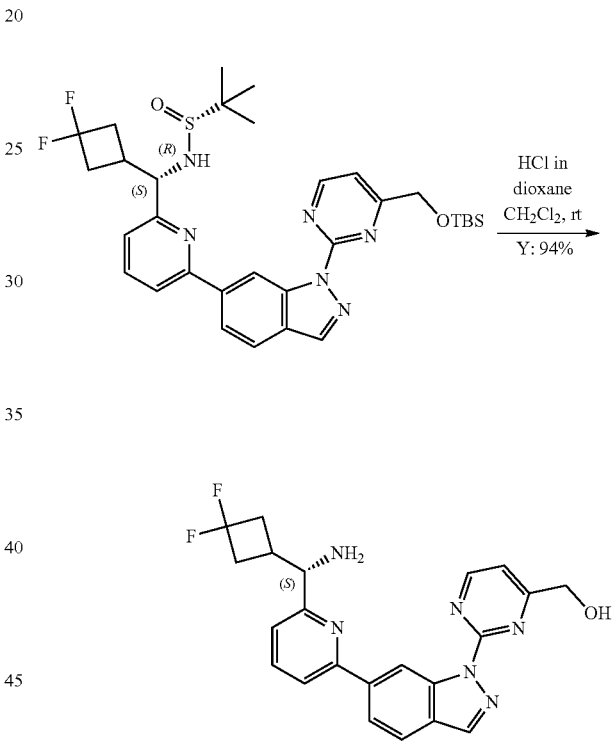

To a solution of (R)—N—((S)-(6-(1-(4-(((tert-butyldimethylsilyl)oxy)methyl)pyrimidin-2-yl)-1H-indazol-6-yl)pyridin-2-yl)(3,3-difluorocyclobutyl)methyl)-2-methylpropane-2-sulfinamide (0.111 g, 0.173 mmol) in CH₂Cl₂ (2 mL) was added a solution of hydrogen chloride (4.0 M in dioxane, 0.650 mL, 2.60 mmol). The resulting mixture was stirred at room temperature for 2 h. The mixture was diluted with Et₂O and stirred at room temperature for 30 min. The resulting precipitate was filtered to provide (5)-(2-(6-(6-(amino(3,3-difluorocyclobutyl)methyl)pyridin-2-yl)-1H-indazol-1-yl)pyrimidin-4-yl)methanol (0.069 g; 94%). LCMS (ESI+) 423.1 (M+H)⁺. ¹H NMR (400 MHz, DMSO-d₆) δ 9.43 (d, J=0.75 Hz, 1H), 8.93 (d, J=5.02 Hz, 1H), 8.72 (br s, 4H), 8.53 (d, J=0.75 Hz, 1H), 8.27 (dd, J=1.51, 8.28 Hz, 1H), 7.99-8.17 (m, 3H), 7.51-7.62 (m, 2H), 4.75 (s, 2H), 4.59-4.68 (m, 1H), 2.58-2.92 (m, 4H), 2.52-2.59 (m, 1H).

Example 29 (S)-(3,3-difluorocyclobutyl)(6-(1-(6-(fluoromethyl)pyridin-2-yl)-1H-indazol-6-yl)pyridin-2-yl)methanamine Synthesis of (S)-(3,3-difluorocyclobutyl)(6-(1-(6-(fluoromethyl)pyridin-2-yl)-1H-indazol-6-yl)pyridin-2-yl) methanamine

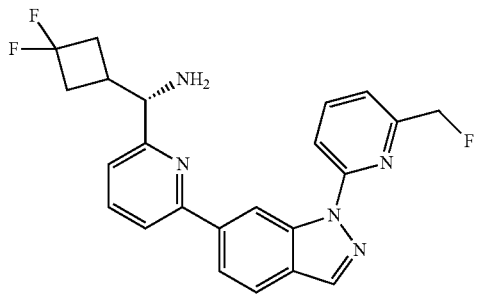 [SMILES: N[C@H](c1cccc(-c2ccc3cnn(-c4cccc(CF)n4)c3c2)n1)C1CC(F)(F)C1]

Preparation of the title compound was similar to that of Example 26 except that 1-(6-(fluoromethyl)pyridin-2-yl)-6-(4,4,5,5-tetramethyl-1,3,2-dioxaborolan-2-yl)-1H-indazole (Example 16, Step 2) in place of 1-(6-(((tert-butyldimethylsilyl)oxy)methyl)pyridin-2-yl)-6-(4,4,5,5-tetramethyl-1,3,2-dioxaborolan-2-yl)-1H-indazole and was purified by HPLC to give the title compound as a TFA salt (58 mg, 80%). LCMS: RT 1.26 min.; MH+424.0; $^1$H NMR (400 MHz, DMSO-d6) δ 9.52 (s, 1H), 8.48-8.66 (m, 3H), 8.21 (dd, J=1.25, 8.53 Hz, 1H), 7.96-8.17 (m, 5H), 7.56 (d, J=7.28 Hz, 1H), 7.46 (d, J=7.28 Hz, 1H), 5.60-5.83 (m, 2H), 4.65 (br. s., 1H), 2.59-2.87 (m, 5H).

Example 30 (S)-(3,3-difluorocyclobutyl)(6-(1-(6-(difluoromethyl)pyridin-2-yl)-1H-indazol-6-yl)pyridin-2-yl) methanamine Synthesis of (S)-(3,3-difluorocyclobutyl)(6-(1-(6-(difluoromethyl)pyridin-2-yl)-1H-indazol-6-yl)pyridin-2-yl)methanamine

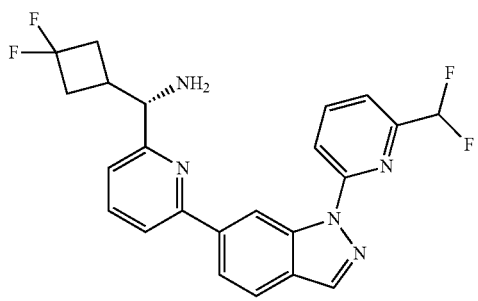 [SMILES: N[C@H](c1cccc(-c2ccc3cnn(-c4cccc(C(F)F)n4)c3c2)n1)C1CC(F)(F)C1]

Preparation of the title compound was similar to that of example 26 except that 1-(6-(difluoromethyl)pyridin-2-yl)-6-(4,4,5,5-tetramethyl-1,3,2-dioxaborolan-2-yl)-1H-indazole (Example 14, Step 3) in place of 1-(6-(((tert-butyldimethylsilyl)oxy)methyl)pyridin-2-yl)-6-(4,4,5,5-tetramethyl-1,3,2-dioxaborolan-2-yl)-1H-indazole and was purified by HPLC to give the title compound as a TFA salt (58 mg, 65%). LCMS: RT 1.29 min.; MH+442.0; $^1$H NMR (400 MHz, DMSO-d6) δ 9.51 (s, 1H), 8.59 (s, 3H), 8.16-8.32 (m, 3H), 8.01-8.13 (m, 3H), 7.66 (d, J=6.53 Hz, 1H), 7.57 (dd, J=1.88, 6.40 Hz, 1H), 7.01-7.40 (m, 1H), 4.64 (br. s., 1H), 2.56-2.87 (m, 5H).

Example 31 and 32 (S)-(6-(6-(6-(amino(1-fluorocyclobutyl)methyl)pyridin-2-yl)-1H-indazol-1-yl)pyridin-2-yl)methanol & (A)-(6-(6-(6-(amino(1-fluorocyclobutyl)methyl)pyridin-2-yl)-1H-indazol-1-yl)pyridin-2-yl)methanol

Step 1. Synthesis of 1-fluoro-N-methoxy-N-methyl-cyclobutane-1-carboxamide

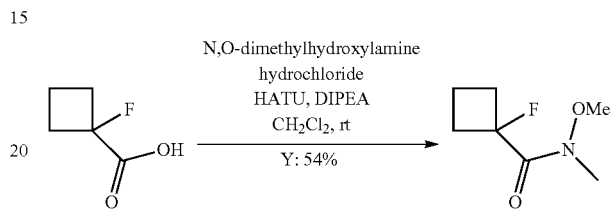

HATU (3.55 g, 9.32 mmol) and N,O-dimethylhydroxylamine hydrochloride (0.908 g, 9.32 mmol) were suspended in CH$_2$Cl$_2$ (32 mL). N,N-Diisopropylethylamine (3.52 mL, 25.4 mmol) was added followed by a solution of 1-fluorocyclobutanecarboxylic acid (1.00 g, 8.47 mmol) in CH$_2$Cl$_2$ (10 mL). The mixture was stirred at room temperature for 16 h. The solution was concentrated in vacuo and the residue was partitioned between CH$_2$Cl$_2$ (200 mL) and saturated NH$_4$Cl (100 mL). The aqueous layer was extracted with CH$_2$Cl$_2$ (200 mL) and the combined organics were dried over Na$_2$SO$_4$ and then concentrated. The residue was purified by silica gel chromatography to afford 1-fluoro-N-methoxy-A-methyl-cyclobutanecarboxamide (0.744 g, 54%). $^1$H NMR (400 MHz, CDCl$_3$) δ 3.70 (s, 3H), 3.20-3.23 (m, 3H), 2.68 (m, 2H), 2.25-2.51 (m, 2H), 1.81-1.99 (m, 1H), 1.52-1.72 (m, 1H).

Step 2. Synthesis of (6-bromopyridin-2-yl)(1-fluorocyclobutyl)methanone

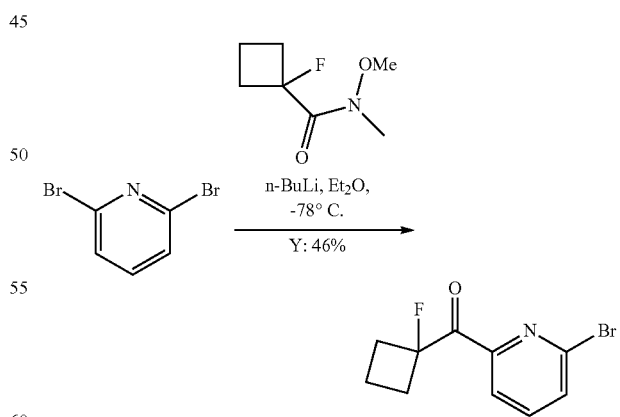

To a suspension of 2,6-dibromopyridine (1.09 g, 4.62 mmol) in Et$_2$O (23 mL) at −78° C. was added a solution of n-butyl lithium (2.5 M in hexanes, 2.03 mL, 5.08 mmol). After 30 min, 1-fluoro-N-methoxy-N-methyl-cyclobutanecarboxamide (0.744 g, 4.62 mmol) in Et$_2$O (5 mL) was added. After 15 minutes, the reaction was allowed to warm to −10° C. over 30 min then quenched by addition of saturated NH₄Cl. The layers were separated and the aqueous layer was extracted once with diethyl ether. The combined ether layers were washed with brine, dried over MgSO₄, filtered, and concentrated. The residue was purified over SiO₂ (80 g, 10-30% EtOAc in heptane) to afford (6-bromo-2-pyridyl)-(1-fluorocyclobutyl)methanone (0.55 g, 46%). ¹H NMR (400 MHz, CDCl₃) δ 7.93 (dd, J=0.75, 7.28 Hz, 1H), 7.69-7.75 (m, 1H), 7.63-7.68 (m, 1H), 2.82-3.03 (m, 2H), 2.51-2.73 (m, 2H), 2.00-2.17 (m, 1H), 1.83-1.98 (m, 1H).

Step 3. Synthesis of (R)—N-((6-bromopyridin-2-yl)(1-fluorocyclobutyl)methylene)-2-methylpropane-2-sulfinamide

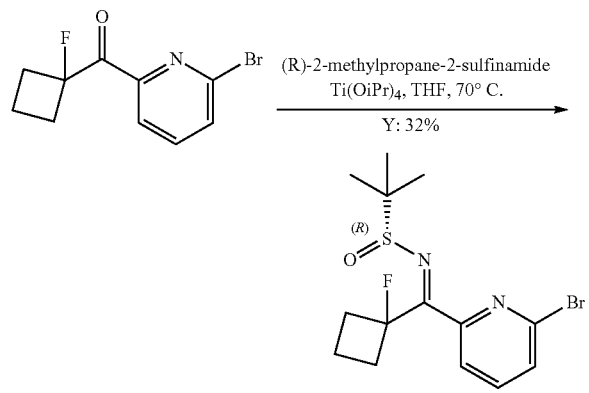

A solution of (6-bromo-2-pyridyl)-(1-fluorocyclobutyl)methanone (0.276 g, 1.07 mmol) in anhydrous THF (5.3 mL) was treated with (R)-(+)-2-methyl-2-propanesulfinamide (0.260 g, 2.14 mmol) and titanium tetraisopropoxide (1.27 mL, 4.28 mmol). The mixture was heated to 70° C. for 4 h. The mixture was cooled to room temperature and quenched by addition of water (1 mL) and EtOAc (20 mL). The suspension was filtered through Celite and rinsed with EtOAc. The residue was purified over SiO₂ (80 g, 10-30% EtOAc in heptane) to afford (R)—N-[(6-bromo-2-pyridyl)-(1-fluorocyclobutyl)methylene]-2-methyl-propane-2-sulfinamide (0.122 g, 32% yield). ¹H NMR (400 MHz, CDCl₃) δ 7.53-7.61 (m, 1H), 7.47-7.52 (m, 1H), 7.35 (td, J=1.13, 7.53 Hz, 1H), 2.80-3.03 (m, 2H), 2.43-2.69 (m, 2H), 1.94-2.08 (m, 1H), 1.74-1.89 (m, 1H), 1.31 (s, 9H).

Step 4. Synthesis of (R)—N-((6-bromopyridin-2-yl)(1-fluorocyclobutyl)methyl)-2-methylpropane-2-sulfinamide

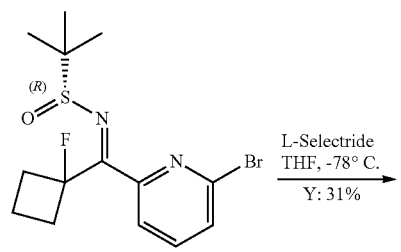

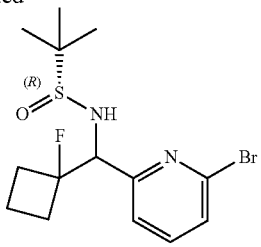

To a solution of (R)—N-[(6-bromo-2-pyridyl)-(1-fluorocyclobutyl)methylene]-2-methyl-propane-2-sulfinamide (0.122 g, 0.338 mmol) in THF (1.69 mL) at −78° C. was added a solution of L-Selectride (1.0 M in THF, 0.675 mL, 0.675 mmol) dropwise. The mixture was stirred for 60 minutes at −78° C., and then quenched by addition of saturated NH₄Cl. The mixture was extracted with EtOAc, dried over MgSO₄, filtered, and concentrated. The residue was purified over SiO₂ (12 g, 20-100% EtOAc in heptane) to provide a mixture of diastereomeric products (38.00 mg, 31%). ¹H NMR (400 MHz, CDCl₃) δ 7.49-7.59 (m, 2H), 7.39-7.45 (m, 2H), 7.30-7.38 (m, 2H), 5.00 (d, J=8.28 Hz, 1H), 4.60-4.71 (m, 1H), 4.50 (dd, J=8.41, 18.20 Hz, 1H), 4.18 (br d, J=6.02 Hz, 1H), 2.09-2.66 (m, 8H), 1.82-1.96 (m, 2H), 1.51-1.66 (m, 2H), 1.29 (s, 9H), 1.20 (s, 9H).

Step 5. Synthesis of (R)—N-((6-(1-(6-(((tert-butyldimethylsilyl)oxy)methyl)pyridin-2-yl)-1H-indazol-6-yl)pyridin-2-yl)(1-fluorocyclobutyl)methyl)-2-methylpropane-2-sulfinamide

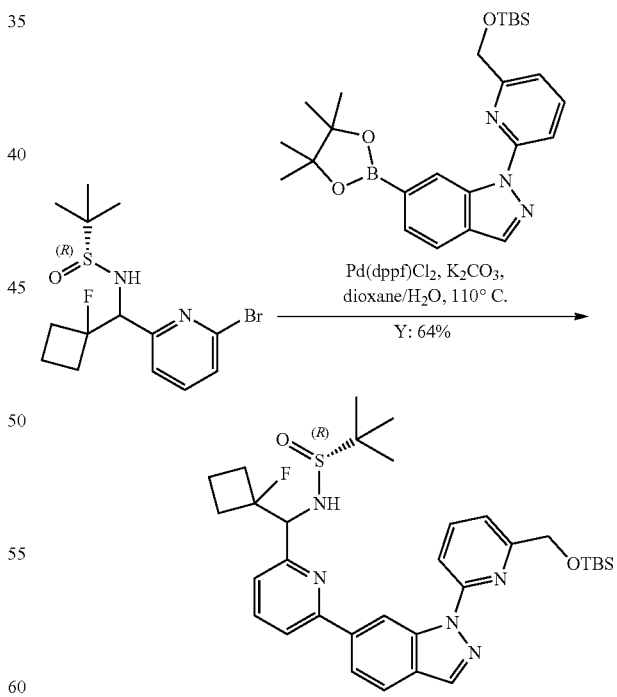

A suspension of tert-butyl-dimethyl-[[6-[6-(4,4,5,5-tetramethyl-1,3,2-dioxaborolan-2-yl)indazol-1-yl]-2-pyridyl]methoxy]silane (0.096 g, 0.206 mmol), K₂CO₃ (0.086 g, 0.619 mmol), (R)—N-((6-bromopyridin-2-yl)(1-fluorocyclobutyl)methyl)-2-methylpropane-2-sulfinamide (0.075 g, 0.206 mmol), and Pd(dppf)Cl₂ (0.015 g, 0.02 mmol) in dioxane (0.4 mL) and water (0.12 mL) were purged with nitrogen for 15 minutes then warmed to 110° C. for 2 hours. The mixture was cooled to room temperature, adsorbed onto silica and purified over SiO$_2$ (12 g, 50-100% EtOAc in heptane) to provide desired product as a mixture of diastereomers (0.082 mg, 64%). LCMS (ESI+) 622.3 (M+H)$^+$. $^1$H NMR (400 MHz, CDCl$_3$) δ 9.38 (s, 1H), 9.29-9.35 (m, 1H), 8.23 (dd, J=0.75, 3.77 Hz, 2H), 7.75-8.08 (m, 15H), 7.35-7.48 (m, 5H), 5.60 (br d, J=7.78 Hz, 1H), 4.94-5.02 (m, 5H), 4.82-4.94 (m, 1H), 4.53-4.81 (m, 2H), 2.16-2.78 (m, 9H), 1.81-2.10 (m, 9H), 1.58 (qd, J=8.86, 17.85 Hz, 4H), 1.30 (s, 10H), 1.21 (s, 12H), 0.98-1.02 (m, 21H), 0.17 (d, J=2.76 Hz, 14H).

Step 6. Synthesis of (S)-(6-(6-(6-(amino(1-fluorocyclobutyl)methyl)pyridin-2-yl)-1H-indazol-1-yl)pyridin-2-yl)methanol & (R)-(6-(6-(6-(amino(1-fluorocyclobutyl)methyl)pyridin-2-yl)-1H-indazol-1-yl)pyridin-2-yl)methanol

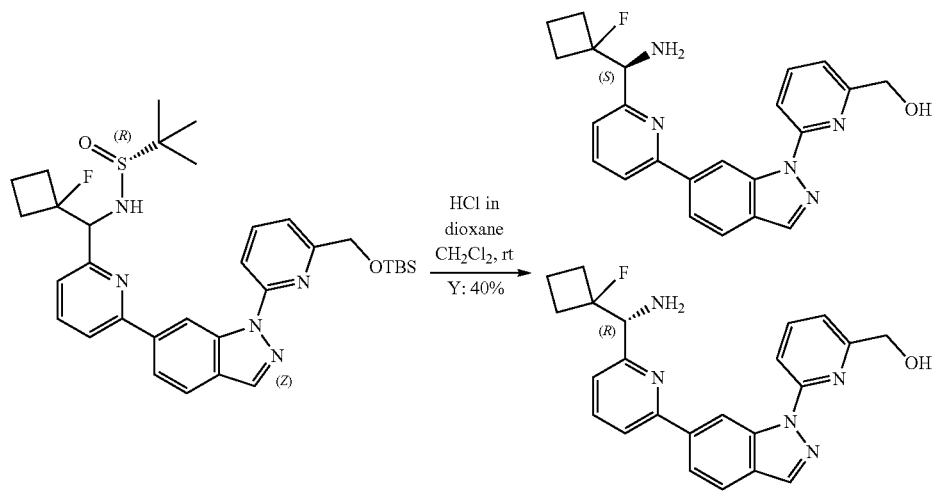

To a solution of (R)—N-((6-(1-(6-(((tert-butyldimethylsilyl)oxy)methyl)pyridin-2-yl)-1H-indazol-6-yl)pyridin-2-yl)(1-fluorocyclobutyl)methyl)-2-methylpropane-2-sulfinamide (0.082 g, 0.131 mmol) in CH$_2$Cl$_2$ (0.7 mL) was added a solution of hydrogen chloride (4.0 M in dioxane, 0.70 mL, 2.80 mmol). The resulting mixture was stirred at room temperature for 2 h. The mixture was diluted with Et$_2$O and stirred at room temperature for 30 min. The resulting precipitate was filtered to provide a mixture of enantiomers. The enantiomers were isolated using chiral SFC (column: CHIRALPAK AD-H 30×250 mm, 5 um. Co-solvent: 25% ethanol with 0.1% DEA in CO$_2$ (flow rate: 100 mL/min) 120 bar). Peak 1: (8.90 mg, 17%). LCMS (ESI+) 404.2 (M+H)$^+$. $^1$H NMR (400 MHz, METHANOL-d$_4$) δ 9.57 (td, J=0.75, 1.51 Hz, 1H), 8.27 (d, J=1.00 Hz, 1H), 7.86-8.02 (m, 6H), 7.47 (d, J=7.03 Hz, 1H), 7.36-7.41 (m, 1H), 4.84 (s, 2H), 4.25 (d, J=19.33 Hz, 1H), 2.46-2.71 (m, 2H), 2.12-2.44 (m, 2H), 1.74-1.86 (m, 1H), 1.20-1.32 (m, 1H). Peak 2: (12.00 mg, 23%). LCMS (ESI+) 404.2 (M+H)$^+$. $^1$H NMR (400 MHz, METHANOL-d$_4$) δ 9.56 (s, 1H), 8.27 (s, 1H), 7.81-8.05 (m, 6H), 7.47 (d, J=7.03 Hz, 1H), 7.38 (dd, J=2.76, 5.77 Hz, 1H), 4.83 (s, 2H), 4.24 (d, J=19.33 Hz, 1H), 2.46-2.72 (m, 2H), 2.13-2.44 (m, 2H), 1.73-1.87 (m, 1H), 1.18-1.32 (m, 1H).

Example 33 Synthesis of (R)-(6-(6-(6-(amino(3,3-difluorocyclobutyl)methyl)pyridin-2-yl)-4-ethoxy-1H-indazol-1-yl)pyridin-2-yl)methanol

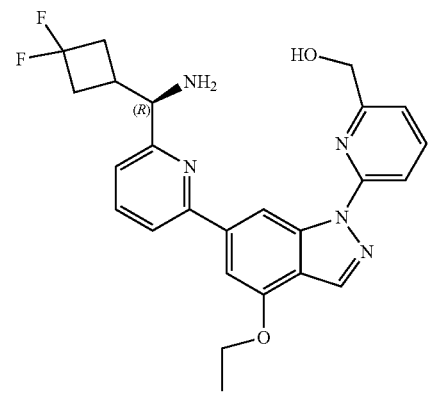

Using a sequence of steps similar to that described in example 24 except that 6-bromo-4-ethoxy-1H-indazole was used instead of 6-bromo-4-methoxy-1H-indazole was used in Step 4 and (R)—N—((R)-(6-bromopyridin-2-yl)(3,3-difluorocyclobutyl)methyl)-2-methylpropane-2-sulfinamide (Example 26, Step 4) was used in place of (R)—N—((S)-(6-bromopyridin-2-yl)(cis-3-hydroxycyclobutyl)methyl)-2-methylpropane-2-sulfinamide in Step 10 to give the title compound. $^1$H NMR (400 MHz, DMSO-d$_6$) 5 ppm 9.09-9.17 (m, 1H) 8.74 (br s, 3H) 8.43 (d, J=0.8 Hz, 1H) 8.08-8.16 (m, 1H) 7.95-8.07 (m, 2H) 7.87 (dd, J=8.2, 0.6 Hz, 1H) 7.62 (d, J=1.0 Hz, 1H) 7.57 (d, J=7.5 Hz, 1H) 7.41 (dd, J=7.5, 0.8 Hz, 1H) 4.77 (s, 2H) 4.62 (br s, 1H) 4.38-4.49 (m, 2H) 2.56-2.95 (m, 4H) 1.51 (t, J=7.0 Hz, 3H). LCMS (M+H)=466.2. HPLC purity>99%

Example 34 Synthesis of (S)-(6-(6-(6-(amino(3,3-difluorocyclobutyl)methyl)pyridin-2-yl)-4-ethoxy-1H-indazol-1-yl)pyridin-2-yl)methanol

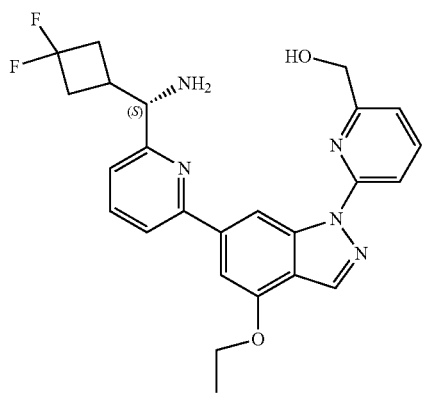

Using a sequence of steps similar to that described in example 24 except that 6-bromo-4-ethoxy-1H-indazole was used instead of 6-bromo-4-methoxy-1H-indazole was used in Step 4 and (R)—N—((S)-(6-bromopyridin-2-yl)(3,3-difluorocyclobutyl)methyl)-2-methylpropane-2-sulfinamide (Example 26, Step 4) was used in place of (R)—N—((S)-(6-bromopyridin-2-yl)(cis-3-hydroxycyclobutyl)methyl)-2-methylpropane-2-sulfinamide in Step 10 to give the title compound. $^1$H NMR (400 MHz, DMSO-d$_6$) δ ppm 9.09-9.17 (m, 1H) 8.74 (br s, 3H) 8.43 (d, J=0.8 Hz, 1H) 8.08-8.16 (m, 1H) 7.95-8.07 (m, 2H) 7.87 (dd, J=8.2, 0.6 Hz, 1H) 7.62 (d, J=1.0 Hz, 1H) 7.57 (d, J=7.5 Hz, 1H) 7.41 (dd, J=7.5, 0.8 Hz, 1H) 4.77 (s, 2H) 4.62 (br s, 1H) 4.38-4.49 (m, 2H) 2.56-2.95 (m, 4H) 1.51 (t, J=7.0 Hz, 3H). LCMS (M+H)=466.2. HPLC purity 98.7%.

Example 35 Synthesis of Additional Compounds

The following compounds were synthesized according to the procedures generally described herein.

a) 3-((S)-amino(6-(1-(6-(difluoromethyl)pyridin-2-yl)-1H-indazol-6-yl)pyridin-2-yl)methyl)cyclobutan-1-ol (35a)

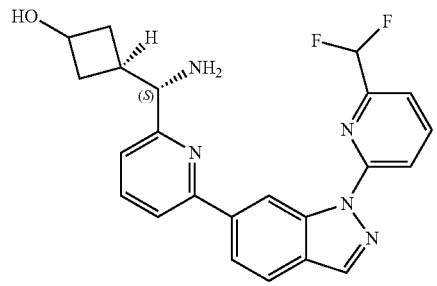

b) 3-((S)-amino(6-(1-(6-ethylpyridin-2-yl)-1H-indazol-6-yl)pyridin-2-yl)methyl)cyclobutan-1-ol (35b)

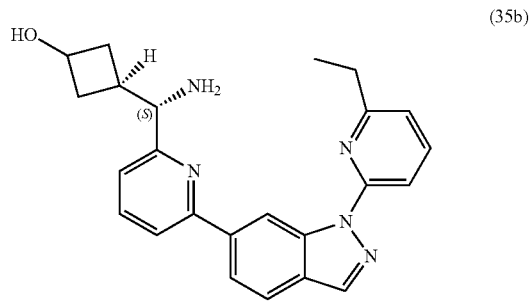

c) (R)-(6-(6-(6-(amino(1-fluorocyclobutyl)methyl)pyridin-2-yl)-1H-indazol-1-yl)pyridin-2-yl) methanol (35c)

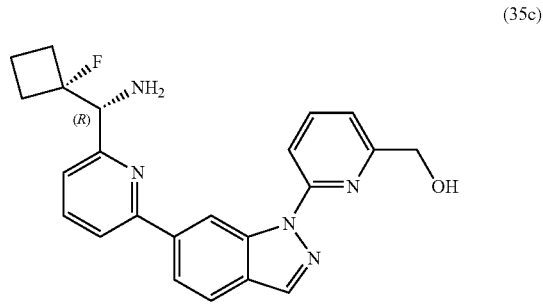

d) (S)-(6-(6-(6-(amino(1-fluorocyclobutyl)methyl)pyridin-2-yl)-1H-indazol-1-yl)pyridin-2-yl) methanol (35d)

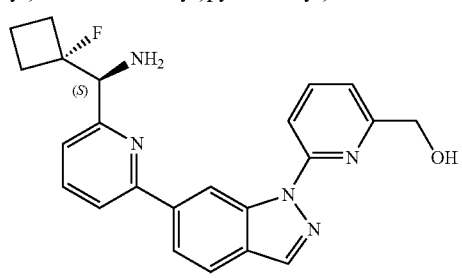

e) (S)-3-(amino(6-(1-(6-methoxypyridin-2-yl)-1H-indazol-6-yl)pyridin-2-yl)methyl)cyclobutan-1-ol (35e)

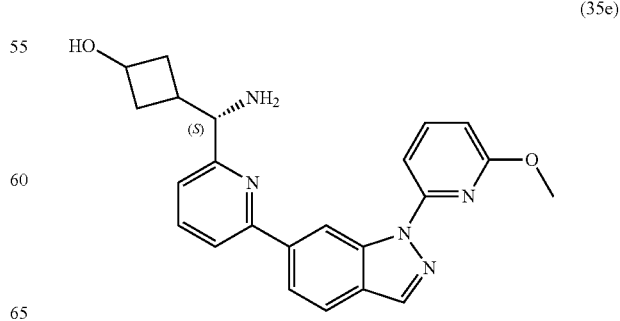

f) 3-((S)-amino(6-(1-(6-(fluoromethyl)pyridin-2-yl)-1H-indazol-6-yl)pyridin-2-yl)methyl)-1-methylcyclobutan-1-ol (35f)

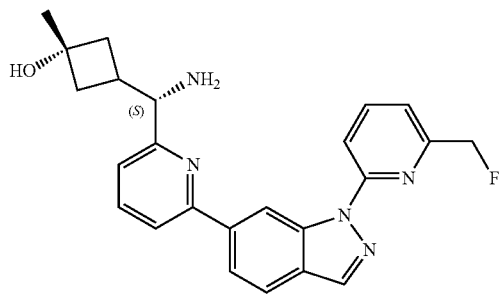

g) 3-((S)-amino(6-(1-(6-(difluoromethyl)pyridin-2-yl)-1H-indazol-6-yl)pyridin-2-yl)methyl)-1-methylcyclobutan-1-ol (35g)

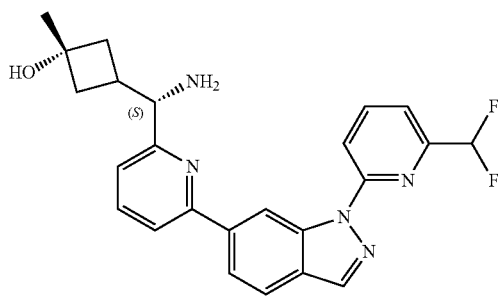

h) (S)-(6-(1-(6-(difluoromethyl)pyridin-2-yl)-1H-indazol-6-yl)pyridin-2-yl)(3-methoxycyclobutyl)methanamine (35h)

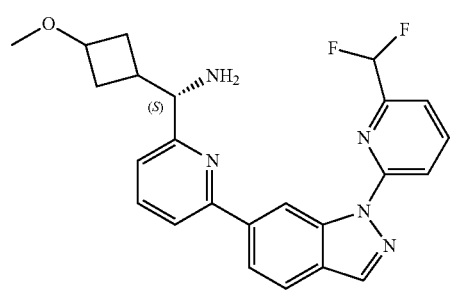

i) 3-((S)-amino(6-(1-(6-(fluoromethyl)pyridin-2-yl)-1H-indazol-6-yl)pyridin-2-yl)methyl)-1-methylcyclobutan-1-ol (35i)

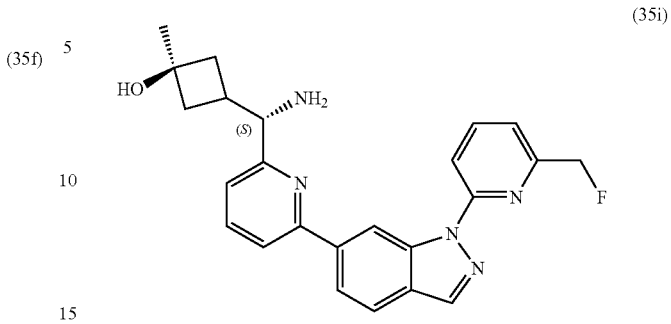

j) (S)-(6-(1-(6-(difluoromethyl)pyridin-2-yl)-1H-indazol-6-yl)pyridin-2-yl)((1R,3S)-3-methoxycyclobutyl)methanamine (35j)

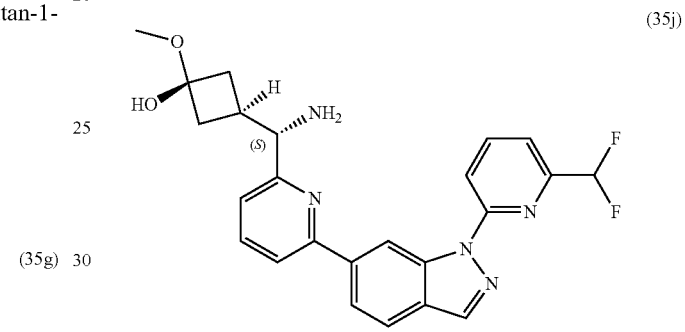

k) (S)-(6-(1-(6-(fluoromethyl)pyridin-2-yl)-1H-indazol-6-yl)pyridin-2-yl)(1-methylcyclobutyl)methanamine (35k)

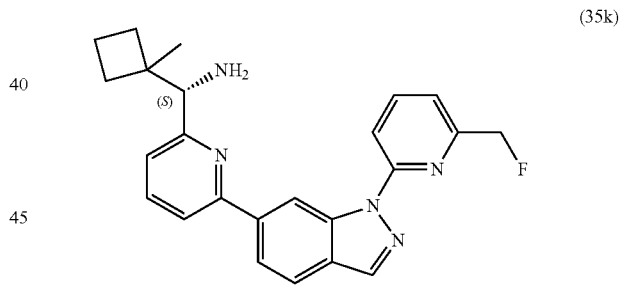

l) (S)-3-(amino(6-(1-(6-(fluoromethyl)pyridin-2-yl)-1H-indazol-6-yl)pyridin-2-yl)methyl)cyclobutane-1-carbonitrile (35l)

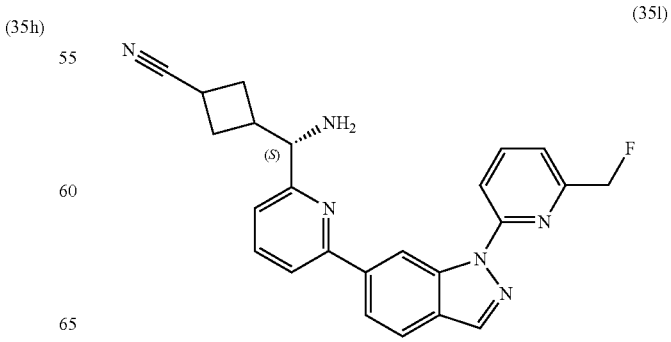

Example 36

Biochemical Assay: The biochemical assay is in a AlphaScreen format. The kinase reaction is based on the IRAK-4 phosphorylation of a biotin labeled peptide. The phosphopeptide is incubated with anti-phosphothreonine antibody as well as streptavidin- and protein A-coated beads. Binding of the protein-A coated beads to the antibody and the streptavidin beads to the peptide, leads to an energy transfer from one bead to the other, ultimately producing a luminescent/fluorescent signal.

Generally, the kinase reaction is carried out at 1 nM IRAK4, 1.6 µM peptide, 1 mM ATP in reaction buffer 50 mM Hepes, 60 mM NaCl, 5 mM $MgCl_2$, 0.25 mM $MnCl_2$, 2 mM DTT, 0.01% BSA, 0.01% Tween-20) for 3.5 h at RT.

The compounds described herein were tested for in the above biochemical assay. The results are provided below, wherein the compound number corresponds to the numbers set forth in the examples above, "+" represents an IC50 of less than 10 uM, but greater than 1 uM, "++" represents an IC50 of less than or equal to 1 uM but greater than 0.1 uM, and a "+++" represents an IC50 of less than or equal to 0.1 uM.

| IC50 | Compounds |
| --- | --- |
| +++ | 1, 2, 3, 4, 5, 6, 7, 8, 9, 10, 12, 13, 14, 15, 16, 17, 19, 20, 21, 22, 23, 24, 25, 26, 27, 28, 29, 30, 31, 32, 33, 34, 35a, 35b, 35c, 35d, 35f, 35g and 35h |
| ++ | 11, 18, 35e and 35i |
| + | |
| greater than 10 µM | |

Cell-based Assay: The cell-based assays is based on IL-6 ELISA quantification. Briefly, A549 cells are cultured in DMEM with 10% FBS medium. When cells reach 80% confluence they are trypsin treated and seeded 180 ul/well in 96-well plate at 2.5×10^4 cells/well. Then, 20 ul of compound serial dilutions (starting at 10 uM, 10 points) are added to the cell plate; incubate for 30 min at 37 C and stimulated with 2 ng/ml human IL-1beta 37 C, 5% $CO_2$ overnight. The next day 100 ul of cell supernatant per well are analyzed on a Human IL-6 Quantikine ELISA kit from R&D Systems.

The compounds described herein were tested for in the above biochemical and cell-based assays. The results are provided below, wherein the compound number corresponds to the numbers set forth in the examples above, "†" represents an EC50 of greater than 10 uM, "††" represents an EC50 of equal to or less than 10 uM but greater than 1 uM, and "†††" represents an EC50 of equal to or less than 1 uM.

| EC50 | Compounds |
| --- | --- |
| ††† | 1, 2, 3, 4, 5, 6, 7, 8, 9, 10, 11, 13, 14, 15, 16, 17, 21, 23, 24, 26, 27, 28, 29, 30, 33, 34, 35a, 35d, 35g, 35h, 35j and 35l |
| †† | 12, 22, 25, 35b, 35c, 35e, 35f, 35i, 35k |
| † | |

What is claimed is:
1. A compound of Formula (I):

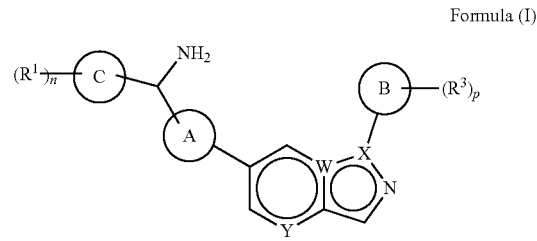

Formula (I)

or a pharmaceutically acceptable salt thereof, wherein:
Ring A is selected from phenyl and 5- or 6-membered heteroaryl;
Ring B is selected from phenyl and 5- or 6-membered heteroaryl;
Ring C is a 3- to 6-membered carbocyclyl,
n is 1, 2 or 3;
p is 0, 1, or 2;
one of W and X is N, and the other of W and X is C;
Y is N or C—$R^2$;
$R^1$ is selected from $C_{1-6}$alkyl, $C_{2-6}$alkenyl, $C_{2-6}$alkynyl, halo, —CN, —C($R^{1a}$)=N($R^{1a}$), —C(O)$R^{1a}$, —C(O)$_2R^{1a}$, —C(O)N($R^{1a}$)$_2$, —$NO_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N($R^{1a}$)$_2$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$ alkenyl, and $C_{2-6}$ alkynyl are optionally substituted with one or more $R^{10}$;
$R^{1a}$ in each occurrence is independently selected from H or $C_{1-6}$alkyl wherein said $C_{1-6}$ alkyl in each occurrence are optionally and independently substituted with one or more $R^{10}$;
$R^{10}$ in each occurrence is independently selected from halo, —CN, —C($R^{10a}$)=N($R^{10a}$), —C(O)$R^{10a}$, —C(O)$_2R^{10a}$, —C(O)N($R^{10a}$)$_2$, —$NO_2$, —N($R^{10a}$)$_2$, —N($R^{10a}$)C(O)$R^{10a}$, —N($R^{10a}$)C(O)$_2R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$;
$R^{10a}$ in each occurrence is independently selected from H and $C_{1-6}$alkyl, wherein said $C_{1-6}$alkyl is optionally substituted with one or more halo;
$R^2$ is selected from H, $C_{1-6}$alkyl, $C_{2-6}$alkenyl, $C_{2-6}$alkynyl, 3- to 7-membered carbocyclyl, 3- to 7-membered heterocyclyl, halo, —CN, —C($R^{2a}$)=N($R^{2a}$), —C(O)$R^{2a}$, —C(O)$_2R^{2a}$, —C(O)N($R^{2a}$)$_2$, —$NO_2$, —N($R^{2a}$)$_2$, —N($R^{2a}$)C(O)$R^{2a}$, —N($R^{2a}$)C(O)$_2R^{2a}$, —N($R^{2a}$)C(O)N($R^{2a}$)$_2$, —N($R^{2a}$)S(O)$_2R^{2a}$, —OC(O)$R^{2a}$, —OC(O)N($R^{2a}$)$_2$, —S$R^{2a}$, —S(O)$R^{2a}$, —S(O)$_2R^{2a}$, —S(O)N($R^{2a}$)$_2$, and —S(O)$_2$N($R^{2a}$)$_2$, wherein said $C_{1-6}$alkyl, $C_{2-6}$alkenyl, $C_{2-6}$alkynyl, 3- to 7-membered carbocyclyl, and 3-7 membered heterocyclyl are optionally substituted with one or more $R^{20}$;
$R^{2a}$ in each occurrence is independently selected from H and $C_{1-6}$alkyl, wherein said $C_{1-6}$ alkyl in each occurrence is optionally and independently substituted with one or more $R^{20}$;
$R^{20}$ in each occurrence is independently selected from $C_{1-6}$alkyl, $C_{2-6}$alkenyl, $C_{2-6}$alkynyl, $C_{3-7}$ cycloalkyl, 3- to 7-membered saturated heterocyclyl, halo, —CN, —C($R^{20a}$)=N($R^{20a}$), —C(O)$R^{20a}$, C(O)$_2R^{20a}$, —C(O)N($R^{20a}$)$_2$, —$NO_2$, —N($R^{20a}$)$_2$, —N(R$^{20a}$)C(O)R$^{20a}$, —N(R$^{20a}$)C(O)$_2$R$^{20a}$, —N(R$^{20a}$)C(O)N(R$^{20a}$)$_2$, —N(R$^{20a}$)S(O)$_2$R$^{20a}$, —OR$^{20a}$, —OC(O)R$^{20a}$, —OC(O)N(R$^{20a}$)$_2$, —SR$^{20a}$, —S(O)R$^{20a}$, —S(O)$_2$R$^{20a}$, —S(O)N(R$^{20a}$)$_2$, and —S(O)$_2$N(R$^{20a}$)$_2$, wherein said $C_{1-6}$ alkyl, $C_{2-6}$ alkenyl, $C_{2-6}$ alkynyl, $C_{3-7}$ cycloalkyl, and 3-7 membered saturated heterocyclyl in each occurrence are optionally and independently substituted with one or more R$^{25}$;

R$^{20a}$ in each occurrence is independently selected from H and $C_{1-6}$alkyl, wherein said $C_{1-6}$alkyl is optionally substituted with R$^{25}$;

R$^{25}$ is selected from halo and —OR$^{25a}$;

R$^{25a}$ is selected from H and $C_{1-6}$alkyl;

R$^3$ is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —C(R$^{3a}$)=N(R$^{3a}$), —C(O)R$^{3a}$, —C(O)$_2$R$^{3a}$, —C(O)N(R$^{3a}$)$_2$, —NO$_2$, —N(R$^{3a}$)$_2$, —N(R$^{3a}$)C(O)R$^{3a}$, —N(R$^{3a}$)C(O)$_2$R$^{3a}$, —N(R$^{3a}$)C(O)N(R$^{3a}$)$_2$, —N(R$^{3a}$)S(O)$_2$R$^{3a}$, —OR$^{3a}$, —OC(O)R$^{3a}$, —OC(O)N(R$^{3a}$)$_2$, —SR$^{3a}$, —S(O)R$^{3a}$, —S(O)$_2$R$^{3a}$, —S(O)N(R$^{3a}$)$_2$, and —S(O)$_2$N(R$^{3a}$)$_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one or more R$^{30}$;

R$^{3a}$ in each occurrence is independently selected from H, $C_{1-6}$ alkyl, 3- to 6-membered carbocyclyl, and 3- to 6-membered heterocyclyl, wherein said $C_{1-6}$alkyl, 3- to 6-membered carbocyclyl, and 3- to 6-membered heterocyclyl in each occurrence are optionally and independently substituted with one or more R$^{30}$;

R$^{30}$ in each occurrence is independently selected from $C_{1-6}$alkyl, $C_{2-6}$alkenyl, $C_{2-6}$alkynyl, 3- to 6-membered carbocyclyl, 3- to 6-membered heterocyclyl, halo, —CN, —C(R$^{30a}$)=N(R$^{30a}$), —C(O)R$^{30a}$, —C(O)$_2$R$^{30a}$, —C(O)N(R$^{30a}$)$_2$, —NO$_2$, —N(R$^{30a}$)$_2$, —N(R$^{30a}$)C(O)R$^{30a}$, —N(R$^{30a}$)C(O)$_2$R$^{30a}$, —N(R$^{30a}$)C(O)N(R$^{30a}$)$_2$, —N(R$^{30a}$)S(O)$_2$R$^{30a}$, —OR$^{30a}$, —OC(O)R$^{30a}$, —OC(O)N(R$^{30a}$)$_2$, —SR$^{30a}$, —S(O)R$^{30a}$, —S(O)$_2$R$^{30a}$, —S(O)N(R$^{30a}$)$_2$ and —S(O)$_2$N(R$^{30a}$)$_2$, wherein said $C_{1-6}$alkyl, $C_{2-6}$alkenyl, $C_{2-6}$alkynyl, 3-6 membered carbocyclyl, 3- to 6-membered heterocyclyl in each occurrence are optionally and independently substituted with one or more R$^{35}$;

R$^{30a}$ in each occurrence is independently selected from H and $C_{1-4}$alkyl, wherein $C_{1-4}$alkyl is optionally substituted with one or more R$^{35}$;

R$^{35}$ in each occurrence is independently selected from halo and —OR$^{35a}$; and R$^{35a}$ in each occurrence is independently selected from H and $C_{1-6}$alkyl.

2. The compound of claim 1, wherein the compound is represented by the following structural formula:

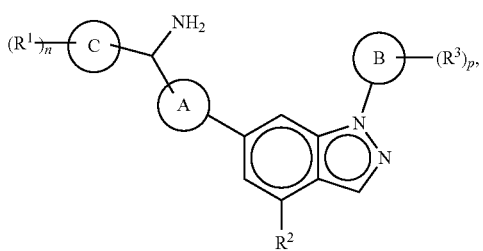

or a pharmaceutically acceptable salt thereof.

3. The compound of claim 1, wherein the compound is represented by the following structural formula:

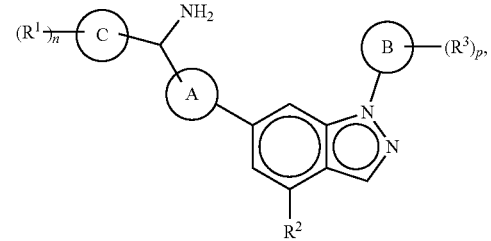

or a pharmaceutically acceptable salt thereof.

4. The compound of claim 1, wherein:
(i) Ring A is 5- or 6-membered heteroaryl and Ring B is 5- or 6-membered heteroaryl;
(ii) Ring A is a 5- or 6-membered heteroaryl and Ring B is phenyl;
(iii) Ring A is a phenyl and Ring B is a 5- or 6-membered heteroaryl; or
(iv) Ring A is a phenyl and Ring B is phenyl.

5. The compound of claim 4, wherein the 5- or 6-membered heteroaryl in each occurrence is independently selected from pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, or tetrazinyl.

6. The compound of claim 5, wherein the 5- or 6-membered heteroaryl in each occurrence is independently selected from pyridinyl, pyrimidinyl, pyrazinyl, thiazolyl, imidazolyl, oxazolyl pyrazolyl, and thiophenyl.

7. The compound of claim 1, wherein:
R$^1$ is selected from $C_{1-6}$alkyl, halo, —OR$^{1a}$, wherein said $C_{1-6}$alkyl are optionally substituted with one to three R$^{10}$;
R$^{1a}$ in each occurrence is independently selected from H or $C_{1-6}$alkyl wherein said $C_{1-6}$ alkyl in each occurrence are optionally and independently substituted with one to three R$^{10}$;
R$^{10}$ in each occurrence is independently selected from halo or —OR$^{10a}$; and
R$^{10a}$ in each occurrence is independently selected from H and $C_{1-6}$alkyl, wherein said $C_{1-6}$ alkyl is optionally substituted with one to three halo.

8. The compound of claim 1, wherein:
n is 1 and R$^1$ is OH or —CH$_2$OH; or
n is 2 and R$^1$ is halo.

9. The compound of claim 1, wherein:
Ring C is cyclobutyl; or
Ring C is cyclopentyl.

10. The compound of claim 1, wherein:
R$^2$ is selected from H, $C_{1-6}$alkyl, $C_{2-6}$alkenyl, $C_{2-6}$alkynyl, 3- to 7-membered carbocyclyl selected from cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, cycloheptatrienyl, and phenyl; 3- to 7-membered heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, azirinyl, oxirenyl, thiirenyl, diazirinyl, azetyl, oxetyl, thietyl, pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, thiazepinyl, dihydrofuranyl, imidazolinyl, and dihydropyranyl; halo, —CN, —C(O)$R^{2a}$, —C(O)$_2R^{2a}$, —C(O)N($R^{2a}$)$_2$, —NO$_2$, —N($R^{2a}$)$_2$, —N($R^{2a}$)C(O)$R^{2a}$, —N($R^{2a}$)C(O)$_2$ $R^{2a}$, —N($R^{2a}$)C(O)N($R^{2a}$)$_2$, —O$R^{2a}$, —OC(O)$R^{2a}$, and —OC(O)N($R^{2a}$)$_2$, wherein said $C_{1-6}$alkyl, $C_{2-6}$alkenyl, $C_{2-6}$ alkynyl, 3- to 7-membered carbocyclyl, and 3-7 membered heterocyclyl are optionally substituted with one to three $R^{20}$;

$R^{2a}$ in each occurrence is independently selected from H and $C_{1-4}$alkyl, wherein said $C_{1-4}$ alkyl in each occurrence is optionally and independently substituted with one to three $R^{20}$;

$R^{20}$ in each occurrence is independently selected from $C_{1-6}$alkyl, $C_{2-6}$alkenyl, $C_{2-6}$alkynyl, $C_{3-7}$cycloalkyl selected from cyclopropyl, cyclobutyl, cyclopentyl, cyclohexyl, and cycloheptyl; 3- to 7-membered saturated heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, and thiepanyl; halo, —CN, —C(O)$R^{20a}$, —C(O)$_2R^{20a}$, —C(O)N($R^{20a}$)$_2$, —N($R^{20a}$)$_2$, —N($R^{20a}$)C(O)$R^{20a}$, —N($R^{20a}$)C(O)$_2R^{20a}$, —N($R^{20a}$)C(O)N($R^{20a}$)$_2$, —O$R^{20a}$, —OC(O)$R^{20a}$ and —OC(O)N($R^{20a}$)$_2$, wherein said $C_{1-6}$alkyl, $C_{2-6}$alkenyl, $C_{2-6}$alkynyl, $C_{3-7}$cycloalkyl, and 3-7 membered saturated heterocyclyl in each occurrence are optionally and independently substituted with one to three $R^{25}$;

$R^{20a}$ in each occurrence is independently selected from H and $C_{1-4}$alkyl, wherein said $C_{1-4}$alkyl is optionally substituted with $R^{25}$;

$R^{25}$ is selected from halo and —O$R^{25a}$; and $R^{25a}$ is selected from H and $C_{1-4}$alkyl.

11. The compound of claim 1, wherein:
$R^2$ is H, $C_{1-4}$alkyl, $C_{2-4}$alkenyl, halo, —C(O)$_2R^{2a}$, —C(O)N($R^{2a}$)$_2$, —N($R^{2a}$)$_2$,N($R^{2a}$)C(O)$R^{2a}$, —CN, cyclopropyl, aziridinyl, azetidinyl, oxetanyl, pyrrolidinyl, imidazolidinyl, pyrazolidinyl, oxazolidinyl, isoxazolidinyl, piperidinyl, piperazinyl, azepanyl, oxepanyl, azirinyl, azetyl, pyrrolyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, pyrazinyl, pyrimidinyl, pyridazinyl, triazinyl, tetrazinyl, azepinyl, diazepinyl, thiazepinyl, and, imidazolinyl, wherein said $C_{1-4}$alkyl is optionally substituted with one to three groups selected from cyclopropyl, cyclobutyl, cyclopentyl, cyclohexyl, cycloheptyl, —O$R^{20a}$, —N($R^{20a}$)$_2$, N($R^{20a}$)C(O)$R^{2a}$, and halo;

$R^{2a}$ in each occurrence is independently selected from H and $C_{1-4}$ alkyl, wherein said $C_{1-4}$alkyl is optionally substituted with cyclopropyl, cyclobutyl, cyclopentyl, cyclohexyl, and cycloheptyl; and $R^{20a}$ in each occurrence is independently selected from H and $C_{1-4}$alkyl.

12. The compound of claim 1, wherein:
$R^2$ is H or —O$R^{2a}$; and
$R^{20}$ in each occurrence is independently selected from H and $C_{1-4}$alkyl, wherein said $C_{1-4}$ alkyl is optionally substituted with one to three halo.

13. The compound of claim 1, wherein:
p is 1 or 2;

each $R^3$ is independently selected from $C_{1-6}$alkyl, $C_{3-6}$cycloalkyl selected from cyclopropyl, cyclobutyl, cyclopentyl, and cyclohexyl, 3- to 6-membered saturated heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, and trithianyl; halo, —CN, —C(O)$R^{3a}$, —C(O)$_2R^{3a}$, —C(O)N($R^{3a}$)$_2$, —N($R^{3a}$)$_2$, —N($R^{3a}$)C(O)$R^{3a}$, —N($R^{3a}$)C(O)$_2R^{3a}$, —N($R^{3a}$)C(O)N($R^{3a}$)$_2$, —O$R^{3a}$, —OC(O)$R^{3a}$, —OC(O)N($R^{3a}$)$_2$, —S$R^{3a}$, —S(O)$R^{3a}$, —S(O)$_2R^{3a}$, —S(O)N($R^{3a}$)$_2$, and —S(O)$_2$N($R^{3a}$)$_2$, wherein said $C_{1-6}$alkyl, $C_{3-6}$cycloalkyl, and 3- to 6-membered saturated heterocyclyl are optionally substituted with one to three $R^{30}$;

$R^{3a}$ in each occurrence is independently selected from H, $C_{1-6}$ alkyl, 3- to 6-membered carbocyclyl selected from cyclopropyl, cyclobutyl, cyclopentyl, cyclohexyl, cyclopropenyl, cyclobutenyl, cyclopenentyl, cyclohexenyl, cyclobutadienyl, cyclopentadienyl, cyclohexadienyl, and phenyl, and 3- to 6-membered heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azirinyl, oxirenyl, thiirenyl, diazirinyl, azetyl, oxetyl, thietyl, pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, dihydrofuranyl, imidazolinyl, and dihydropyranyl; wherein said $C_{1-6}$ alkyl, 3- to 6-membered carbocyclyl, and 3- to 6-membered saturated heterocyclyl in each occurrence are optionally and independently substituted with one to three $R^{30}$;

$R^{30}$ in each occurrence is independently selected from $C_{1-6}$alkyl, 3- to 6-membered carbocyclyl selected from cyclopropyl, cyclobutyl, cyclopentyl, cyclohexyl, cyclopropenyl, cyclobutenyl, cyclopenentyl, cyclohexenyl, cyclobutadienyl, cyclopentadienyl, cyclohexadienyl, and phenyl; 3- to 6-membered heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azirinyl, oxirenyl, thiirenyl, diazirinyl, azetyl, oxetyl, thietyl, pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, dihydrofuranyl, imidazolinyl, and dihydropyranyl; halo, —CN, —C(O)$R^{30a}$, —C(O)$_2$$R^{30a}$, —C(O)N($R^{30a}$)$_2$, —N($R^{30a}$)$_2$, —N($R^{30a}$)C(O)$R^{30a}$, —N($R^{30a}$)C(O)$_2$$R^{30a}$, —N($R^{30a}$)C(O)N($R^{30a}$)$_2$, —O$R^{30a}$, —OC(O)$R^{30a}$, —OC(O)N($R^{30a}$)$_2$, S$R^{30a}$, —S(O)$R^{30a}$, —S(O)$_2$$R^{30a}$, —S(O)N($R^{30a}$)$_2$, and —S(O)$_2$N($R^{30a}$)$_2$, wherein said $C_{1-6}$alkyl, 3-6 membered carbocyclyl, and 3- to 6-membered heterocyclyl in each occurrence are optionally and independently substituted with one to three $R^{35}$;

$R^{30a}$ in each occurrence is independently selected from H and $C_{1-6}$alkyl, wherein $C_{1-6}$alkyl is optionally substituted with one to three $R^{35}$;

$R^{35}$ in each occurrence is independently selected from halo and —O$R^{35a}$; and $R^{35a}$ in each occurrence is independently selected from H and $C_{1-6}$alkyl.

14. The compound of claim 1, wherein $R^3$ in each occurrence is independently selected from $C_{1-4}$alkyl, —CN, halo, C(O)$_2$$R^{3a}$, C(O)N($R^{3a}$)$_2$, —N($R^{3a}$)$_2$, cyclopropyl, cyclobutyl, and —C(O)$R^{3a}$, wherein said $C_{1-4}$alkyl, cyclopropyl and cyclobutyl are optionally substituted with one to three groups selected from halo, N($R^{30a}$)$_2$, —CN, —S(O)$_2$$R^{30a}$, —C(O)N($R^{30a}$)$_2$, and —O$R^{30a}$;

$R^{3a}$ in each occurrence is independently selected from H, $C_{1-4}$ alkyl, and azetidinyl, wherein said $C_{1-4}$ alkyl and azetidinyl are optionally substituted with —O$R^{30a}$, N($R^{30a}$)$_2$, —CN, —S(O)$_2$$R^{30a}$, —C(O)$_2$$R^{30a}$, and —C(O)N($R^{30a}$)$_2$; and $R^{30a}$ in each occurrence is independently selected from H and $C_{1-4}$alkyl.

15. The compound of claim 1, wherein $R^3$ is selected from $C_{1-4}$alkyl and cyclopropyl, each of which is optionally substituted with one to three groups selected from halo, —O$R^{30a}$, and —CN; and $R^{30a}$ in each occurrence is independently selected from H and $C_{1-4}$ alkyl.

16. The compound of claim 1, wherein the compound is represented by formula:

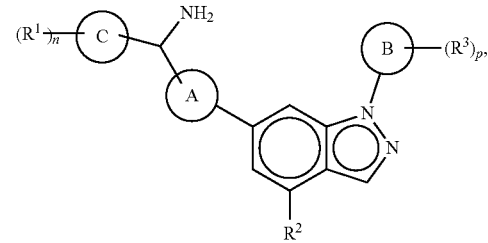

or a pharmaceutically acceptable salt thereof, wherein:
$R^1$ is F, OH or —CH$_2$OH;
Ring C is cyclobutyl or cyclopentyl;
Ring A is pyridinyl or pyrazinyl;
Ring B is pyridinyl, pyrazinyl, or pyrimidinyl;
$R^2$ is H or —O$R^{2a}$;
$R^{20}$ is H or $C_{1-4}$alkyl, wherein the $C_{1-4}$alkyl is optionally substituted with one to three halo;
$R^3$ is $C_{1-4}$alkyl or (C$_3$-C$_6$)cycloalkyl, wherein said $C_{1-4}$alkyl or (C$_3$-C$_6$)cycloalkyl is optionally substituted with one to three groups independently selected from halo, —O$R^{3a}$ or —CN and
$R^{3a}$ in each occurrence is independently selected form H and $C_{1-4}$alkyl.

17. A pharmaceutical composition, comprising at least one compound of claim 1, or a pharmaceutically acceptable salt thereof, and at least one pharmaceutically acceptable excipient.

18. A method of decreasing expression or activity of IRAK-4, the method comprising administering to a mammal an effective amount of at least one compound of claim 1, or a pharmaceutically acceptable salt thereof.

19. A method for treating an inflammatory disease in a subject, the method comprising administering to the subject patient in need thereof a therapeutically effective amount of at least one compound of claim 1, or a pharmaceutically acceptable salt thereof, thereby treating the inflammatory disease in the subject.

20. A method for treating an autoimmune disease, cancer, cardiovascular disease, a disease of the central nervous system, a disease of the skin, an ophthalmic disease and condition, and bone disease in a subject, the method comprising administering to the subject in need thereof a therapeutically effective amount of at least one compound of claim 1, or a pharmaceutically acceptable salt thereof, thereby treating the autoimmune disease, cancer, cardiovascular disease, disease of the central nervous system, disease of the skin, ophthalmic disease and condition, and bone disease in the subject.

* * * * *